United States Patent [19]

Kettleborough et al.

[11] Patent Number: 5,844,093
[45] Date of Patent: Dec. 1, 1998

[54] ANTI-EGFR SINGLE-CHAIN FVS AND ANTI-EGFR ANTIBODIES

[75] Inventors: A. Cathrine Kettleborough, Watford; Mary M. Bendig, Postfach; Keith H. Ansell, Hatfield; Detlef Güssow, Hampstead/London, all of Great Britain; Jaume Adan, Mataró, Spain; Francesc Mitjans, Igualada, Spain; Elisabet Rosell, Barcelona, Spain; Francesc Blasco, Sant Just Desvern, Spain; Jaume Piulats, Barcelona, Spain

[73] Assignee: Merck Patent Gesellschaft mit Beschrankter Haftung, Germany

[21] Appl. No.: 553,497

[22] PCT Filed: Mar. 16, 1995

[86] PCT No.: PCT/EP95/00978

§ 371 Date: Nov. 17, 1995

§ 102(e) Date: Nov. 17, 1995

[87] PCT Pub. No.: WO95/25167

PCT Pub. Date: Sep. 21, 1995

[30] Foreign Application Priority Data

Mar. 17, 1994 [EP] European Pat. Off. .............. 94104160
Dec. 2, 1994 [EP] European Pat. Off. .............. 94118970

[51] Int. Cl.⁶ .......................... C07K 16/28; C07H 21/04; A61K 39/395; C12N 15/63

[52] U.S. Cl. ..................... 530/387.3; 530/387.7; 530/388.22; 530/388.8; 530/388.85; 530/389.7; 536/235.53; 424/133.1; 424/135.1; 424/143.1; 435/6; 435/7.1; 435/7.2; 435/7.24; 435/252.3; 435/320.1; 435/69.1

[58] Field of Search .................. 424/134.1, 133.1, 424/135.1, 143.1; 435/69.1, 70.21, 240.27, 6, 7.1, 7.24, 7.2, 252.3, 320.1; 514/12; 530/387.3, 387.7, 388.22, 388.8, 388.85, 389.7; 536/23.53

[56] References Cited

U.S. PATENT DOCUMENTS 5,395,750  3/1995  Dillon et al. ................................ 435/5

FOREIGN PATENT DOCUMENTS

WO 90/14430  11/1990  WIPO .

OTHER PUBLICATIONS

Bender H. et al 1992 Cancer Res 52:121–126.
Masui, H. et al Cancer Res 49:3482–3488 1989.
McCafferty J. et al Noture 348:552–554 1990.
Chaudhary VK et al PNAS 87:1066–1070 1990.
Shin, S–U. Biotherapy 3:43–53 1991.

Primary Examiner—Toni R. Scheiner
Assistant Examiner—Nancy A. Johnson
Attorney, Agent, or Firm—Millen, White, Zelano & Branigan, P.C.

[57] ABSTRACT

This invention relates to new anti-EGFR antibodies and single-chain Fvs (scFvs) thereof which can be obtained from phage-antibody libraries constructed from cells of an immunized mammalian, preferably a mouse. Two of the single-chain Fvs isolated from the phage-antibody libraries were engineered to create partially humanized whole antibody molecules. These chimeric anti-EGFR antibodies contain constant regions of human immunoglobulins, and can be used as well as the single-chain Fvs as agents for the diagnosis and therapy of human tumors.

28 Claims, 9 Drawing Sheets

VH:

| scFv | FR 1 | CDR 1 | FR 2 |
|---|---|---|---|
| L3 11D | EVQLQQSGAELVKPGASVKLSCKASGYTFT | SYWMH | WVKQRPGQGLEWIG |
| L2 12B | QVQLQESGPELVKPGALVKISCKASGYTFT | SYWMH | WVKQRPGQGLEWIG |
| L3 10A | QVKLQESGGDLVKPGGSLKLSCAASGFTFS | SYGMS | WVRQTPDKRLESVA |
| L2 1C | EVKLQQSGAELVRPEASVKLSCKTSGYIFT | NYWIH | WVKQRSGQGLEWIA |
| L2 8C | QVQLQESGAELVRPGASVKLSCKTSGYIFT | NYWIH | WVKQRSGQGLEWIA |
| L2 11C | QVQLQESGPELVRPGASVKMSCKASGYTFT | TYWIH | WMKQRPGQGLQWIG |

| scFv | CDR 2 | FR 3 |
|---|---|---|
| L3 11D | EIDPSDSYTNYNQKFKG | KATLTVDKSSSTAYMQLSSLTSEDSAVYYCAR |
| L2 12B | EIDPSDSYTNYNQKFKG | KATLTVDKSSNTAYMQLSSLTSEDSAVYYCAR |
| L3 10A | TISSGGAYIYYPDSVKG | RFTISRDNAKNTLYLQMSSLKSEDTAMYYCAR |
| L2 1C | RIYPGNGSTYYNEKFKG | KATLTADKSSSTAYMQLSSLKSEDSAVYFCAR |
| L2 8C | KDLSWNGSYYNEKFKG | KATLTADKSSSTAYMQLSSLKSEDSAVYFCAR |
| L2 11C | MIDPSNSETRLNQNFRD | KATLSVDKSSNKAYMQLSSLTSEDSAIYYCAR |

| scFv | CDR 3 | FR 4 |
|---|---|---|
| L3 11D | SDYGSSHFDY | WGQGTTVTVSS |
| L2 12B | SDYGSSHFDY | WGQGTTVTVSS |
| L3 10A | LETGDYALDY | WGQGTTVTVSS |
| L2 1C | STSDSSLPYWYFDV | WGQGTTVTVSS |
| L2 8C | STSDSSLPYWYFDV | WGQGTTVTVSS |
| L2 11C | WDYGSGHFDY | WGQGTTVTVSS |

VK:

| scFv | FR 1 | CDR 1 | FR 2 |
|---|---|---|---|
| L3 11D | DIELTQSPASLAVSLGQRATISC | RASESVDNFGISFMN | WFQQKPGQPPKLLIY |
| L2 12B | DIELTQSPASLAVSLGQRATISC | RASESVDNFGISFMN | WFQQKPGQPPKLLIY |
| L3 10A | DIELTQSPASLAVSLGQRATISC | RASESVEYYGTSLMQ | WFQQKPGQPPKLLIY |
| L2 1C | DIELTQSPTILSTSPGEKVTVTC | RATLGVSYMH | WYQQKPGSSPKPWIY |
| L2 8C | DIELTQSPAIMSASPGEKVTITC | SASSSVSYMH | WFQQKPGTSPKLWIY |
| L2 11C | DIELTQSPASLAASVGETVTITC | RASENIYYSLA | WYQQKQGKSPQLLIY |

| scFv | CDR 2 | FR 3 |
|---|---|---|
| L3 11D | GASNQGS | GVPARFSGSGSGTDFSLNIHPLEEDDTAMYFC |
| L2 12B | GASNQGS | GVPARFSGSGSGTDFSLNIHPLEEDDTAMYFC |
| L3 10A | AASNVES | GVPARFSGSGSGTDFSLNIHPVEEDDIAMYFC |
| L2 1C | ATSNLAS | GVPARFSGSGSGTSYSLTISRVEAEDAATYYC |
| L2 8C | STSNLAS | GVPARFSGSGSGTSYSLTISRMEAEDAATYYC |
| L2 11C | SASALED | GVPSRFSGSGSGTQYSLKINNMQPEDTATYFC |

| scFv | CDR 3 | FR 4 |
|---|---|---|
| L3 11D | QQSKEVPLT | FGAGTKLELKRA |
| L2 12B | QQSKEVPLT | FGAGTKLEIKRA |
| L3 10A | QQSRKVPWT | FGGGTKLEIKRA |
| L2 1C | QQWISNPPT | FGGGTKLEIKRA |
| L2 8C | QQRNSYPHT | FGAGTKLELKRA |
| L2 11C | KQTYDVPWT | FGGGTKLEIKRA |

| scFv | FR 1 | CDR 1 | FR 2 |
|---|---|---|---|
| S4 2D | EVKLQQSGPELVKPGASVKMSCKASGYAFI | SFVMH | WVKQKPGQGLEWIG |
| S4 10H | EVKLQESGGDLVKPGGSLKLSCAASGFTFS | SYGMS | WVRQTPDKRLESVA |
| S4 5A | EVKLQESGGDSVKPGGSLKLSCAASGFTFS | SYGMS | WVRQTPDKRLESVA |
| S3 12D | EVKLQQSGAELVKPGASVKLSCTASGFNIK | DTYMH | WVKQRPEQGLEWIG |

| scFv | CDR 2 | FR 3 |
|---|---|---|
| S4 2D | FINPYNDGTKYNEKFKD | KATLTSDKSSSTAYMELSSLTSEDSAVYYCAS |
| S4 10H | TISSGGAYIYYPDSVKG | RFTISRDNAKNTLYLQMSSLKSEDTAMYYCAR |
| S4 5A | TISSGGAYIYYPDSVKG | RFTISRDNAKNTLYLQMSSLKSEDTAMYYCAR |
| S3 12D | RIDPANGNTKYDPKFQD | RASITADTSSNTAYLQLSSLTSEDTAVYYCAS |

| scFv | CDR 3 | FR 4 |
|---|---|---|
| S4 2D | GDYDRAMDY | WGQGTTVTVSS |
| S4 10H | LETGDYALDY | WGQGTTVTVSS |
| S4 5A | LETGDYAMDY | WGQGTTVTVSS |
| S3 12D | DYYGYEAWFAY | WGQGTTVTVSS |

VK:

| scFv | FR 1 | CDR 1 | FR 2 |
|---|---|---|---|
| S4 2D | DIELTQSPTTMAASPGEKITITC | SASSSISSNYLH | WYQQKPGFSPKLLIY |
| S4 10H | DIELTQSPASLAVSLGQRATISC | RASESVEYYGTSLMQ | WYQQKPGQAPKLLIY |
| S4 5A | DIELTQSPASLAVSLGQRATISC | RASESVEYYGTSLMQ | WYQQKPGQPPKLLIY |
| S3 12D | DIELTQSPASLAVSLGQRATISC | RASESVDNYGISFMN | WYQQKPGQPPKLLIY |

| scFv | CDR 2 | FR 3 |
|---|---|---|
| S4 2D | RTSNLAS | GVPARFSGSGSGTSYSLTIGTMEAEDVATYYC |
| S4 10H | AASNVES | EVPARFSGSGSGTDFSLNIHPVEEDDIAMYFC |
| S4 5A | AASNVES | GVPARFSGSGSGTDFSLNIHPVEEDDIAMYFC |
| S3 12D | AASNQGS | GVPARFSGSGSGTDFSLNIHPMEEDDTAMYFC |

| scFv | CDR 3 | FR 4 |
|---|---|---|
| S4 2D | QQGSSIPRT | FGGGTKLEIKRA |
| S4 10H | QQSRKVPWT | FGGGTKLEIKRA |
| S4 5A | QQSRKVPWT | FGGGTKLEIKRA |
| S3 12D | QQSKEVPWT | FGGGTKLEIKRA |

FIG. 1B

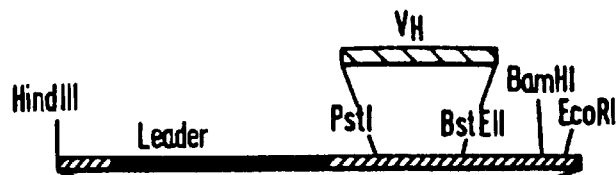

FIG. 3A

HindIII     Leader
AAGCTTGCCGCCACCATGGACTGGACCTGGCGCGTGTTTTGCCTGCTCGCCGTGGCTCCTG
          M  D  W  T  W  R  V  F  C  L  L  A  V  A  F
                    PstI                              BstEII
GGGCCCACAGCCAGGTGCAACTGCAGCAGTCCGGTGCCAAGGGACCACGGTCACCGTCTCC
 G  A  H  S  Q  V  Q  L  Q                       V  T  V  S
       BamHI EcoRI
TCAGGTGAGTGGATCCGAATTC
 S

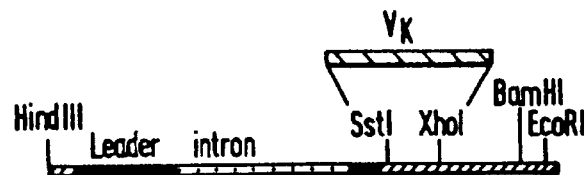

FIG. 3B

HindIII    Leader                                           intron
AAGCTTCGCCACCATGGGATGGAGCTGTATCATCCTCTTCTTGGTAGCAACAGCTACAGGTA
           M  G  W  S  C  I  I  L  F  L  V  A  T  A  T
AGGGGCTCACAGTAGCAGGCTTGAGGTCTGGACATATATATGGGTGACAATGACATCCACTT Leader              SstI                     XhoI
TGCCTTTCTCTCCACAGGTGTCCACTCCGACATTGAGCTCACCCAGTCTCCAGACAAAGCTC
                  G  V  H  S  D  I  E  L                    L
                                                      BamHI EcoRI
GAGCTGAAACGTGAGTAGAATTTAAACTTTGCTTCCTCAATTGGATCCGAATTC
 E  L  K

FIG. 5A

| | | | | | | | | | | | | | | | | |
|---|---|---|---|---|---|---|---|---|---|---|---|---|---|---|---|---|
| GAC | ATT | GAG | CTC | ACC | CAG | TCT | CCA | GCC | TCC | CTG | GCT | GCA | TCT | GTG | GGA | 48 |
| Asp | Ile | Glu | Leu | Thr | Gln | Ser | Pro | Ala | Ser | Leu | Ala | Ala | Ser | Val | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GAA | ACT | GTC | ACC | ATC | ACA | TGT | CGA | GCA | AGT | GAG | AAC | ATT | TAC | TAT | AGT | 96 |
| Glu | Thr | Val | Thr | Ile | Thr | Cys | Arg | Ala | Ser | Glu | Asn | Ile | Tyr | Tyr | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| TTA | GCA | TGG | TAT | CAG | CAG | AAG | CAA | GGG | AAA | TCT | CCT | CAG | CTC | CTG | ATC | 144 |
| Leu | Ala | Trp | Tyr | Gln | Gln | Lys | Gln | Gly | Lys | Ser | Pro | Gln | Leu | Leu | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| TAT | AGT | GCA | AGC | GCC | TTG | GAA | GAT | GGT | GTC | CCA | TCG | AGG | TTC | AGT | GGC | 192 |
| Tyr | Ser | Ala | Ser | Ala | Leu | Glu | Asp | Gly | Val | Pro | Ser | Arg | Phe | Ser | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| AGT | GGA | TCT | GGG | ACA | CAG | TAT | TCT | TTA | AAG | ATC | AAC | AAC | ATG | CAG | CCT | 240 |
| Ser | Gly | Ser | Gly | Thr | Gln | Tyr | Ser | Leu | Lys | Ile | Asn | Asn | Met | Gln | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GAA | GAT | ACC | GCT | ACT | TAC | TTC | TGT | AAA | CAG | ACT | TAT | GAC | GTT | CCG | TGG | 288 |
| Glu | Asp | Thr | Ala | Thr | Tyr | Phe | Cys | Lys | Gln | Thr | Tyr | Asp | Val | Pro | Trp | |
| | | | | 85 | | | | | 90 | | | | | 95 | | |

| | | | | | | | | | | |
|---|---|---|---|---|---|---|---|---|---|---|
| ACG | TTC | GGT | GGA | GGG | ACC | AAG | CTG | GAA | ATA | AAA | CGG | GCG | 327 |
| Thr | Phe | Gly | Gly | Gly | Thr | Lys | Leu | Glu | Ile | Lys | Arg | Ala | |
| | | | 100 | | | | | 105 | | | | | |

FIG. 5B

| | | | | | | | | | | | | | | | | |
|---|---|---|---|---|---|---|---|---|---|---|---|---|---|---|---|---|
| CAG | GTG | CAA | CTG | CAG | GAG | TCA | GGG | CCT | GAG | CTG | GTG | AGG | CCT | GGG | GCT | 48 |
| Gln | Val | Gln | Leu | Gln | Glu | Ser | Gly | Pro | Glu | Leu | Val | Arg | Pro | Gly | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| TCA | GTG | AAG | ATG | TCC | TGC | AAG | GCT | TCA | GGC | TAT | ACC | TTC | ACT | ACC | TAC | 96 |
| Ser | Val | Lys | Met | Ser | Cys | Lys | Ala | Ser | Gly | Tyr | Thr | Phe | Thr | Thr | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| TGG | ATA | CAC | TGG | ATG | AAA | CAG | AGG | CCT | GGA | CAA | GGC | CTT | CAG | TGG | ATT | 144 |
| Trp | Ile | His | Trp | Met | Lys | Gln | Arg | Pro | Gly | Gln | Gly | Leu | Gln | Trp | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| GGC | ATG | ATT | GAT | CCT | TCC | AAT | AGT | GAA | ACT | AGG | TTA | AAT | CAG | AAT | TTC | 192 |
| Gly | Met | Ile | Asp | Pro | Ser | Asn | Ser | Glu | Thr | Arg | Leu | Asn | Gln | Asn | Phe | |
| | | 50 | | | | | 55 | | | | | 60 | | | | |

| | | | | | | | | | | | | | | | | |
|---|---|---|---|---|---|---|---|---|---|---|---|---|---|---|---|---|
| AGG | GAC | AAG | GCC | ACA | TTG | AGT | GTA | GAC | AAA | TCC | TCC | AAT | AAA | GCC | TAC | 240 |
| Arg | Asp | Lys | Ala | Thr | Leu | Ser | Val | Asp | Lys | Ser | Ser | Asn | Lys | Ala | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ATG | CAG | CTC | AGC | AGC | CTG | ACA | TCT | GAG | GAC | TCT | GCA | ATC | TAT | TAC | TGT | 288 |
| Met | Gln | Leu | Ser | Ser | Leu | Thr | Ser | Glu | Asp | Ser | Ala | Ile | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| GCA | AGA | TGG | GAC | TAC | GGT | AGT | GGC | CAC | TTT | GAC | TAC | TGG | GGC | CAA | GGG | 336 |
| Ala | Arg | Trp | Asp | Tyr | Gly | Ser | Gly | His | Phe | Asp | Tyr | Trp | Gly | Gln | Gly | |
| | | | | 100 | | | | | 105 | | | | | 110 | | |

| | | | | | | |
|---|---|---|---|---|---|---|
| ACC | ACG | GTC | ACC | GTC | TCC | TCA | 357 |
| Thr | Thr | Val | Thr | Val | Ser | Ser | |
| | | | 115 | | | | |

FIG. 6A

| | | | | | | | | | | | | | | | | |
|---|---|---|---|---|---|---|---|---|---|---|---|---|---|---|---|---|
| GAC | ATT | GAG | CTC | ACC | CAG | TCT | CCA | GCT | TCT | TTG | GCT | GTG | TCT | CTA | GGG | 48 |
| Asp | Ile | Glu | Leu | Thr | Gln | Ser | Pro | Ala | Ser | Leu | Ala | Val | Ser | Leu | Gly | |
| 1 | | | | 5 | | | | | 10 | | | | | 15 | | |

| CAG | AGG | GCC | ACC | ATC | TCC | TGC | AGA | GCC | AGC | GAA | AGT | GTT | GAT | AAT | TTT | 96 |
|---|---|---|---|---|---|---|---|---|---|---|---|---|---|---|---|---|
| Gln | Arg | Ala | Thr | Ile | Ser | Cys | Arg | Ala | Ser | Glu | Ser | Val | Asp | Asn | Phe | |
| | | | 20 | | | | | 25 | | | | | 30 | | | |

| GGC | ATT | AGT | TTT | ATG | AAC | TGG | TTC | CAA | CAG | AAA | CCA | GGA | CAG | CCA | CCC | 144 |
|---|---|---|---|---|---|---|---|---|---|---|---|---|---|---|---|---|
| Gly | Ile | Ser | Phe | Met | Asn | Trp | Phe | Gln | Gln | Lys | Pro | Gly | Gln | Pro | Pro | |
| | | 35 | | | | | 40 | | | | | 45 | | | | |

| AAA | CTC | CTC | ATC | TAT | GGT | GCA | TCC | AAC | CAA | GGA | TCC | GGG | GTC | CCT | GCC | 192 |
|---|---|---|---|---|---|---|---|---|---|---|---|---|---|---|---|---|
| Lys | Leu | Leu | Ile | Tyr | Gly | Ala | Ser | Asn | Gln | Gly | Ser | Gly | Val | Pro | Ala | |
| | 50 | | | | | 55 | | | | | 60 | | | | | |

| AGG | TTT | AGT | GGC | AGT | GGG | TCT | GGG | ACA | GAC | TTC | AGC | CTC | AAC | ATC | CAT | 240 |
|---|---|---|---|---|---|---|---|---|---|---|---|---|---|---|---|---|
| Arg | Phe | Ser | Gly | Ser | Gly | Ser | Gly | Thr | Asp | Phe | Ser | Leu | Asn | Ile | His | |
| 65 | | | | | 70 | | | | | 75 | | | | | 80 | |

| CCT | CTG | GAG | GAG | GAT | GAT | ACT | GCA | ATG | TAT | TTC | TGT | CAG | CAA | AGT | AAG | 288 |
|---|---|---|---|---|---|---|---|---|---|---|---|---|---|---|---|---|
| Pro | Leu | Glu | Glu | Asp | Asp | Thr | Ala | Met | Tyr | Phe | Cys | Gln | Gln | Ser | Lys | |
| | | | | 85 | | | | | 90 | | | | | 95 | | |

| GAG | GTT | CCG | CTC | ACG | TTC | GGT | GCT | GGG | ACC | AAG | CTG | GAA | ATA | AAA | CGG | 336 |
|---|---|---|---|---|---|---|---|---|---|---|---|---|---|---|---|---|
| Glu | Val | Pro | Leu | Thr | Phe | Gly | Ala | Gly | Thr | Lys | Leu | Glu | Ile | Lys | Arg | |
| | | | 100 | | | | | 105 | | | | | 110 | | | |

| GCG | | | | | | | | | | | | | | | | 339 |
|---|---|---|---|---|---|---|---|---|---|---|---|---|---|---|---|---|
| Ala | | | | | | | | | | | | | | | | |

FIG. 6B

| CAG | GTG | CAG | CTG | CAG | GAG | TCT | GGA | CCT | GAG | CTG | GTG | AAG | CCT | GGG | GCT | 48 |
|---|---|---|---|---|---|---|---|---|---|---|---|---|---|---|---|---|
| Gln | Val | Gln | Leu | Gln | Glu | Ser | Gly | Pro | Glu | Leu | Val | Lys | Pro | Gly | Ala | |
| 1 | | | | 5 | | | | | 10 | | | | | 15 | | |

| TTA | GTG | AAG | ATA | TCC | TGC | AAG | GCT | TCT | GGT | TAC | ACC | TTC | ACC | AGC | TAC | 96 |
|---|---|---|---|---|---|---|---|---|---|---|---|---|---|---|---|---|
| Leu | Val | Lys | Ile | Ser | Cys | Lys | Ala | Ser | Gly | Tyr | Thr | Phe | Thr | Ser | Tyr | |
| | | | 20 | | | | | 25 | | | | | 30 | | | |

| TGG | ATG | CAC | TGG | GTG | AAG | CAG | AGG | CCT | GGA | CAA | GGC | CTT | GAG | TGG | ATC | 144 |
|---|---|---|---|---|---|---|---|---|---|---|---|---|---|---|---|---|
| Trp | Met | His | Trp | Val | Lys | Gln | Arg | Pro | Gly | Gln | Gly | Leu | Glu | Trp | Ile | |
| | | 35 | | | | | 40 | | | | | 45 | | | | |

| GGA | GAG | ATT | GAT | CCT | TCT | GAT | AGT | TAT | ACT | AAC | TAC | AAT | CAA | AAG | TTC | 192 |
|---|---|---|---|---|---|---|---|---|---|---|---|---|---|---|---|---|
| Gly | Glu | Ile | Asp | Pro | Ser | Asp | Ser | Tyr | Thr | Asn | Tyr | Asn | Gln | Lys | Phe | |
| | 50 | | | | | 55 | | | | | 60 | | | | | |

| AAG | GGC | AAG | GCC | ACA | TTG | ACT | GTA | GAC | AAA | TCC | TCC | AAC | ACA | GCC | TAC | 240 |
|---|---|---|---|---|---|---|---|---|---|---|---|---|---|---|---|---|
| Lys | Gly | Lys | Ala | Thr | Leu | Thr | Val | Asp | Lys | Ser | Ser | Asn | Thr | Ala | Tyr | |
| 65 | | | | | 70 | | | | | 75 | | | | | 80 | |

| ATG | CAG | CTC | AGC | AGC | CTG | ACA | TCT | GAG | GAC | TCT | GCG | GTC | TAT | TAC | TGT | 288 |
|---|---|---|---|---|---|---|---|---|---|---|---|---|---|---|---|---|
| Met | Gln | Leu | Ser | Ser | Leu | Thr | Ser | Glu | Asp | Ser | Ala | Val | Tyr | Tyr | Cys | |
| | | | | 85 | | | | | 90 | | | | | 95 | | |

| GCA | AGA | TCG | GAC | TAC | GGT | AGT | AGC | CAC | TTT | GAC | TAC | TGG | GGC | CAA | GGG | 336 |
|---|---|---|---|---|---|---|---|---|---|---|---|---|---|---|---|---|
| Ala | Arg | Ser | Asp | Tyr | Gly | Ser | Ser | His | Phe | Asp | Tyr | Trp | Gly | Gln | Gly | |
| | | | 100 | | | | | 105 | | | | | 110 | | | |

| ACC | ACG | GTC | ACC | GTC | TCC | TCA | | | | | | | | | | 357 |
|---|---|---|---|---|---|---|---|---|---|---|---|---|---|---|---|---|
| Thr | Thr | Val | Thr | Val | Ser | Ser | | | | | | | | | | |
| | | 115 | | | | | | | | | | | | | | |

FIG. 7A

| | | | | | | | | | | | | | | | | |
|---|---|---|---|---|---|---|---|---|---|---|---|---|---|---|---|---|
| GAC | ATT | GAG | CTC | ACC | CAG | TCT | CCA | GCT | TCT | TTG | GCT | GTG | TCT | CTA | GGG | 48 |
| Asp | Ile | Glu | Leu | Thr | Gln | Ser | Pro | Ala | Ser | Leu | Ala | Val | Ser | Leu | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| CAG | AGG | GCC | ACC | ATC | TCC | TGC | CGA | GCC | AGC | GAA | AGT | GTT | GAT | AAT | TTT | 96 |
| Gln | Arg | Ala | Thr | Ile | Ser | Cys | Arg | Ala | Ser | Glu | Ser | Val | Asp | Asn | Phe | |
| | | | 20 | | | | | 25 | | | | | 30 | | | |

| | | | | | | | | | | | | | | | | |
|---|---|---|---|---|---|---|---|---|---|---|---|---|---|---|---|---|
| GGC | ATT | AGT | TTT | ATG | AAC | TGG | TTC | CAA | CAG | AAA | CCA | GGA | CAG | CCA | CCC | 144 |
| Gly | Ile | Ser | Phe | Met | Asn | Trp | Phe | Gln | Gln | Lys | Pro | Gly | Gln | Pro | Pro | |
| | | 35 | | | | | 40 | | | | | 45 | | | | |

| | | | | | | | | | | | | | | | | |
|---|---|---|---|---|---|---|---|---|---|---|---|---|---|---|---|---|
| AAA | CTC | CTC | ATC | TAT | GGT | GCA | TCC | AAC | CAA | GGA | TCC | GGG | GTC | CCT | GCC | 192 |
| Lys | Leu | Leu | Ile | Tyr | Gly | Ala | Ser | Asn | Gln | Gly | Ser | Gly | Val | Pro | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| AGG | TTT | AGT | GGC | AGT | GGG | TCT | GGG | ACA | GAC | TTC | AGC | CTC | AAC | ATC | CAT | 240 |
| Arg | Phe | Ser | Gly | Ser | Gly | Ser | Gly | Thr | Asp | Phe | Ser | Leu | Asn | Ile | His | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| CCT | TTG | GAG | GAG | GAT | GAT | ACT | GCA | ATG | TAT | TTC | TGT | CAG | CAA | AGT | AAG | 288 |
| Pro | Leu | Glu | Glu | Asp | Asp | Thr | Ala | Met | Tyr | Phe | Cys | Gln | Gln | Ser | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| GAG | GTT | CCG | CTC | ACG | TTC | GGT | GCT | GGG | ACC | AAG | CTG | GAG | CTG | AAA | CGG | 336 |
| Glu | Val | Pro | Leu | Thr | Phe | Gly | Ala | Gly | Thr | Lys | Leu | Glu | Leu | Lys | Arg | |
| | | | 100 | | | | | 105 | | | | | 110 | | | |

| | |
|---|---|
| GCG | 339 |
| Ala | |

FIG. 7B

| | | | | | | | | | | | | | | | | |
|---|---|---|---|---|---|---|---|---|---|---|---|---|---|---|---|---|
| GAG | GTG | CAG | CTG | CAG | CAG | TCA | GGG | GCT | GAG | CTT | GTG | AAG | CCT | GGG | GCT | 48 |
| Glu | Val | Gln | Leu | Gln | Gln | Ser | Gly | Ala | Glu | Leu | Val | Lys | Pro | Gly | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| TCA | GTG | AAG | CTG | TCC | TGC | AAG | GCT | TCT | GGC | TAC | ACC | TTC | ACC | AGC | TAC | 96 |
| Ser | Val | Lys | Leu | Ser | Cys | Lys | Ala | Ser | Gly | Tyr | Thr | Phe | Thr | Ser | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| TGG | ATG | CAC | TGG | GTG | AAG | CAG | AGG | CCT | GGA | CAA | GGC | CTT | GAG | TGG | ATC | 144 |
| Trp | Met | His | Trp | Val | Lys | Gln | Arg | Pro | Gly | Gln | Gly | Leu | Glu | Trp | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| GGA | GAG | ATT | GAT | CCT | TCT | GAT | AGT | TAT | ACT | AAC | TAC | AAT | CAA | AAG | TTC | 192 |
| Gly | Glu | Ile | Asp | Pro | Ser | Asp | Ser | Tyr | Thr | Asn | Tyr | Asn | Gln | Lys | Phe | |
| | 50 | | | | | 55 | | | | | 60 | | | | | |

| | | | | | | | | | | | | | | | | |
|---|---|---|---|---|---|---|---|---|---|---|---|---|---|---|---|---|
| AAG | GGC | AAG | GCC | ACA | TTG | ACT | GTA | GAC | AAA | TCC | TCC | AGC | ACA | GCC | TAC | 240 |
| Lys | Gly | Lys | Ala | Thr | Leu | Thr | Val | Asp | Lys | Ser | Ser | Ser | Thr | Ala | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ATG | CAG | CTC | AGC | AGC | CTG | ACA | TCT | GAG | GAC | TCT | GCG | GTC | TAT | TAC | TGT | 288 |
| Met | Gln | Leu | Ser | Ser | Leu | Thr | Ser | Glu | Asp | Ser | Ala | Val | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| GCA | AGA | TCG | GAC | TAC | GGT | AGT | AGC | CAC | TTT | GAC | TAC | TGG | GGC | CAA | GGG | 336 |
| Ala | Arg | Ser | Asp | Tyr | Gly | Ser | Ser | His | Phe | Asp | Tyr | Trp | Gly | Gln | Gly | |
| | | | 100 | | | | | 105 | | | | | 110 | | | |

| | | | | | | |
|---|---|---|---|---|---|---|
| ACC | ACG | GTC | ACC | GTC | TCC | TCA | 357 |
| Thr | Thr | Val | Thr | Val | Ser | Ser | |
| | | 115 | | | | | |

FIG. 8A

| | | | | | | | | | | | | | | | | |
|---|---|---|---|---|---|---|---|---|---|---|---|---|---|---|---|---|
| GAC | ATT | GAG | CTC | ACC | CAG | TCT | CCA | ACC | ACC | ATG | GCT | GCA | TCT | CCC | GGG | 48 |
| Asp | Ile | Glu | Leu | Thr | Gln | Ser | Pro | Thr | Thr | Met | Ala | Ala | Ser | Pro | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GAG | AAG | ATC | ACT | ATC | ACC | TGC | AGT | GCC | AGC | TCA | AGT | ATA | AGT | TCC | AAT | 96 |
| Glu | Lys | Ile | Thr | Ile | Thr | Cys | Ser | Ala | Ser | Ser | Ser | Ile | Ser | Ser | Asn | |
| | | | 20 | | | | | 25 | | | | | 30 | | | |

| | | | | | | | | | | | | | | | | |
|---|---|---|---|---|---|---|---|---|---|---|---|---|---|---|---|---|
| TAC | TTG | CAT | TGG | TAT | CAG | CAG | AAG | CCA | GGA | TTC | TCC | CCT | AAA | CTC | TTG | 144 |
| Tyr | Leu | His | Trp | Tyr | Gln | Gln | Lys | Pro | Gly | Phe | Ser | Pro | Lys | Leu | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| ATT | TAT | AGG | ACA | TCC | AAT | CTG | GCT | TCT | GGA | GTC | CCA | GCT | CGC | TTC | AGT | 192 |
| Ile | Tyr | Arg | Thr | Ser | Asn | Leu | Ala | Ser | Gly | Val | Pro | Ala | Arg | Phe | Ser | |
| | | 50 | | | | | 55 | | | | | 60 | | | | |

| | | | | | | | | | | | | | | | | |
|---|---|---|---|---|---|---|---|---|---|---|---|---|---|---|---|---|
| GGC | AGT | GGG | TCT | GGG | ACC | TCT | TAC | TCT | CTC | ACA | ATT | GGC | ACC | ATG | GAG | 240 |
| Gly | Ser | Gly | Ser | Gly | Thr | Ser | Tyr | Ser | Leu | Thr | Ile | Gly | Thr | Met | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GCT | GAA | GAT | GTT | GCC | ACT | TAC | TAC | TGC | CAG | CAG | GGT | AGT | AGT | ATA | CCA | 288 |
| Ala | Glu | Asp | Val | Ala | Thr | Tyr | Tyr | Cys | Gln | Gln | Gly | Ser | Ser | Ile | Pro | |
| | | | | 85 | | | | | 90 | | | | | 95 | | |

| | | | | | | | | | | | |
|---|---|---|---|---|---|---|---|---|---|---|---|
| CGC | ACG | TTC | GGA | GGG | GGC | ACC | AAG | CTG | GAA | ATC | AAA | CGG | 327 |
| Arg | Thr | Phe | Gly | Gly | Gly | Thr | Lys | Leu | Glu | Ile | Lys | Arg | |
| | | | 100 | | | | | 105 | | | | | |

FIG. 8B

| | | | | | | | | | | | | | | | | |
|---|---|---|---|---|---|---|---|---|---|---|---|---|---|---|---|---|
| GAG | GTC | AAG | CTG | CAG | CAG | TCA | GGA | CCT | GAG | CTG | GTA | AAG | CCT | GGG | GCT | 48 |
| Glu | Val | Lys | Leu | Gln | Gln | Ser | Gly | Pro | Glu | Leu | Val | Lys | Pro | Gly | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| TCA | GTG | AAG | ATG | TCC | TGC | AAG | GCT | TCT | GGA | TAC | GCA | TTC | ATA | AGT | TTT | 96 |
| Ser | Val | Lys | Met | Ser | Cys | Lys | Ala | Ser | Gly | Tyr | Ala | Phe | Ile | Ser | Phe | |
| | | | 20 | | | | | 25 | | | | | 30 | | | |

| | | | | | | | | | | | | | | | | |
|---|---|---|---|---|---|---|---|---|---|---|---|---|---|---|---|---|
| GTT | ATG | CAC | TGG | GTG | AAG | CAG | AAG | CCT | GGG | CAG | GGC | CTT | GAG | TGG | ATT | 144 |
| Val | Met | His | Trp | Val | Lys | Gln | Lys | Pro | Gly | Gln | Gly | Leu | Glu | Trp | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| GGA | TTT | ATT | AAT | CCT | TAC | AAT | GAT | GGT | ACT | AAG | TAC | AAT | GAG | AAG | TTC | 192 |
| Gly | Phe | Ile | Asn | Pro | Tyr | Asn | Asp | Gly | Thr | Lys | Tyr | Asn | Glu | Lys | Phe | |
| | | 50 | | | | | 55 | | | | | 60 | | | | |

| | | | | | | | | | | | | | | | | |
|---|---|---|---|---|---|---|---|---|---|---|---|---|---|---|---|---|
| AAA | GAC | AAG | GCC | ACA | CTG | ACT | TCA | GAC | AAA | TCC | TCC | AGC | ACA | GCC | TAC | 240 |
| Lys | Asp | Lys | Ala | Thr | Leu | Thr | Ser | Asp | Lys | Ser | Ser | Ser | Thr | Ala | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ATG | GAG | CTC | AGC | AGC | CTG | ACC | TCT | GAG | GAC | TCT | GCG | GTC | TAT | TAC | TGT | 288 |
| Met | Glu | Leu | Ser | Ser | Leu | Thr | Ser | Glu | Asp | Ser | Ala | Val | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| GCA | AGT | GGG | GAT | TAC | GAC | AGG | GCT | ATG | GAC | TAC | TGG | GGC | CAA | GGG | ACC | 336 |
| Ala | Ser | Gly | Asp | Tyr | Asp | Arg | Ala | Met | Asp | Tyr | Trp | Gly | Gln | Gly | Thr | |
| | | | | 100 | | | | | 105 | | | | | 110 | | |

| | | | | | |
|---|---|---|---|---|---|
| ACG | GTC | ACC | GTC | TCC | TCA | 354 |
| Thr | Val | Thr | Val | Ser | Ser | |
| | | 115 | | | | |

ANTI-EGFR SINGLE-CHAIN FVS AND ANTI-EGFR ANTIBODIES

TECHNICAL FIELD OF THE INVENTION

This invention relates to new anti-EGFR antibodies and antibody fragments, preferably single-chain Fvs (scFvs) which can be obtained from phage-antibody libraries constructed from cells of an immunized mammalian, preferably a mouse. The antibody fragments isolated from the phage-antibody libraries can be engineered to create partially humanized whole antibody molecules. These chimeric anti-EGFR antibodies contain constant regions of human immunoglobulins, and can be used as well as their fragments as agents for the diagnosis and therapy of human tumors.

Furthermore, the invention demonstrates that phage-antibody libraries are an alternative, and more versatile, method for isolating antibodies from immunized mammalians in comparison with the standard hybridoma technology.

The invention relates, moreover, to pharmaceutical compositions comprising said antibodies or fragments for the purposes of treating tumors like melanoma, glioma or carcinoma. The said antibodies or fragments can be used also for diagnostic applications regarding locating and assessing the said tumors in vitro or in vivo.

The specification relates to several technical terms which are herewith defined as follows:

"FRs" (framework regions) mean the four subregions of the light or heavy chain variable regions that support the three CDRs.

"CDRs" (complementarity determining regions) mean the three subregions of the light or heavy chain variable regions which have hypervariable sequences and form loop structures that are primarily responsible for making direct contact with antigen.

"Chimeric" or partially humanized antibodies mean antibodies comprising constant regions deriving from human sources and variable regions (CDRs included) deriving from non-human sources, e.g. from the mouse.

"Humanized" or fully humanized antibodies mean antibodies comprising constant regions and FRs deriving from human sources whereas the CDRs derive from non-human sources.

"EGF" and "EGFR" mean the epidermal growth factor ant its receptor.

"PCR" means the polymerase chain reaction.

"scFv" means single-chain Fv which is an antibody fragment.

"$V_L$" means light chain variable region.

"$V_k$" means kappa light chain variable region.

"$V_H$" means heavy chain variable region.

PBS means phosphate buffered saline

FCS means fetal calf serum

HBSS means Hanks balanced salt solution

FITC means fluoresceineisothiocyanate

MTC means mixed cell culture

BACKROUND OF THE INVENTION

Epidermal growth factor (EGF) is a polypeptide hormone which is mitogenic for epidermal and epithelial cells. When EGF interacts with sensitive cells, it binds to membrane receptors (EGFR). The EGFR is a transmembrane glycoprotein of about 170 kD and is a gene product of the c-erb-B proto-oncogene.

MAb 425 is a murine monoclonal antibody raised against the well known human A431 carcinoma cell line (ATCC CRL 1555), binds to a polypeptide epitope of the external domain of the human EGFR, and inhibits the binding of EGF. MAb 425 (ATCC HB 9629) was found to mediate tumor cytotoxicity in vitro and to suppress tumor cell growth of epidermoid and colorectal carcinoma-derived cell lines in vitro (Rodeck et al., Cancer Res. 1987. 47: 3692). Humanized and chimeric versions of MAb 425 have been disclosed in WO 92/15683.

Over the last few years, methods have been described (Skerra and Plückthun, Science 1988. 240: 1038; Better et al., Science 1988. 240: 1041) with which functional antibody fragments can be produced in eukaryotic host cells, such as E. coli. These include the Fv fragment and the Fab fragment, whereby the Fv fragment is of special interest. Single-chain Fvs (wherein the $V_L$ and the $V_H$ chain are linked together) have been also described (Bird et al., Science 1988. 242: 423; Huston et al., Proc. Natl. Acad. Sci. USA 1988. 85: 5879).

Phage-antibody libraries offer an alternative technology to hybridoma technology in the isolation of antibodies from immunized animals. Hybridoma technology works by immortalizing the cells that produce the antibodies. Phage-antibody technology works by immortalizing the genes that code for the antibodies (Winter, G. and Milstein, C., Nature 1991. 349: 293). In phage-antibody technology, the antibody heavy chain variable region ($V_H$) and light chain variable region ($V_L$) genes are PCR-amplified, the variable regions are randomly combined and expressed as antibody fragments on the surface of phage particles, and libraries of phage antibodies are screened for antibodies that bind to antigens of interest.

Hybridoma technology has been very successful at isolating mouse monoclonal antibodies when it has been possible to generate a strong immune response in the spleens of the animals. For example, mouse MAbs against human epidermal growth factor receptor (EGFR) have been isolated from the spleens of mice immunized intraperitoneally with human A431 tumor cells (Murthy et al., Arch. Biochem. Biophys. 1987. 252:549). The potential advantage of phage-antibody technology over hybridoma technology is that virtually any source of antibody-expressing cells can be used as starting material and that large numbers of different antibodies can be rapidly screened. Another advantage of the phage-antibody technology is that the genes coding for the variable regions of the antibodies of interest have already been cloned and are immediately available for further genetic engineering.

In one report, an anti-tetanus toxoid Fab fragment isolated from a phage-antibody library was converted into a whole antibody molecule (Bender et al., Hum. Antibod. Hybridomas 1993. 4: 74).

During the last ten years, in vitro immunization has been used as an alternative technique to active immunization to generate monoclonal antibodies (mAbs) against a wide variety of antigens from both human and murine systems (e.g. Vaux, D. J. T.; Helenius, A. and Meliman, I.; Nature, 1988. 336: 36; Gathuru, J. K. et al.; J. Immunol. Methods, 1991. 137: 95; Borrebaeck, C. A. K.; Immunol. Today, 1988.9:355). Advantages of this approach are that only small amounts of antigen are required and that the method is applicable for generating human hybridomas. However, the generation of poor affinity IgM antibodies and the difficulty of immortalizing human lymphocytes after in vitro immunization have become persistent problems associated with this technology.

A new way of obtaining antibodies is by PCR amplification of repertoires of heavy ($V_H$) and light ($V_L$) chain variable region genes which are then randomly recombined and expressed as phage display libraries (7–9). Antibody variable-region genes were cloned and fused to the minor coat protein (gene 3) as a single chain Fv fragment (scFv) (10). The phage particle displays on its surface the antibody fragment and can be selected by panning using the antibody's binding properties. This technology has the advantage that random recombination of V genes may produce novel pairings with new specificities and affinities which could not be selected by natural processes. Moreover, such an approach makes possible the use of naive or in vitro immunized lymphocytes from murine or human sources.

Previous attempts to obtain mAbs against EGFR by murine B cells in vitro immunization and hybridoma technology rendered low-affinity, cross-reacting antibodies. In order to overcome such handicaps, the combination of in vitro immunization followed by PCR cloning technology was carried out.

Therefore, it is an object of the invention to develop antibodies and antibody fragments which have a high affinity to the EGF-receptor and which can be obtained by the advantageous procedure described above and below.

SUMMARY OF THE INVENTION

This invention compares mouse anti-EGFR antibodies isolated from three different phage-antibody libraries with a mouse MAb (425) isolated by standard hybridoma technology (Murthy et al., *Arch. Biochem. Biophys.* 1987. 252:549; Kettleborough et al., *Protein Eng.* 1991. 4: 773). Libraries were prepared, not only from the spleen of an immunized mouse, but also from the draining lymph node of an immunized mouse and from in vitro immunized mouse cells. Two of the single-chain Fvs (scFvs) that were isolated from the libraries were engineered to create chimeric whole antibody molecules with the mouse variable regions joined to human constant regions.

In detail, the present invention relates to an anti-EGFR single-chain Fv obtainable from phage-antibody libraries constructed from cells, preferrably of the spleen or the draining lymph node of an immunized mammalian, preferably a mouse, or from in vitro immunized cells. In principal, the invention is not restricted to scFvs but extends also to other anti-EGFR antibody fragments such as Fab or F(ab')$_2$.

Some of the scFvs according to the invention have well-defined DNA and amino acid sequences. Therefore, it is another object of the invention to provide a single-chain Fv fragment, wherein the variable regions of the heavy and light chain comprise a DNA and/or a amino acid sequence selected from one of the heavy and light chain sequences given in Sequence Id. Nos. 1–32, preferably in FIG. 5–8.

Because in many cases only completely functioning, whole antibodies can be used for diagnostic and therapeutic purposes it is in the interest of the invention to link the variable regions from single-chain Fvs with the constant regions of human immunoglobulins forming whole, partially or humanized anti-EGFR antibodies.

Therefore, it is an object of this invention to provide a whole anti-EGFR antibody constructed from DNA sequences deriving from antibody fragments as defined above, below or as defined in the claims, and from DNA sequences deriving from constant regions of human immunogobulins, wherein, as a preferred embodiment, the heavy chain comprises the amino acid sequence of a gamma-1 chain, and the light chain comprises the amino acid sequence of a kappa chain.

According to the present invention the anti-EGFR scFvs, are isolated by using the phage-antibody library technology. Therefore the invention relates to a process for the preparation of an anti-EGFR single-chain Fv comprising the following steps:

(i) isolating RNA from immunized mammalian cells, preferably mouse cells, (ii) synthesizing first-strand cDNA, (iii) amplifying the $v_H$ and $V_k$ genes in cDNAs from the immunized cells, (iv) cloning said genes together with suitable restriction sites into a phagemid vector, (v) transforming prokaryotic cells with the ligation mixtures, (vi) screening the phage libraries for phage antibodies directed to EGFR using purified EGFR, and (vii) producing the desired single-chain Fv in prokaryotic host cells, preferably *E. coli*.

Additionally, it is an object of the invention to disclose a process for the preparation of a whole anti-EGFR antibody by cloning the DNA coding for the variable regions of anti-EGFR antibody fragments produced as indicated above or as defined in the claims into at least one eukaryotic expression vector containing genomic DNA which codes for the constant regions of human immunoglobulins, transforming eukaryotic cells with said vector(s) and expressing and isolating the antibody.

The anti-EGFR scFvs, and above all, the whole anti-EGFR antibodies can be used in diagnosis and therapy of human tumors. Thus, the invention relates to a pharmaceutical composition comprising an anti-EGFR single chain Fv or a whole anti-EGFR antibody as defined above or as defined in the claims.

The results and advantages of the present invention can be summarized as follows:

Novel mouse anti-EGFR antibodies were isolated from phage-antibody libraries. The new antibodies represented at least four different $v_H$ subgroups and four different $V_K$ subgroups (Kabat et al., *Sequences of proteins of immunological interest* 5th Eds., U.S. Dept. of Health and Human Services, Bethesda 1991). They showed different pairings and sequences from those used by a mouse MAb isolated using hybridoma technology. Mouse 425 MAb has a $v_H$2b and $V_k$4 pairing that was not observed in the phage antibodies. The $v_H$ of scFv L3 11 D had the highest percent identity to 425$v_H$ (84.9%). The majority of the differences were in the CDRs. The $V_k$ of scFv S4 2D had the highest percent identity to 425 $V_k$ (83.2%). Again the majority of differences were in the CDRs, particularly CDR3. In this invention, a variety of new anti-EGFR antibodies were isolated from the phage-antibody libraries and these antibodies all differ from 425 MAb with at least two of the scFvs recognizing a different epitope on EGFR from that recognized by 425 MAb. This is in contrast to a previous report where the antibodies isolated from combinatorial libraries were reported to be very similar to those isolated by hybridoma technology (Caton and Koprowski, *Proc. Natl. Acad. Sci. USA* 1990. 87:6450).

Of the three phage-antibody libraries, the best library in terms of the number of selection steps required to get high affinity antibodies and in terms of the diversity of high affinity antibodies isolated was the library generated from the draining lymph node. Lymph nodes were selected as a source of RNA for the construction of phage-antibody libraries for two reasons. First, previous work had demonstrated that a higher proportion of B cells producing high affinity IgG antibodies was obtained from the popliteal lymph nodes following immunization via the footpad than from spleens following immunization via the peritoneum (Venn and Dresser, *J. Immunol. Methods* 1987. 102: 95). Second, draining lymph nodes are considered to be a good source for the isolation of human anti-tumor antibodies. Thus, the isolation of mouse anti-EGFR antibodies from the popliteal lymph node of a footpad-immunized mouse was a model for the isolation of human anti-EGFR antibodies from the axillary lymph nodes of a breast cancer patient. The feasibility of preparing good size libraries from small amounts of lymph node material and of then isolating high affinity antibodies from the libraries was demonstrated.

Although mouse anti-EGFR antibodies were isolated from all three phage-antibody libraries, it is not clear that any of the newly isolated antibodies have higher affinities than the mouse 425 MAb isolated using hybridoma technology. In the first analyses, the phage-antibody derived scFvs appeared to bind to EGFR better than the scFv constructed from 425 MAb (FIG. 2). In other experiments with chimeric whole antibody molecules, one of the chimeric antibodies (S4 2D) showed an affinity for EGFR that equalled that of the chimeric 425 antibody. The second chimeric antibody (L3 11 D) had an affinity that was four-fold lower than that of chimeric 425 antibody (FIG. 4). Binding data obtained using scFvs was misleading probably because preparations of scFvs can contain mixtures of monomers and dimers (Griffiths et al., *EMBO J.* 1993. 12:725). In contrast, chimeric IgG antibodies are not expected to form dimers and the chimeric L3 11 D and S4 2D antibodies were demonstrated to be the size expected for bivalent, monomeric chimeric IgG antibodies. Analysis of affinity-purified preparations of 425, L3 11 D, and S4 2D scFvs, however, showed that these preparations of scFvs did contain monomeric, dimeric, and other multimeric forms. In addition, the relative proportions of monomeric and multimeric forms varied for each scFv. The 425 scFv had the lowest percentage of dimeric forms. As predicted, the dimeric and particularly the larger multimeric forms showed stronger binding to purified EGFR than the monomeric form. It appears that 425 scFv has a weaker tendency to dimerize than some of the newly isolated scFvs.

Although the expression of antibody fragments on the surface of phage particles forms the basis of a powerful method for rapidly selecting for antibodies with the desired specificities, neither phage antibodies nor the antibody fragments themselves (scFvs or Fabs) are likely to be the desired end product. Further it is demonstrated how the mouse scFvs isolated from phage libraries can be readily converted into whole antibody molecules. In this case, the mouse variable regions were joined to human constant regions to create partially humanized chimeric antibodies.

These results show that it is possible to use phage-antibody technology to isolate a variety of anti-EGFR antibody fragments from immunized mice. Whole antibody molecules with the desired constant regions can then be constructed from the antibody fragments. In some cases, hybridoma technology may still be the method of choice for isolating monoclonal antibodies from mice. If a highly immunogenic antigen is available and if a few hybridoma cell lines producing one or a few different anti-antigen antibodies are adequate, then there is probably little reason to consider phage-antibody technology. If, however, special immunization protocols such as footpad injections would be advantageous in generating high affinity antibodies, or if a large number of antibodies against a variety of epitopes on the antigen are required, or if antibodies directed against a very discreet, and possibly less immunogenic, epitope are required, then phage-antibody technology may be the method of choice. Also, if further genetic engineering of the antibodies is anticipated, then the phage-antibody technology is advantageous in that the antibody genes have already been cloned.

The present approach of combining in vitro immunization with a particulate antigen and PCR-cloning technology has generated scFv fragments which reacted with EGFR and did not cross-react with other antigens. The immunization protocol reported here depends on the antigen presentation, which is not soluble but is a membrane vesicle preparation, and on the culture medium itself, which is devoid of FCS. Both methodologies have been reported as a means of increasing the efficiency of in vitro immunization by making the antigen available to the antigen-presenting cells (e.g. Brams, P. et al.; J. Immunol. Methods, 1987. 98:11).

The results obtained with MTC are in agree with previous papers (e. g. Borrebaeck, C. A. K and Möller, S. A; J. Immunol., 1986. 136: 3710; Möller, S. A. and Borrebaeck, C. A. K., in Borrebaeck, C. A. K. (Eds.), In Vitro Immunization in Hybridoma Technology, Elsevier Science Publishers B.V., Amsterdam 1988, p. 3.) which propose the use of MTC supernatants as a source of lymphokines for improving the in vitro immunization process. The membrane vesicle preparation should be envisaged as a poly-antigen since many different antigenic determinants are present in such vesicles. For this reason, it would appear that they induce a certain level of polyclonal activation. We have ruled this out because the anti-EGFR specific response was clearly different from the response obtained after a standard polyclonal activator.

Instead of immortalizing the B-cells after in vitro immunizations, we have used the molecular strategy of immortalizing the antibody $V_H$ and $V_L$ genes. These monoclonal antibody fragments were expressed and produced in bacteria. The phage display system is a powerful method to isolate antibody fragments against specific antigens. The presence of a stop codon between the antibody fragment and the g3p coat protein permits the switch between surface display and secretion as a soluble scFv fragment using suppressor or non-suppresor strains (Hoogenboom et al., Nucl. Acids Res. 1991. 19: 4133).

Due to the increase of specific response and mRNA levels in in vitro antigen stimulated B-cells, in vitro immunization contributes to the isolation of antibody fragments with high specificities to the antigen. After two rounds of selection, 100% of the clones were positive for binding EGFR. In contrast, clones derived from in vivo immunization processes were 100% positive only after four rounds of selection (Kettleborough, et al., EP 94104160 and Eur. J. Immunol. 1994.24: 952).

The use of phage display libraries from naive antibody genes might allow specific human antibody fragments to be made without immunization or after in vitro immunization. Antibody fragments can be directly produced in bacteria, thus in a simple, fast and economic way.

BIOLOGICAL MATERIALS AND GENERAL METHODS

Microorganisms, cell lines, plasmids, phagemids, promoters, resistance markers, replication origins or other fragments of vectors which are mentioned in this application are commercially or otherwise generally available. Provided that no other information in the application is given, they are used only as examples and are not essential according to the invention and can be replaced by other suitable tools and biological materials, respectively.

Bacterial hosts are preferably used for cloning the scFvs and for producing the scFv proteins. Examples for these hosts are: E. coli or Bacillus.

Eukaryotic hosts like COS, CHO or yeasts, for example, are preferred in order to produce the whole anti-EGFR-antibodies according to the invention.

The techniques which are essential according to the invention are described in detail in the specification. Other techniques which are not described in detail correspond to known standard methods which are well known to a person skilled in the art, or are described more in detail in the cited references and patent applications and in the standard literature.

BRIEF DESCRIPTION OF THE FIGURES

FIG. 1. Amino acid sequences of scFvs isolated from phage-antibody libraries. (FIG. 1A) scFvs from the lymph node library. (FIG. 1B) scFvs from the spleen library. Complementarity determining regions (CDRs) and framework regions (FRs) are indicated.

FIG. 2. Binding of scFvs to EGFR. The concentrations of scFvs in bacterial supernatants were estimated and the scFvs tested by ELISA for binding to purified EGFR.

FIG. 3. Intermediate vectors used to reconstruct the variable regions for expression in mammalian cells. (FIG. 3A) $V_H$ vector. (FIG. 3B) $V_k$ vector.

FIG. 5. DNA and amino acid sequence of scFv No. L2 11C. (FIG. 5A): Light chain (SEQ ID NO:1,2); (FIG. 5B): Heavy chain (SEQ ID NO:3,4).

Figure 2A:
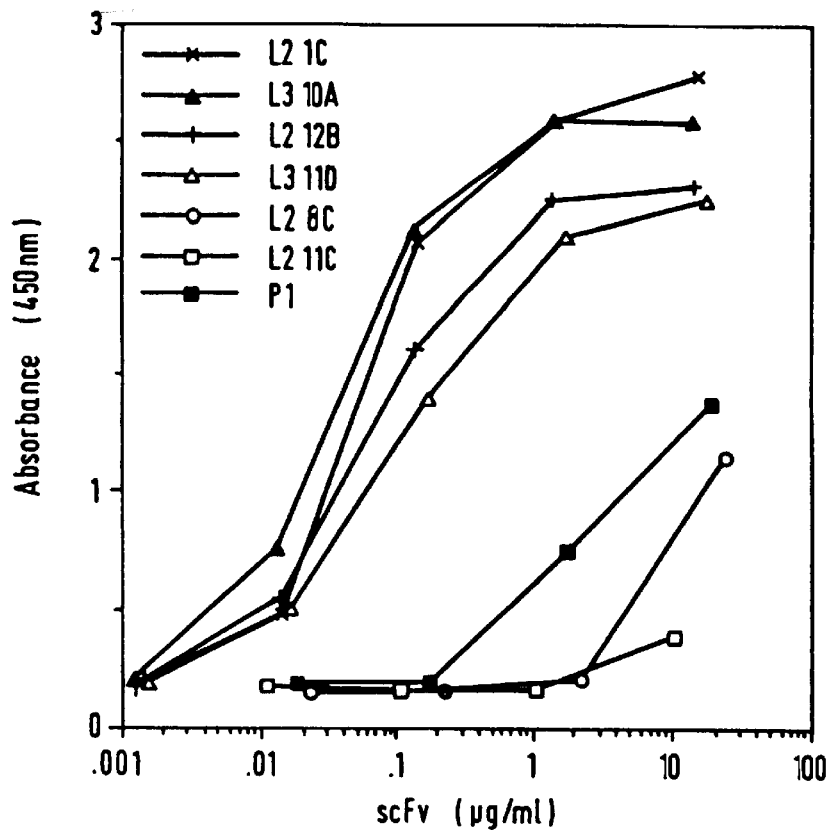
(FIG. 2A) scFvs from the lymph node library.

Amino acid positions:

(A)

FR-1: 1–23, CDR-1: 24–34,

FR-2: 35–49, CDR-2: 50–56,

FR-3: 57–88, CDR-3: 89–97,

FR-4: 98–109.

(B)

FR-1: 1–30, CDR-1: 31–35,

FR-2: 36–49, CDR-2: 50–66,

FR-3: 67–98, CDR-3: 99–108,

FR-4: 109–119.

FIG. 6. DNA and amino acid sequence of scFv No. L2 12B. (FIG. 6A): Light chain (SEQ ID NO:5,6); (FIG. 6B): Heavy chain (SEQ ID NO:7,8).

Amino acid positions:

(A)

FR-1: 1–23, CDR-1: 24–38,

FR-2: 39–49, CDR-2: 50–56,

FR-3: 57–88, CDR-3: 89–97,

FR-4: 98–109.

(B)

FR-1: 1–30, CDR-1: 31–35,

FR-2: 36–49, CDR-2: 50–66,

FR-3: 67–98, CDR-3: 99–108,

FR-4: 109–119.

FIG. 7. DNA and amino acid sequence of scFv No. L3 11D. (FIG. 7A): Light chain (SEQ ID NO:9,10); (FIG. 7B): Heavy chain (SEQ ID NO:11,12).

The amino acid posititions of the FRs and CDRs correspond to those given in FIG. 6.

FIG. 8. DNA and amino acid sequence of scFv No. S4 2D (FIG. 8A): Light chain (SEQ ID NO:13,14); (FIG. 8B): Heavy chain (SEQ ID NO:15,16).

Amino acid positions:

(A)

FR-1: 1–23, CDR-1: 24–35,

FR-2: 36–50, CDR-2: 51–57,

FR-3: 58–89, CDR-3: 90–98,

FR-4: 99–110

(B)

FR-1: 1–30, CDR-1: 31–35,

FR-2: 36–49, CDR-2: 50–66,

FR-3: 67–98, CDR-3: 99–107,

FR-4: 108–118.

The sequences of FIGS. 5–8 are also given in the attached Sequence Listing which is part of the disclosure of this invention.

DETAILED DESCRIPTION OF THE INVENTION (1) Construction and screening of phage-antibody libraries Three phage-antibody libraries were constructed, one from the spleen of a mouse immunized with human carcinoma cell line A431 ($8.8 \times 10^5$ members), one from the popliteal lymph node of a mouse immunized in the footpad with purified EGFR ($6.5 \times 10^6$ members), and one from mouse lymphocytes immunized in vitro with A431 vesicles ($1.1 \times 10^5$ members), (details of construction of A431 vesicles and in vitro-immunization are given in Examples 1, 2). Prior to selection, at least 46 clones from each library were analyzed by BstNI fingerprinting (Clackson et al, Nature 1991. 352: 624) to determine the diversity of the repertoires. A wide range of digestion patterns was observed. Also prior to selection, scFvs from 96 clones from each library were tested by ELISA for binding to EGFR. None of the scFvs from the spleen and lymph node library bound to EGFR. One of the scFvs from the in vitro immunized library bound to EGFR. After one round of selection using EGFR-coated immunotubes, a clear enrichment for EGFR-binding scFvs was observed with the lymph node library and with the in vitro immunized library. A second round of selection was needed before any EGFR-binding scFvs were detected from the spleen library. By the third round of selection, the majority of the scFvs from the lymph node and in vitro immunized libraries were positive for binding to EGFR. After a fourth round of selection with the spleen library, the majority of the scFvs were positive for binding to EGFR (Table 1).

TABLE 1

Percent of EGFR-binding clones after each round of selection.

|  | Lymph Node Library | Spleen Library | In vitro Immunized Cells Library |
|---|---|---|---|
| Pre-selection | 0 | 0 | 1 |
| First round | 77 | 0 | 84 |
| Second round | 86 | 26 | 100 |
| Third round | 90 | 77 | 100 |
| Fourth round | not tested | 97 | not tested |

(2) Sequence analysis of EGFR-binding clones

After each round of selection, scFv inserts from EGFR-binding clones were analyzed by BstNI fingerprinting (Clackson et al, *Nature* 1991. 352: 624). It became clear that there was an enrichment for certain digestion patterns. Clones with different BstNI fingerprints were chosen from the second and third rounds of selection of the lymph node library and from the third and fourth rounds of the spleen library for DNA sequencing of the $V_H$s and $V_K$s. Clones from later rounds of selection were analyzed because higher affinity antibodies were expected to be in the later rounds (Clackson et al, *Nature* 1991. 352: 624).

Sixteen clones from the lymph node library were sequenced and six different scFvs were obtained (FIG. 1). Five of these were pairings of unique $V_H$s and $V_K$s. The sixth was a variation of a previously occurring $V_H$ with six amino acid changes, five of which were in framework region (FR) 1. Two of these changes can be attributed to the use of the degenerate VH1 BACKSFI primer (Hoogenboom et al., *Nucl. Acids Res.* 1991. 19: 4133). The others may be a result of PCR errors. The $V_H$s were classified into two subgroups, $V_H2b$ and $V_H3d$, while the $V_K$s fell into four subgroups, $V_K3$, $V_K4$, $V_K5$, and $V_K6$ (Kabat et al., *Sequences of proteins of immunological interest*. 5th Eds., U.S. Dept. of Health and Human Services, Bethesda 1991). Ten individual clones from the spleen library were sequenced and four different scFvs were found. Three of these were pairings of unique $V_H$s and $V_K$s while the fourth was similar to one of the previous pairings with only two amino acid differences in $V_H$, one of which occurred in complementarity determining region (CDR) 2, and two amino acid differences in $V_K$. Classification into subgroups revealed $V_H$s from subgroups $V_H2a$, $V_H2c$, and $V_H3d$ and $V_K$S from subgroups $V_K3$ and $V_K4$. Comparison of the scFvs obtained from the lymph node and spleen libraries revealed only one scFv that was common to both libraries, scFv L3 10A/scFv S4 1OH (FIG. 1). This clone appeared to bind strongly to EGFR when tested by ELISA. While much care was taken to eliminate any cross-contamination between libraries, it is difficult to rule out minor contamination with a strongly-binding EGFR clone. However, considering the inbred nature of Balb/c mice, it is possible that the same scFv arose independently from two different libraries.

(3) Analysis of the affinity and specificity of binding to EGFR

Based on good binding to antigen and diversity in DNA sequences, several scFvs derived from the lymph node and spleen libraries were chosen for further analysis. These scFvs were analyzed by ELISA for binding to purified EGFR, binding to irrelevant antigens, and binding to tumor cell lines that did or did not express EGFR. As a positive control, scFvs were prepared from mouse 425 MAb (P1). As negative controls, scFvs were prepared from phage antibodies isolated from the lymph node and spleen libraries prior to selection (L1 and S1, respectively). The concentration of scFvs was determined by comparing dilutions of the scFvs to be tested with dilutions of a purified scFv of known concentration in a Western blot.

Figure 2B:
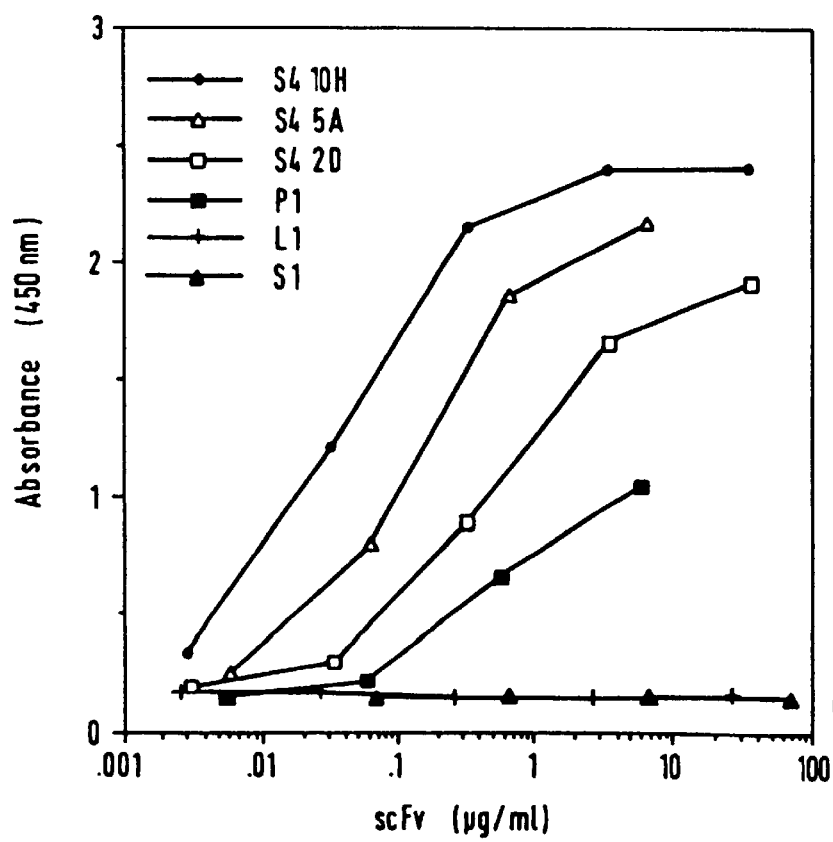
(FIG. 2B) scFvs from the spleen library. P1 (positive control) is the scFv derived from MAb 425. L1 and S1 (negative. controls) are non-binding scFvs from the pre-selected lymph node and spleen libraries.

The scFvs were tested by ELISA for binding to purified EGFR and the results plotted (FIG. 2). It was possible to rank the scFvs with respect to their binding to EGFR. These rankings were reproducible between experiments. The scFvs that bound most strongly to EGFR were L2 1C and L3 10A from the lymph node library and S4 10H from the spleen library. As described previously, scFvs L3 10A and S4 10H have the same DNA sequences. A scFv (S4 5A) that was very similar to scFv S4 10H, with two amino acid changes in $V_H$ and two in $V_k$, consistently gave a lower ranking than S4 10H. In contrast, the differences in sequence observed between L2 12B and L3 11D did not appear to have a pronounced effect on the binding. Of the scFvs isolated only two, L2 8C and L2 11C, appeared to bind less well than scFv 425.

The scFvs were tested by ELISA for binding to plastic and to a panel of unrelated proteins (ovalbumin, hen egg lysozyme, cytochrome c, glyceraldehyde 3-phosphate dehydrogenase, CBA albumin, and BSA). None of the scFvs gave a signal above background.

The scFvs were tested by ELISA for binding to three tumor cell lines. Cell lines A431 and MDA MB 468 are EGFR-bearing tumor cells isolated from the vulva and breast, respectively. Cell line SK-MEL-23 is a ganglioside-bearing melanoma cell line and was included as a negative control. Of the ten scFvs tested, only four bound to both purified EGFR and EGFR-bearing tumor cells (L2 12B, L3 11 D, L2 11C, and S4 2D, FIGS. 5–8). No binding to SK-MEL-23 cells was detected. There are several possible explanations for this surprising result. One may be that the EGFR that was used for immunization, selection, and ELISA was secreted EGFR-related protein (Weber et al., *Science* 1984. 224: 294). This protein has an additional 17 amino acids at the C-terminus (Günther et al., *J Biol. Chem.* 1990. 265; 22082). The scFvs were tested by ELISA for binding to this 17 amino acid peptide and no binding was observed. It is possible that the secreted EGFR-related protein and the EGFR on the tumor cell surface have differences in conformation or glycosylation.

To further investigate binding to tumor cells, three scFvs (L2 11A, L3 11D and S4 2D) were purified and analyzed for binding to A431 tumor cells by flow cytometry. The 425 scFv was used as a positive control. Of the three scFvs tested, only L3 11 D and S4 2D bound to A431 cells. These two scFvs had similar binding profiles to scFv 425.

Purified scFvs prepared from two of the isolates that bound to both EGFR and EGFR-bearing tumor cells (L3 11D and S4 2D) were tested in competition binding assays with mouse 425 MAb. While purified scFv 425 was able to inhibit mouse 425 MAb from binding to EGFR over a given concentration range, scFvs L3 11D and S4 2D did not inhibit mouse 425 MAb from binding to EGFR at these concentrations. These two scFvs appear to recognize an epitope on EGFR that is different from that recognized by mouse 425 MAb.

(4) Chimeric whole antibodies derived from scFvs.

Figure 4:
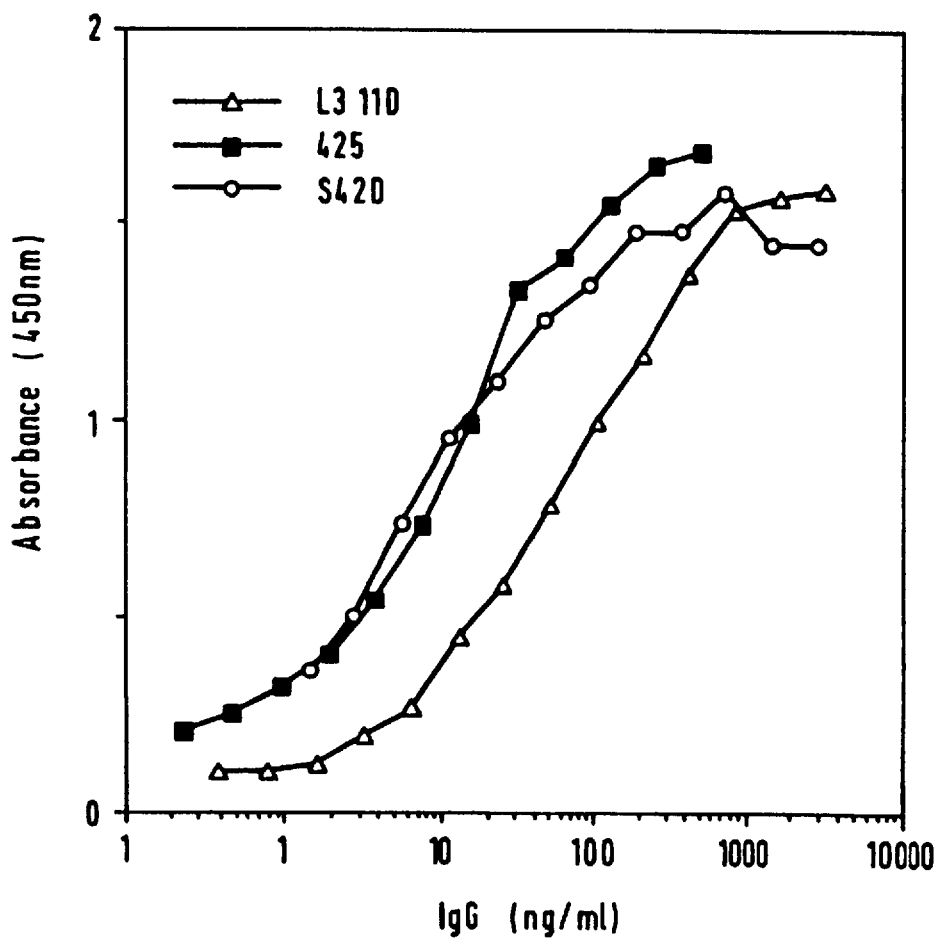
FIG. 4. Binding of chimeric whole antibodies to EGFR. The concentrations of antibodies in COS cell supernatants were determined by ELISA and the antibodies tested by ELISA for binding to purified EGFR.

Two scFvs (L3 11 D and S4 2D) were selected for conversion into whole antibody molecules. DNAs coding for the mouse $V_H$s and $V_K$S were cloned into intermediate vectors containing DNA sequences coding for immunoglobulin leader sequences and splice donor signals (FIG. 3). The positioning of the cloning sites in the $V_H$ intermediate vector meant that the first residue of the $V_H$ was changed from aspartic acid to glutamic acid. From the intermediate vectors, DNA fragments containing the $V_H$s and $V_K$s, now joined to leader and splice donor sequences, were cloned into mammalian cell expression vectors containing DNAs coding for either human gamma-1 constant region or human kappa constant region (Maeda et al., Hum. Antibod. Hybridomas 1991. 2:124). For each chimeric antibody, the heavy chain and light chain expression vectors were co-transfected into COS cells. As a positive control, cells were also co-transfected with heavy and light chain expression vectors coding for chimeric 425 antibody (Kettleborough et al., Protein Eng. 1991. 4:773). Medium was collected from the cells and analyzed by ELISA to determine the concentration of antibody present and the ability of the antibody to bind to EGFR (FIG. 4). When the antibody concentration required to achieve half-maximum binding to antigen were compared, chimeric S4 2D antibody bound to EGFR equally as well as chimeric 425 antibody. Chimeric L3 11 D antibody, however, bound to EGFR approximately four-fold less well than chimeric 425 antibody. The affinity of chimeric 425 antibody (Kettleborough et al, Protein Eng. 1991. 4: 773) has been determined by competition binding analysis to be $1.9 \times 10^8 M^{-1}$. These results were surprising because previous data analyzing the scFvs had indicated that scFvs S4 2D and L3 11D both bound to EGFR better than scFv 425 (FIG. 2). Protein A-purified samples of chimeric L3 11 D and S4 2D antibodies were analyzed by SDS-PAGE under reducing and non-reducing conditions. Chimeric L3 11 D and S4 2D antibodies were also tested by flow cytometry for binding to A431 and SK-MEL-23 cells. Both chimeric antibodies bound well to the EGFR-expressing A431 cells and did not bind to the EGFR-negative SK-MEL-23 cells.

(5) Therapeutic and diagnostic use

The antibody fragments and whole antibodies according to the invention can be administered to human patients for therapy. Therefore, it is an object of the invention to provide a pharmaceutical formulation comprising as active ingredient at least one antibody or antibody fragment as defined above and in the claims, associated with one or more pharmaceutically acceptable carrier, excipient or diluent therefore.

Typically the antibody of this invention will be injected intravenously or parenterally. Generally, the dosage ranges for the administration of the antibodies fragments are large enough to produce the desired tumor suppressing and tumor lysing effect. The dosage will depend on age, condition, sex and extent of the disease in the patient and can vary from 0.1 mg/kg to 200 mg/kg, preferably from 0.1 mg/kg to 100 mg/kg/dose in one or more doses administered daily, for one or several days.

Preparations for parenteral administration includes sterile aqueous or non-aqueous solutions, suspensions, and emulsions. Examples of non-aqueous solvents are propylene glycol, polyethylene glycol, vegetable oils such as olive oils, and injectable organic esters such as ethyl oleate and other solvents known in the art which are suitable for these purposes. The antibodies of this invention can be used in a composition comprising a physiologically acceptable carrier. Examples of such suitable carriers are saline, PBS, Ringer's solution, or lactated Ringer's solution. Preservatives and other additives such as antibiotics, antioxidants, and chelating agents may also be present in the pharmaceutical formulations.

The antibody (fragment) can also be conjugated according to known methods to cytokines such as IL-2 in order to support their cytotoxicity.

The pharmaceutical formulations of the present invention are suitable for the treatment of all kinds of tumors, including melanomas, gliomas and carcinomas, as well as tumors of the circulating system and solid tumors.

For diagnostic purposes the antibody can be conjugated, for example, to a radio-opaque dye or can be radiolabelled. A preferred labelling method is the Iodogen method. Preferably the antibody will be administered as $F(ab')_2$ or scFv fragments for diagnostic purposes. This provides superior results so that backround substraction is unnecessary.

EXAMPLE 1

A431 vesicles

Shed membrane vesicle preparations were obtained as previously described by (Cohen et al., J. Biol. Chem. 1982. 257:1523; Yeaton et al., J. Biol. Chem. 1983. 258: 9254) with some modifications. Confluent flasks containing A431 cells were washed with PBS containing calcium and magnesium. Hypotonic PBS was added and flasks were shaken for 15 minutes. Cells were then washed with vesiculation buffer (100 mM NaCl, 50 mM $Na_2HPO_4$, 5 mM KCl, 0.5 mM $MgSO_2$, pH 8.5). Vesiculation buffer was added and flasks were kept in agitation at room temperature and at 37° C. Then, buffer was decanted through metallic screen into 50 ml tubes in ice and centrifuged for 5 minutes at 150×g at 4° C. The pellet was discarded and the supernatant was ultracentrifuged at 39,000 rpm for 90 minutes. The final pellets were resuspended in 10 mM Hepes buffer (pH 7.4). To analyze EGFR from vesicles, samples were precipitated with 9 volumes of ethanol resuspended with 0.08M Tris, pH 6.8, and then SDS-PAGE was carried out with MAb 425 as standard.

The protein content of the preparations was quantitated by a modified Coomassie Plus method using BSA as a standard and read at 595 nm. To analyze EGFR from vesicles, samples were precipitated with 9 volumes of ethanol (overnight at 4° C.). The pellet was resuspended with Tris (0.08M, pH 6.8) and then a SDS-PAGE was run (5% stacking gel; 1 h, 35 mA; 10% running gel; 2.5 h; 40 mA). Samples and standard were in duplicate. One of them was stained with Coomassie Blue and the other was blotted onto nitrocellulose sheets (12 V; 16 h at 4° C.) and treated with mouse mAb 425 (anti-EGFR) and anti-mouse IgG antibody conjugated to alkaline phosphatase.

Three media were used in the in vitro immunizations. Medium-1 (M1), Medium-2 (M2) and Mixed Thymocyte Culture medium (MTC). M1 consisted of HL1 (Ventrex Laboratories, USA) supplemented with 50 mM 2-mercaptoethanol and 2 mM L-Glutamine (Gibco). M2 consisted of HL1 supplemented with 50 mM 2-mercaptoethanol; 40 U/ml IL-2 (Genzyme); 20 mg/ml Adjuvant Peptide (Sigma); 2 mM L-glutamine; 100 U/ml penicillin (Gibco); 100 mg/ml streptomycin (Gibco). 4% or 20% of FCS (Biological Industries) was added to M2. MTC was prepared as described by Vaux (1). Briefly single cell suspensions of thymuses of three-week-old Balbic and C57/BL-1 mice were prepared by pressing the thymus glands through a sterile 50-mesh screen. The cell suspension was collected, washed twice in HBSS and the number of viable cells was determined by trypan blue exclusion. Thymocytes were then cultured at a density of $2.5 \times 10^6$ thymocytes of each strain per ml in HL1 medium containing 4% FCS, 2 mM L-glutamine, 100 U/ml penicillin and 100 mg/ml streptomycin. After 48 hours, the supernatant was recovered, filtered through a 0.22 mm filter, and stored at -70° C.

A suspension of splenocytes from non-immunized eight-week old BALB/c mice was obtained as described for thymocytes. Viability was determined by trypan blue exclusion.

EXAMPLE 2

In vitro immunization and screening

Three media were used in the in vitro immunizations. Medium-1 (M1), Medium-2 (M2) and Mixed Thymocyte Culture medium (MTC). M1 consisted of HL1 (Ventrex Laboratories, USA) supplemented with 50 mM 2-mercaptoethanol and 2 mM L-Glutamine (Gibco). M2 consisted of HL1 supplemented with 50 mM 2-mercaptoethanol; 40 U/ml IL-2 (Genzyme); 20 mg/ml Adjuvant Peptide (Sigma); 2 mM L-glutamine; 100 U/ml penicillin (Gibco); 100 mg/ml streptomycin (Gibco). 4% or 20% of FCS (Biological Industries) was added to M2. MTC was prepared as described by Vaux (1). Briefly single cell suspensions of thymuses of three-week-old Balbic and C57/BL-1 mice were prepared by pressing the thymus glands through a sterile 50-mesh screen. The cell suspension was collected, washed twice in HBSS and the number of viable cells was determined by trypan blue exclusion. Thymocytes were then cultured at a density of $2.5 \times 10^6$ thymocytes of each strain per ml in HL1 medium containing 4% FCS, 2 mM L-glutamine, 100 U/ml penicillin and 100 mg/ml streptomycin. After 48 hours, the supernatant was recovered, filtered through a 0.22 mm filter, and stored at -70° C.

A suspension of splenocytes from non-immunized eight-week old BALB/c mice was obtained as described for thymocytes. Viability was determined by trypan blue exclusion.

Single cell suspensions from thymuses of three-week-old Balb/c and C57/BL-1 mice were obtained by pressing the thymus glands through a sterile 50-mesh screen. The cell suspension was collected, washed with HBSS and the number of viable cells was determined by trypan blue exclusion. Thymocytes were then cultured at a density of $2.5 \times 10^6$ thymocytes of each strain per ml in HL1-medium containing 4% FCS, 2 mM L-glutamine, 100 U/ml penicillin and 100 µg/ml streptomycin. After 48 hours the supernatant was recovered, filtered and stored. A suspension of splenocytes from non-immunized eight-week-old BALB/c mice was obtained as described for thymocytes. Viability was determined by trypan blue exclusion.

In vitro immunizations were performed in 6-well plates (Costar). Wells containing $10^7$ splenocytes in 3.5 ml of M1-medium (consisting of HL1-medium, Ventrex Laboratories, USA, supplemented with 50 µM 2-mercaptoethanol and 2 mM L-glutamine (Gibco)) were incubated (37° C., 5% $CO_2$) with vesicles bearing EGFR at the desired concentration. Vesicles from cells not expressing EGFR or PBS were added in control wells. After some hours, 3.5 ml of M2-medium (consisting of HL1 supplemented with 50 µM 2-mercaptoethanol, 40 U/ml IL-2 (Genzyme), 20 µg/ml adjuvant peptide (SIGMA), 2 mM L-glutamine, 100 U/ml penicillin (Gibco), 100 µg/ml streptomycin (Gibco)) containing 4% or 10% FCS (Biological Industries) was added to each well. In some experiments M2 was replaced by MTC-medium (mixed thymocyte culture medium (Vaux et al., Nature 1988. 336: 36) supplemented with adjuvant peptide (20µg/ml) and IL-2 (40 U/ml) (Note that the final concentration of FCS, IL2 and adjuvant peptide in culture is 50% reduced). Cells were incubated for 72, 96, 120 or 144 h in the same conditions and, finally, the cells were tested for the presence of specific immunoglobulin or processed for RNA isolation.

Screening was carried out with purified antigens or A431 fixed cells. The procedure was essentially as previously described (Carroll et al., Hybridoma 1990. 9: 81) with some modifications. Briefly, sterile 96-well plates (Nunc, Maxisorb) were coated overnight with purified EGFR (2.5 µg/ml), $GD_3$ ganglioside (2 µg/ml), or RNase (10 µg/ml) in PBS. When A431 cells were used as antigen, cells were cultured in 96-well plates until confluent and fixed with 0.1 % glutaraldehyde. In vitro immunized lymphocytes were washed and resuspended in HL1 medium supplemented with 2 % FCS and 2 mM of L-glutamine at $5 \times 10^5$ cells/ml and $1 \times 10^5$ cells were added to each well and incubated (37° C., 5% $CO_2$) for 48 h. Sixteen duplicates of each group were done. Lymphocytes were then removed by washing 5 times in PBS containing 0.1 % Tween-20. Specific immunoglobulins were detected using peroxidase labelled rabbit anti-mouse immunoglobulin (Dako) (1 hour, 37° C.). 2,2'-Azino-bis(3-ethylbenz-thiazoline-6-sulfonicacid)-diammonium salt (ABTS) (Sigma) in citrate-phosphate buffer (0.55 mg/ml) was used as substrate.

EXAMPLE 3

Library construction

Three libraries were constructed from RNA prepared from the spleen of a mouse immunized intraperitoneally with A431 cells (Murthy et al., Arch. Biochem. Biophys. 1987. 252: 549) from the popliteal lymph node of a mouse immunized in the footpad with purified EGFR, and from mouse cells immunized in vitro with A431 vesicles. First-strand cDNA was synthesized. The $V_H$ and $V_K$ genes were PCR-amplified and assembled (Clackson et al., Nature 1991. 352: 624). Using PCR, Notl and Sfil restriction sites were appended and the scFvs cloned into the phagemid vector pHEN1 (Hoogenboom et al., Nucl. Acids Res. 1991.19:4133). The ligation mixtures were electroporated into E. coli cells and the resulting colonies scraped into medium to generate library stocks (Marks et al., J. Mol. Biol. 1991. 222: 581).

EXAMPLE 4

Library screening

Phage antibodies were rescued from the libraries using M13K07 helper phage (Promega, Madison, Wis.) (Marks et al., J. Mol. Biol. 1991. 222:581). Immunotubes (Nunc, Life Sciences, Paisley, UK) were coated with 4 ml of 2.5 µg/ml EGFR in PBS overnight. After three washes with PBS, tubes were incubated at 37° C. for at least 1 h in PBS containing 2% milk powder (PBSM). The phage ($10^{12}$ to $10^{13}$) were resuspended in 4 ml PBSM and incubated in the EGFR-coated tube for 1 h at room temperature. The tube was washed 20 times with PBS, 0.1% Tween and 20 times with PBS. Bound phage were eluted after a 10 min incubation in 1 ml of 0.1M triethylamine with end-over-end mixing. The eluted phage were neutralized by the addition of 0.5 ml of 1M Tris-HCl, pH 7.5 and used to infect log-phase E. coli TG1 cells. Infected cells were plated and individual colonies picked for small-scale induction of scFvs. The remaining colonies were scraped into medium and an aliquot used to prepare phage for the next round of screening.

EXAMPLE 5

Production and analysis of scFvs

Soluble scFvs were produced in *E. coli* HB2151 as previously described (e.g. Kettleborough et al., I. c.). The scFv concentrations in the bacterial supernatants were estimated using a purified scFv preparation of known concentration as a standard. Supernatants were filtered and sodium azide added to 0.1%. Serial dilutions of the supernatants and of the standard were spotted onto immobilon-PVDF filters (Millipore, Watford, UK) using a 96-well manifold. The filters were treated as for a Western blot (Towbin et al., *Proc. Natl. Acad. Sci. USA* 1979. 76: 4350). The scFvs were detected using an antibody (9E10) directed against the C-terminal tag (Munro and Pelham, *Cell* 1986. 46. 291) followed by a peroxidase-conjugated goat anti-mouse IgG and IgM antibody (Jackson ImmunoResearch Lab Inc., West Grove, Pa.). The reactions were developed using the ECL system (Amersham, Aylesbury, UK). Pre-flashed autoradiographs were scanned using a densitometer. A standard curve was prepared and used to estimate the scFv concentrations in the supernatants.

Antigen-binding ELISAs were carried out with EGFR-coated plates (2.5 $\mu$g/ml). Supernatants containing scFvs were diluted in PBSM and added to the plates. Bound scFvs were detected using 9E10 antibody as described above. Supernatants were also tested for binding to a panel of unrelated proteins and plastic. ELISA plates were coated overnight at 100 $\mu$g/ml with ovalbumin, hen egg lysozyme, cytochrome c, glyceraldehyde 3-phosphate dehydrogenase, murine albumin (CBA strain), and BSA. Undiluted supernatants containing 2% milk powder were added in duplicate to the coated plates and bound scFvs detected as described above.

Cell-binding ELISAs were carried out using tumor cell lines, A431 (ATCC CRL 1555), MDA MB 468 (ATCC HTB 132), and SK-MEL-23 (negative control). Cells were grown to confluency in poly-D-lysine-treated 96 well tissue culture trays (Nunc). Cells were washed with DMEM and blocked at 37° C. for 2 h with PBS containing 2.5% BSA. After aspiration, supernatants were added to each well together with an equal volume of 2xYT media containing 4% milk powder and incubated at 40C for 1 h. Bound scFvs were detected as described above.

A competition-based ELISA was carried out by pre-incubating EGFR-coated ELISA plates with 50 $\mu$l of purified scFv (100 $\mu$g/ml) for 10 min. Mouse MAb 425 (50 $\mu$l) was then added to give concentrations of 3.13 to 200 ng/ml. Following incubation and washing, bound mouse MAb 425 was detected using peroxidase-conjugated goat anti-mouse IgG and IgM antibody.

EXAMPLE 6

DNA analysis

For BstNI fingerprinting, the scFv inserts from individual clones were amplified by PCR and the products digested with BstNI (Clackson et al., *Nature* 1991. 352:624). DNA was sequenced using a Sequenase kit (United States Biochemical, Cleveland, Ohio).

EXAMPLE 7

Purification of scFvs

Bacterial supernatants were clarified by centrifugation and filtration through 0.2 $\mu$m filters before loading onto a 1 ml column of purified EGFR (5 mg) coupled to cyanogen bromide-activated Sepharose 4B (Pharmacia, Uppsala, Sweden). The column was washed with 30 ml of PBS followed by 5 ml 0.2M glycine, pH 5.0. The scFvs were eluted with 0.2M glycine/HCl, pH 2.8. The eluate was neutralized with 10xPBS. Protein-containing fractions were pooled and the buffer changed by ultrafiltration (Amicon, Stonehouse, UK) to PBS containing 1 % BSA and 0.05% sodium azide.

EXAMPLE 8

FACS analysis of purified scFvs

A431 cells were trypsinized and incubated in DMEM containing 10% FCS. Cells were washed twice with cold DMEM and filtered through a 45 $\mu$m screen. Cells ($10^6$) were incubated on ice for 30 min in 50 $\mu$l PBS, 1% BSA, with purified scFvs. After two washes with cold PBS, bound scFvs were detected using 50 $\mu$l FITC-conjugated 9E10 antibody (100 $\mu$g/ml). After 30 min on ice, cells were washed once with PBS, fixed in PBS containing 1% formaldehyde, and analyzed using a FACSCAN (Becton-Dickinson, Cowley, UK).

EXAMPLE 9

Construction, analysis and expression of whole chimeric antibodies

Using PstI and BstEII sites, DNAs coding for the VHs of the selected scFvs were subcloned into an intermediate VH vector containing a eukaryotic leader sequence derived from human antibody HG3 CL (Rechavi et al., *Proc. Natl. Acad. Sci. USA* 1983. 80: 855) and a splice donor site (FIG. 3). The DNAs coding for the $V_k$S were adapted for insertion into an intermediate $V_k$ vector using PCR primers to incorporate XhoI and SstI sites at the 5'- and 3'- ends (VkFor: 5'-CCG TTT CAG CTC GAG CTT GGT CCC-3' (SEQ ID NO:29) VkBack: 5'-GAC ATT GAG CTC ACC CAG TCT CCA-3' (SEQ ID NO:30)). The SstI-XhoI fragments were cloned into the intermediate $V_k$ vector containing a eukaryotic leader sequence derived from reshaped human CAMPATH-1 light chain (Riechmann et al., *Nature* 1988. 332: 21) and a splice donor site (FIG. 3). The DNAs coding for the variable regions plus eukaryotic flanking regions were cloned as HindIII-BamHI fragments into mammalian cell expression vectors containing genomic DNAs coding for human gamma-1 constant region or human kappa constant region (Maeda et al., *Hum. Antibod. Hybridomas* 1991. 2: 124). The heavy and light chain expression vectors were electroporated into COS cells. After 72 h, medium was collected and the chimeric anti-EGFR antibodies analyzed by ELISA (Kettleborough et al., *Protein Eng.* 1991. 4: 773).

EXAMPLE 10

Production of sc Fvs derived from in vitro Immunized cells.

The methods disclosed below are slight modifications of the methods described above. Immunization, library construction and screening are given in Examples 1–4. The following steps are described in detail below:

After screening the primary library and the clones derived from the three rounds of panning, some single ampicillin-resistant colonies were selected. Phagemid DNA was prepared by alkaline lysis and used to transfect *E. coli* HB2151, a non-supressor strain, by heat shock. Colonies were inoculated into 2xTY-Amp-Glu and grown overnight at 30° C. A 5 ml aliquot was used to inoculate 50 ml of 2xTY broth containing 100 mg ampicillin/ml and 0.1% glucose and grown with shaking at 30° C. for 1 h (until log-phase). Cells were harvested and expression of soluble scFv was induced by the addition of isopropyl $\beta$-D-thiogalactopyranoside (IPTG) to a final concentration of 1 mM (De Bellis, D. and Schwartz, I.; *Nucleic Acids Res.*; 1990.18: 131 1). Cultures were grown overnight at 30° C. with shaking. Supernatants containing scFv were taken, clarified by centrifugation and filtration through 0.22 mm filters and tested. Bacterial supernatants were tested for binding to EGFR by ELISA, as described (Keftleborough, et al., EP 94104160 and Eur. J. Immunol. 1994. 24: 952). The specificity of selected scFv fragments was checked by ELISA using plates coated with various proteins related and non-related to EGFR, as well as other antigens and plastic. The antigens used were: RNase, BSA, OVA, $GD_3$ ganglioside, vitronectin receptor (VNR), platelet glycoprotein IIbIIIa (GPIIbIIIa), and disialyl-lacto-N-tetraose (DSLNT). Coating was done overnight at the optimum concentration for each antigen. Coated ELISA plates were blocked for 1 h at 37° C. with 1.5% skimmed milk in PBS (w/v). After washing, 100 ml of scFv supernatants were added to the microtiter wells and incubated for 2 h at 37° C. Bound scFv were detected using the anti-c-myc antibody 9E10 (spent culture media from Myc 1-9E10.2 hybrid) and an alkaline phosphatase-conjugated rabbit antimouse antibody (Dako).

Three EGFR-bearing tumor cell lines, A431, MDA MB 231 human breast adenocarcinoma (ATCC, HTB 26), and HT29 human colon adenocarcinoma (ATCC, HTB 38), and one non-expressing EGFR cell line, WM164, were used to test the ability of scFv to bind to EGFR on cells by mean FACS analysis and immunofluorescence with unfixed cells. For the indirect immunofluorescence analysis, cells were plated into Terasaki plates ($2 \times 10^4$ cells/well) and cultured for 24 h. Cells were then incubated with 20 ml of crude bacterial supernatant containing the scFv fragments for 90 min at room temperature. Incubations with primary antibody (anti-c-myc) and secondary antibody were carried out for 60 min at room temperature. The secondary antibody, FICT-conjugated rabbit anti-mouse antibody (Dako) was diluted 1:20.

For FACS analysis, $5 \times 10^5$ cells were washed with PBS with 1% BSA and 0.1 % sodium azide (PBS-BSA) and incubated at 4° C. for 20 min with 50 ml of crude bacterial supernatant. After two washes with cold PBS-BSA, bound scFv was detected using anti-c-myc antibody and FITC-conjugated goat anti-mouse antibody (Becton-Dickinson) diluted 1:25 in PBS-BSA. Propidium iodide (PI) was added at a final concentration of 5 mg/ml. Flow cytometry analysis were performed in a EPICS Profile II equipped with an air-cooled argon laser. The 488 nm line (15 mV) was used for the excitation. A 530 nm band pass filter was used to collect FITC emission and a 625 nm band pass filter was used to collect PI emission. Living cells were selected by setting a bitmap on forward and side scatter and by exclusion of PI-stained cells.

The diversity of the primary and selected libraries was determined by PCR amplification of cloned fragments (Gussow, D. Clackson, T.; Nucleic Acids Res. 1989.17: 4000) and analysis of the BstNI digestion pattern (8). Some clones were sequenced using a Sequenase kit (USB) by the dideoxy chain termination method (Sanger, F et al.; Proc. Nat.Acad. Sci., U.S.A. 1977.74: 5463).

Crude bacterial supernatants (10 ml) were subjected to SDS-PAGE using a 12.5% gel. Western blotting was performed essentially as described by Towbin (Towbin et al. J. Proc.Nat.Acad.Sci., U.S.A 1979. 76: 4350). Proteins were transferred by electroblotting to Immobilon-P (Millipore) or nitrocellulose (Bio-Rad). The blot was blocked with PBS containing 2% skimmed milk (w/v). scFv fragments were detected using anti-c-myc antibody (9E10), peroxidase-conjugated anti-mouse antibody (Jackson), and an enhanced chemiluminiscence system (ECL, Amersham).

The quantitative analysis of the shed membrane vesicles revealed a total protein concentration of 2.5 mg/ml, of which only 10–14% corresponded to EGFR (Sato et al.; J. Natl. Cancer Inst. 1989. 21: 1601; Yeaton, R et al., J. Biol. Chem., 1983. 258: 9254), 250 to 350 ng/ml. Electrophoretic analysis using PAGE-SDS followed by Coomassie-blue staining showed that the vesicles contained a rather complex mixture of proteins. No protein degradation was detected. Western blot analysis revealed that under our experimental conditions complete molecules of EGF receptor were present in the membrane vesicle preparation.

In order to determine the requirements for FCS and limphokines MTC and M2 containing 20% or 4% FCS were compared. Vesicles bearing EGFR and PBS were used as antigen and control respectively. Splenocytes were incubated in six well plates with or without antigen for 3 h in M1 (serum-free). MTC or M2 was then added and, after 72, 96, 120 or 144 h, screening was carried out using A431 fixed cells. In all experiments, the number of viable cells recovered was between 20 and 40% in agreement with published results (Gavilondo-Cowley, J. et al.; In Vitro Immunization in Hybridoma Technology, Elsevier Science Publishers B.V., Amsterdam 1988, p. 131). The maximum specific response was obtained on day four with MTC; whereas, M2 at 4% or 20% FCS (2% or 10% final concentration) delayed the maximum response until day six (Table 2). However MTC and 10% FCS triggered a non-specific response, probably by polyclonal activation, as could be seen when the results were expressed as the ratio of specific/non-specific response. For further assays we decide to use M2 supplemented with 4% FCS and 6 d of culture.

The presence of EGFR in the suface of vesicles strongly enhanced the response to this antigen. In similar protocols as described above, vesicles from expressing and non-expressing EGFR cell lines were compared. Lymphocytes were cultured with vesicles in Ml for 3 h. Afterwards M2 containing 4% FCS was added. After 6 d, lymphocytes from each group were cultured for 48 h in 96 well plates coated with EGFR, A431-fixed cells, RNase or GD3. As expected, the results of these assays showed a multispecific pattern of response (Table 3). The reactivity against EGFR was clearly increased in terms of optical density when EGFR-expressing vesicles were used as antigen.

Taken together, these results suggest that, although immature, there was a measurable antigen-dependent response after in vitro immunization which generated several pools of immunized lymphocytes against EGFR suitable for PCR-cloning of variable regions.

A library of $1.1 \times 10^5$ clones was obtained after cloning scFv fragments derived from in vitro immunization into the pHEN1 phagemid. This library was generated in parallel with two more libraries providing of in vivo immunization. The construction of these phages libraries has been described previously (Kettleborough, et al., EP 94104160 and Eur. J. Immunol. 1994.24: 952).

To select the scFv fragments binding to EGFR, phage were panned using EGFR-coated immunotubes. Eluted phage were used to reinfect a SupE strain of E. coli. In total, three rounds of selection were carried out. In each round, a tube without antigen was tested in paralel to calculate the background. In the first panning, $1.5 \times 10^{10}$ phage particles were applied to the immunotube and $6.6 \times 10^4$ were eluted from the coated immunotube; whereas, only 200 colonies were obtained from the background population. After the third panning, $1 \times 10^{11}$ phages were applied and $5.6 \times 10^{10}$ were eluted.

To further characterize the scFv fragments, we selected 22 clones from the phage populations, before selection and after each round of selection.

The diversity of the library was analyzed by the BstNI digestion patterns of the cloned fragments. Prior to selection the library appeared to be extremely diverse. Fingerprinting of binding clones derived after the first round of selection indicated the presence of several groups with the same restriction pattern.

Clones were selected from different rounds of selection based on their digestion patterns. DNA sequencing revealed the presence of different sequences in most of the selected clones. The length and composition of complementarity determining regions (CDRs) of clones 10 D2, 5D3, 10 E2, 1 B3, 4B3 and 5E2 were different. The most variation was observed in the CDR3s of $V_H$ and $V_L$ sequences. Clones 5D3 and 1 E3 were derived from the third round of selection. They bound strongly to EGFR as analyzed by ELISA and flow cytometry and had the same sequence.

Soluble scFv fragments were obtained by growth of the non-suppressor E. coli strain HB 2151 in presence of IPTG.

To verify scFv production, bacterial medium from individual clones, was analyzed by gel electrophoresis. Western blot analysis revealed a clear band around 35,000 kD.

Clones with binding activities to EGFR were identified by ELISA. To examine the cross-reactivity of selected clones, ELISA assays using different antigens were carried out. The antigens (EGFR, RNase, BSA, KLH, OVA, $GD_3$ ganglioside, vitronectin receptor, platelet glycoprotein IIbIIIa, and disialyl-lacto-N-tetraose) were coated into ELISA plates at the optimum concentration (Table 4). No binding to non-EGFR antigens was detected. The scFvs were also tested for binding to three EGFR-bearing tumor cell lines (human epidermoid carcinoma A431, human breast adenocarcionma MDA MB 231 and human colon adenocarcinoma HT 29). WM 164 a human melanoma non-expressing EGFR was used as a negative control. Those that bound to tumor cell lines was tested by indirect immunofluorescence using unfixed cells and quantified by FACS analysis. The use of unfixed cells ensures the natural conformation of the membrane receptors. Positive clones showed a clear fluorescence using A431 cells. Fluorescence with the others EGFR-bearing tumor cell lines was weak. No binding to the negative cell line was detected. The results were confirmed by flow cytometry. Seventeen positive clones and three negative clones were analyzed for binding to A431, MDA MB 231 and HT 29 cells by flow cytometry. WM 164 was used as the negative cell line. The 425 scFv (P1 clone) was used as a positive control and the cloning vector (HEN) as a negative control. The results are summarized in Table 5. Two clones, 4B2 and 5E2, were positive for binding to EGFR, as analyzed by ELISA, but negative for binding to EGFR-expressing tumor cell lines.

TABLE 2

Effect of different media on in vitro immunization.[a]

| | | Day of screening against of A431 | | | | | | | |
|---|---|---|---|---|---|---|---|---|---|
| | | 3th day | | 4th day | | 5th day | | 6th day | |
| Assay | Antigen | O.D.[c] | Ratio[d] | O.D. | Ratio | O.D. | Ratio | O.D. | Ratio |
| 1 | Vesicles | 0.393 | 2.11 | 0.801 | 3.76 | 0.784 | 3.90 | 0.951 | 10.3 |
|   | PBS | 0.186 |  | 0.213 |  | 0.201 |  | 0.092 |  |
| 2 | Vesicles | 0.527 | 2.50 | 0.852 | 1.76 | 0.863 | 2.75 | 1.168 | 3.94 |
|   | PBS | 0.210 |  | 0.482 |  | 0.313 |  | 0.296 |  |
| 3 | Vesicles | 0.763 | 1.48 | 1.169 | 2.01 | 1.089 | 2.07 | 1.115 | 1.91 |
|   | PBS | 0.513 |  | 0.581 |  | 0.525 |  | 0.581 |  |

Assay 1: M1 plus M2, 4% FCS (Final FCS: 2%)
Assay 2: M1 plus M2, 20% FCS (Final FCS: 10%)
Assay 3: A-medium plus MTC, 4% FCS (Final FCS: 2%)
[a]BALB/c mouse spleen cells ($10^7$) were incubated in 3.5 ml of M1 with vesicles from A431 cells or PBS for 3 h in wells of 6 well plates. Afterwards 3.5 ml of MTC or M2 containing 4% or 20% FCS were added and the plates incubated. At 3, 4, 5 or 6 days in vitro immunized lymphocytes were removed from culture medium, washed in HBSS to remove vesicles and seeded in 96 well plates coated with fixed A431 cells, and incubated for 48 h (see Methods).
[b]Final concentration of FCS in culture medium.
[c]O.D. Optical densitiy read at 405 nm. It represents the mean of sixteen wells.
[d]Ratio of specific response (vesicles as antigen)/unspecific response (PBS as antigen).

TABLE 3

Multi-specificity of the response after in vitro immunization[a]

| Antigen group | Screening against | | | |
|---|---|---|---|---|
| | A431 CELLS | EGFR | GD3 | RNase |
| Assay 1 EGFR+ | 0.512[b] | 0.326 | 0.140 | 0.249 |
| EGFR− | 0.427 | 0.070 | 0.123 | 0.304 |
| Assay 2 EGFR+ | 1.430 | 0.730 | 0.233 | 0.670 |
| EGFR− | 0.789 | 0.195 | 0.118 | 0.561 |

[a]Lymphocytes were in vitro immunized using either EGFR-expressing vesicles (EGFR+) or non-EGFR expressing vesicles (EGFR−). After six days of incubation, cells were removed from culture and screened against the above mentioned antigens.
[b]Response is expressed as optical density (405 nm).

TABLE 4

Cross-reactivity of selected scFv fragments against several antigens[a]

| ANTIGEN[b] | COATING [mg/ml] | RESULT |
|---|---|---|
| EGFR | 2.5 | + |
| RNase | 10 | − |
| BSA | 10 | − |
| KLH | 10 | − |
| OVA | 10 | − |
| $GD_3$ ganglioside | 2 | − |
| VNR | 1 | − |
| GPIIbIIIa | 1 | − |
| DSLNT | 5 | − |

[a]ELISA assays were performed as described.
[b]Vitronectin receptor (VNR); platelet glycoprotein IIbIIIa (GPIIbIIIa); disialyl-lacto-N-tetraose (DSLNT).

TABLE 5

Reactivity of scFv clones against EGFR.
Comparative results between an ELISA method with purified soluble antigen and cytometric analysis of cell lines.

| CLONES | CYTOMETRIC ANALYSIS OF TUMOR CELL LINES[a] (mean of arbritary fluorescence units) | | | | ELISA (O.D.) |
|---|---|---|---|---|---|
| | WM164 | A431 | MDAAMB231 | HT29 | EGFR |
| Positive | | | | | |
| 7H1 | 1.5 | 112.9 | 16.4 | 2.6 | 1.2 |
| 4B2 | 1.2 | 5.3 | 4.2 | 0.6 | 2 |
| 10D2 | 1.5 | 145.3 | 36.3 | 4.8 | 2 |
| 12D2 | 1.8 | 129.5 | 29.3 | 5.7 | 2 |
| 5E2 | 1.4 | 2.5 | 7.1 | 0.5 | 1.8 |
| 8E2 | 1.5 | 134.5 | 47.7 | 5.1 | 1.9 |
| 5F2 | 1.3 | 146.3 | 40.6 | 5.7 | 1.9 |
| 11H2 | 1.9 | 152.2 | 25.3 | 2 | 1.9 |
| 1B3 | 0.6 | 105.1 | 36.4 | 5.2 | >2 |
| 4B3 | 0.5 | 78 | 15.8 | 2.3 | 2 |
| 3D3 | 1.2 | 94.3 | 25.1 | 4.8 | 1.9 |
| 5D3 | 0.5 | 112 | 22.2 | 5.5 | >2 |
| 4F3 | 0.4 | 110.3 | 32.3 | 6.2 | >2 |
| 4G3 | 0.4 | 76.5 | 20.4 | 2 | >2 |
| 1E3 | 0.4 | 118.3 | 33.8 | 5.1 | 2 |
| 3H3 | 0.6 | 76.5 | 33.7 | 4.2 | >2 |
| Negative | | | | | |
| 5F1 | 2.4 | 2.3 | 3.6 | 1.8 | 0.2 |
| 7G1 | 1.4 | 10.2 | 4 | 2.8 | 0.2 |
| 1H1 | 0.5 | 5 | 4 | 0.75 | 0.2 |
| Controls[b] | | | | | |
| HEN | 0.4 | 4.1 | 3.7 | 1 | 0.2 |
| P1 | 0.6 | 85.5 | 21.3 | 2.5 | 1.9 |

[a] Three EGFR-bearing cell lines (A431, MDAAMB231 and HT29) and one non-expressing cell line (WM164) were used to assay the ability of scFv to bind to tumor cells lines by cytometric analysis as described.
[b] Vector without fragment (HEN) and scFv fragment from 425 mAb (P1) were used as negative and positive controls, respectively.

We claim:

1. An anti-EGFR single-chain Fv obtainable from a phage-antibody library constructed from cells from an immunized mammal, wherein the variable region of the single chain Fv comprises a heavy chain amino acid sequence selected from the group consisting of SEQ ID NO:4, SEQ ID NO:8, SEQ ID NO:12, SEQ ID NO:16, SEQ ID NO:18, SEQ ID NO:20, SEQ ID NO:22, SEQ ID NO:24, SEQ ID NO:26 and SEQ ID NO:28 and a light chain amino acid sequence selected from the group consisting of SEQ ID NO:2, SEQ ID NO:6, SEQ ID NO:10, SEQ ID NO:14, SEQ ID NO: 18, SEQ ID NO:20, SEQ ID NO:22, SEQ ID NO:24, SEQ ID NO:26 and SEQ ID NO:28.

2. An anti-EGFR single chain FV according to claim 1, wherein said library is constructed from cells of an immunized mouse.

3. An anti-EGFR single chain Fv according to claim 1, wherein said library is constructed from cells of:
   (i) the lymph node,
   (ii) the spleen, or
   (iii) in vitro immunized cells.

4. A DNA molecule encoding a chimeric anti-EGFR antibody comprising DNA sequences encoding heavy chain and light chain variable region amino acid sequences according to claim 1 and a DNA sequence encoding a constant region of a human immunoglobulin.

5. A chimeric anti-EGFR antibody comprising a variable region with heavy and light chain amino acid sequences according to claim 1, a human gamma-1 heavy chain constant region and a human kappa light chain constant region.

6. Process for the preparation of an anti-EGFR single-chain Fv according to claim 1 comprising the following steps:
   (i) isolating RNA from immunized mammalian cells, preferably mouse cells,
   (ii) synthesizing first-strand cDNA,
   (iii) amplifying the $V_H$ and $V_k$ genes in cDNAs from the immunized cells,
   (iv) cloning said genes together with suitable restriction sites into a phagemid vector,
   (v) transforming prokaryotic cells with the ligation mixtures,
   (vi) screening the phage libraries for phage antibodies directed to EGFR using purified EGFR, and
   (vii) producing said single-chain Fv in prokaryotic host cells, preferably E. coli.

7. A process for the preparation of a chimeric anti-EGFR antibody comprising:
   (I) cloning the DNA coding for the heavy and light chain variable regions of an anti-EGFR single chain Fv, said DNA selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21 SEQ ID NO:23, SEQ ID NO:25 and SEQ ID NO:27 into eukaryotic expression vector containing genomic DNA which codes for the constant regions of human immunoglobulins
   (ii) transforming eukaryotic cells with said vector(s), and
   (iii) expressing and isolating said chimeric antibody.

8. Pharmaceutical composition comprising an anti-EGFR singe chain FV according to claim 1.

9. A method of manufacture of a drug directed to tumors or for the diagnostic location and assessment of tumor growth comprising the preparation of the single chain Fv antibody of claim 1.

10. Pharmaceutical composition comprising a chimeric anti-EGFR antibody encoded by the DNA molecule of claim 4.

11. A vector comprising a DNA molecule of claim 4.

12. An expression vector, comprising a DNA molecule of claim 4 operably linked to an expression control sequence.

13. A host cell transformed with a vector of claim 11.

14. A host cell transformed with a vector of claim 12.

15. A method of making a chimeric anti-EGFR antibody, comprising growing a host cell of claim 14 under conditions whereby the DNA molecule encoding a chimeric anti-EGFR antibody is expressed and isolating said antibody.

16. A chimeric anti-EGFR antibody, comprising a single chain FV of claim 1 and a constant region of a human immunoglobulin.

17. A method of treating a tumor, comprising administering to a patient in need of such treatment an effective amount of a chimeric anti-EGFR antibody of claim 16.

18. A method for the diagnostic location and assessment of tumor growth, comprising administering to a patient in need of such diagnostic treatment an effective amount of a chimeric anti-EGFR antibody of claim 16.

19. An anti-EGFR single chain FV according to claim 2, wherein said cells of an immunized mouse are obtained from:

(I) the lymph node, (ii) the spleen, or (iii) in vitro immunized cells.

20. A DNA molecule encoding an anti-EGFR single-chain Fv, comprising a DNA sequence encoding an a single chain FV of claim 1.

21. A DNA molecule of claim 4, wherein the heavy constant chain region comprises a DNA sequence encoding the amino acid sequence of a human gamma-i chain, and the light constant chain region comprises a DNA sequence encoding the amino acid sequence of a human kappa chain.

22. A vector comprising a DNA molecule of claim 20.

23. An expression vector, comprising a DNA molecule of claim 20 operably linked to an expression control sequence.

24. A host cell transformed with a vector of claim 22.

25. A host cell transformed with a vector of claim 23.

26. A method of making an anti-EGFR single chain Fv, comprising growing the host cell of claim 24 under conditions whereby the vector encoding said anti-EGFR single chain Fv is expressed and isolating said single chain Fv antibody.

27. A method of treating a tumor, comprising administering to a patient in need of such treatment an effective amount of an anti-EGFR single-chain Fv of claim 1.

28. A method for the diagnostic location and assessment of tumor growth, comprising administering to a patient in need of such diagnostic treatment an effective amount of an anti-EGFR single-chain Fv of claim 1.

* * * * *

SEQUENCE LISTING ( 1 ) GENERAL INFORMATION:

( i i i ) NUMBER OF SEQUENCES: 30

( 2 ) INFORMATION FOR SEQ ID NO: 1:

( i ) SEQUENCE CHARACTERISTICS:
        ( A ) LENGTH: 327 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: mouse
        ( B ) STRAIN: Balb/c
        ( D ) DEVELOPMENTAL STAGE: adult
        ( F ) TISSUE TYPE: Lymph node ( v i i ) IMMEDIATE SOURCE:
        ( B ) CLONE: L2 11C (light chain)

( i x ) FEATURE:
        ( A ) NAME/KEY: CDS
        ( B ) LOCATION:1..327

( x i ) SEQUENCE DESCRIPTION: SEQ ID NO: 1:

```
GAC  ATT  GAG  CTC  ACC  CAG  TCT  CCA  GCC  TCC  CTG  GCT  GCA  TCT  GTG  GGA      48
Asp  Ile  Glu  Leu  Thr  Gln  Ser  Pro  Ala  Ser  Leu  Ala  Ala  Ser  Val  Gly
 1              5                        10                       15

GAA  ACT  GTC  ACC  ATC  ACA  TGT  CGA  GCA  AGT  GAG  AAC  ATT  TAC  TAT  AGT      96
Glu  Thr  Val  Thr  Ile  Thr  Cys  Arg  Ala  Ser  Glu  Asn  Ile  Tyr  Tyr  Ser
                20                       25                       30

TTA  GCA  TGG  TAT  CAG  CAG  AAG  CAA  GGG  AAA  TCT  CCT  CAG  CTC  CTG  ATC     144
Leu  Ala  Trp  Tyr  Gln  Gln  Lys  Gln  Gly  Lys  Ser  Pro  Gln  Leu  Leu  Ile
           35                       40                       45

TAT  AGT  GCA  AGC  GCC  TTG  GAA  GAT  GGT  GTC  CCA  TCG  AGG  TTC  AGT  GGC     192
Tyr  Ser  Ala  Ser  Ala  Leu  Glu  Asp  Gly  Val  Pro  Ser  Arg  Phe  Ser  Gly
      50                       55                       60

AGT  GGA  TCT  GGG  ACA  CAG  TAT  TCT  TTA  AAG  ATC  AAC  AAC  ATG  CAG  CCT     240
Ser  Gly  Ser  Gly  Thr  Gln  Tyr  Ser  Leu  Lys  Ile  Asn  Asn  Met  Gln  Pro
 65                       70                       75                       80

GAA  GAT  ACC  GCT  ACT  TAC  TTC  TGT  AAA  CAG  ACT  TAT  GAC  GTT  CCG  TGG     288
Glu  Asp  Thr  Ala  Thr  Tyr  Phe  Cys  Lys  Gln  Thr  Tyr  Asp  Val  Pro  Trp
                     85                       90                       95

ACG  TTC  GGT  GGA  GGG  ACC  AAG  CTG  GAA  ATA  AAA  CGG  GCG                     327
Thr  Phe  Gly  Gly  Gly  Thr  Lys  Leu  Glu  Ile  Lys  Arg  Ala
               100                      105
```

( 2 ) INFORMATION FOR SEQ ID NO: 2:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Asp  Ile  Glu  Leu  Thr  Gln  Ser  Pro  Ala  Ser  Leu  Ala  Ala  Ser  Val  Gly
 1              5                        10                       15

Glu  Thr  Val  Thr  Ile  Thr  Cys  Arg  Ala  Ser  Glu  Asn  Ile  Tyr  Tyr  Ser
                20                       25                       30

Leu  Ala  Trp  Tyr  Gln  Gln  Lys  Gln  Gly  Lys  Ser  Pro  Gln  Leu  Leu  Ile
           35                       40                       45

Tyr  Ser  Ala  Ser  Ala  Leu  Glu  Asp  Gly  Val  Pro  Ser  Arg  Phe  Ser  Gly
      50                       55                       60

Ser  Gly  Ser  Gly  Thr  Gln  Tyr  Ser  Leu  Lys  Ile  Asn  Asn  Met  Gln  Pro
 65                       70                       75                       80

Glu  Asp  Thr  Ala  Thr  Tyr  Phe  Cys  Lys  Gln  Thr  Tyr  Asp  Val  Pro  Trp
                     85                       90                       95

Thr  Phe  Gly  Gly  Gly  Thr  Lys  Leu  Glu  Ile  Lys  Arg  Ala
               100                      105
```

( 2 ) INFORMATION FOR SEQ ID NO: 3:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal (v i) ORIGINAL SOURCE:
(A) ORGANISM: mouse
(B) STRAIN: Balb/c
(D) DEVELOPMENTAL STAGE: adult
(F) TISSUE TYPE: Lymph Node (v i i) IMMEDIATE SOURCE:
(B) CLONE: L2 11C (heavy chain)

(i x) FEATURE:
(A) NAME/KEY: CDS
(B) LOCATION:1..357

(x i) SEQUENCE DESCRIPTION: SEQ ID NO: 3:

```
CAG GTG CAA CTG CAG GAG TCA GGG CCT GAG CTG GTG AGG CCT GGG GCT      48
Gln Val Gln Leu Gln Glu Ser Gly Pro Glu Leu Val Arg Pro Gly Ala
110             115                 120                 125

TCA GTG AAG ATG TCC TGC AAG GCT TCA GGC TAT ACC TTC ACT ACC TAC      96
Ser Val Lys Met Ser Cys Lys Ala Ser Gly Tyr Thr Phe Thr Thr Tyr
            130                 135                 140

TGG ATA CAC TGG ATG AAA CAG AGG CCT GGA CAA GGC CTT CAG TGG ATT     144
Trp Ile His Trp Met Lys Gln Arg Pro Gly Gln Gly Leu Gln Trp Ile
            145                 150                 155

GGC ATG ATT GAT CCT TCC AAT AGT GAA ACT AGG TTA AAT CAG AAT TTC     192
Gly Met Ile Asp Pro Ser Asn Ser Glu Thr Arg Leu Asn Gln Asn Phe
            160                 165                 170

AGG GAC AAG GCC ACA TTG AGT GTA GAC AAA TCC TCC AAT AAA GCC TAC     240
Arg Asp Lys Ala Thr Leu Ser Val Asp Lys Ser Ser Asn Lys Ala Tyr
175                 180                 185

ATG CAG CTC AGC AGC CTG ACA TCT GAG GAC TCT GCA ATC TAT TAC TGT     288
Met Gln Leu Ser Ser Leu Thr Ser Glu Asp Ser Ala Ile Tyr Tyr Cys
190                 195                 200                 205

GCA AGA TGG GAC TAC GGT AGT GGC CAC TTT GAC TAC TGG GGC CAA GGG     336
Ala Arg Trp Asp Tyr Gly Ser Gly His Phe Asp Tyr Trp Gly Gln Gly
                210                 215                 220

ACC ACG GTC ACC GTC TCC TCA                                         357
Thr Thr Val Thr Val Ser Ser
                225
```

(2) INFORMATION FOR SEQ ID NO: 4:

(i) SEQUENCE CHARACTERISTICS:
(A) LENGTH: 119 amino acids
(B) TYPE: amino acid
(D) TOPOLOGY: linear (i i) MOLECULE TYPE: protein (x i) SEQUENCE DESCRIPTION: SEQ ID NO: 4:

```
Gln Val Gln Leu Gln Glu Ser Gly Pro Glu Leu Val Arg Pro Gly Ala
1               5                   10                  15

Ser Val Lys Met Ser Cys Lys Ala Ser Gly Tyr Thr Phe Thr Thr Tyr
            20                  25                  30

Trp Ile His Trp Met Lys Gln Arg Pro Gly Gln Gly Leu Gln Trp Ile
            35                  40                  45

Gly Met Ile Asp Pro Ser Asn Ser Glu Thr Arg Leu Asn Gln Asn Phe
        50                  55                  60

Arg Asp Lys Ala Thr Leu Ser Val Asp Lys Ser Ser Asn Lys Ala Tyr
65                  70                  75                  80

Met Gln Leu Ser Ser Leu Thr Ser Glu Asp Ser Ala Ile Tyr Tyr Cys
                85                  90                  95

Ala Arg Trp Asp Tyr Gly Ser Gly His Phe Asp Tyr Trp Gly Gln Gly
                100                 105                 110
```

Thr Thr Val Thr Val Ser Ser
115

( 2 ) INFORMATION FOR SEQ ID NO: 5:

( i ) SEQUENCE CHARACTERISTICS:
      ( A ) LENGTH: 339 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
      ( A ) ORGANISM: mouse
      ( B ) STRAIN: Balb/c
      ( D ) DEVELOPMENTAL STAGE: adult
      ( F ) TISSUE TYPE: Lymph node ( v i i ) IMMEDIATE SOURCE:
      ( B ) CLONE: L2 12B (light chain)

( i x ) FEATURE:
      ( A ) NAME/KEY: CDS
      ( B ) LOCATION:1..339

( x i ) SEQUENCE DESCRIPTION: SEQ ID NO: 5:

```
GAC  ATT  GAG  CTC  ACC  CAG  TCT  CCA  GCT  TCT  TTG  GCT  GTG  TCT  CTA  GGG           48
Asp  Ile  Glu  Leu  Thr  Gln  Ser  Pro  Ala  Ser  Leu  Ala  Val  Ser  Leu  Gly
120            125                      130                      135

CAG  AGG  GCC  ACC  ATC  TCC  TGC  AGA  GCC  AGC  GAA  AGT  GTT  GAT  AAT  TTT           96
Gln  Arg  Ala  Thr  Ile  Ser  Cys  Arg  Ala  Ser  Glu  Ser  Val  Asp  Asn  Phe
               140                      145                      150

GGC  ATT  AGT  TTT  ATG  AAC  TGG  TTC  CAA  CAG  AAA  CCA  GGA  CAG  CCA  CCC          144
Gly  Ile  Ser  Phe  Met  Asn  Trp  Phe  Gln  Gln  Lys  Pro  Gly  Gln  Pro  Pro
          155                      160                      165

AAA  CTC  CTC  ATC  TAT  GGT  GCA  TCC  AAC  CAA  GGA  TCC  GGG  GTC  CCT  GCC          192
Lys  Leu  Leu  Ile  Tyr  Gly  Ala  Ser  Asn  Gln  Gly  Ser  Gly  Val  Pro  Ala
     170                      175                      180

AGG  TTT  AGT  GGC  AGT  GGG  TCT  GGG  ACA  GAC  TTC  AGC  CTC  AAC  ATC  CAT          240
Arg  Phe  Ser  Gly  Ser  Gly  Ser  Gly  Thr  Asp  Phe  Ser  Leu  Asn  Ile  His
185                      190                      195

CCT  CTG  GAG  GAG  GAT  GAT  ACT  GCA  ATG  TAT  TTC  TGT  CAG  CAA  AGT  AAG          288
Pro  Leu  Glu  Glu  Asp  Asp  Thr  Ala  Met  Tyr  Phe  Cys  Gln  Gln  Ser  Lys
200                 205                      210                      215

GAG  GTT  CCG  CTC  ACG  TTC  GGT  GCT  GGG  ACC  AAG  CTG  GAA  ATA  AAA  CGG          336
Glu  Val  Pro  Leu  Thr  Phe  Gly  Ala  Gly  Thr  Lys  Leu  Glu  Ile  Lys  Arg
                    220                      225                      230

GCG                                                                                      339
Ala
```

( 2 ) INFORMATION FOR SEQ ID NO: 6:

( i ) SEQUENCE CHARACTERISTICS:
      ( A ) LENGTH: 113 amino acids
      ( B ) TYPE: amino acid
      ( D ) TOPOLOGY: linear ( i i ) MOLECULE TYPE: protein ( x i ) SEQUENCE DESCRIPTION: SEQ ID NO: 6:

Asp Ile Glu Leu Thr Gln Ser Pro Ala Ser Leu Ala Val Ser Leu Gly

|  | 1 |  |  |  | 5 |  |  |  |  | 10 |  |  |  |  | 15 |  |
|---|---|---|---|---|---|---|---|---|---|---|---|---|---|---|---|---|
| Gln | Arg | Ala | Thr | Ile | Ser | Cys | Arg | Ala | Ser | Glu | Ser | Val | Asp | Asn | Phe |
|  |  |  | 20 |  |  |  |  | 25 |  |  |  |  | 30 |  |  |

Gly Ile Ser Phe Met Asn Trp Phe Gln Gln Lys Pro Gly Gln Pro Pro
      35              40                  45

Lys Leu Leu Ile Tyr Gly Ala Ser Asn Gln Gly Ser Gly Val Pro Ala
     50                  55                  60

Arg Phe Ser Gly Ser Gly Ser Gly Thr Asp Phe Ser Leu Asn Ile His
65                  70                  75                      80

Pro Leu Glu Glu Asp Asp Thr Ala Met Tyr Phe Cys Gln Gln Ser Lys
             85                  90                  95

Glu Val Pro Leu Thr Phe Gly Ala Gly Thr Lys Leu Glu Ile Lys Arg
            100                 105                 110

Ala ( 2 ) INFORMATION FOR SEQ ID NO: 7:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: mouse
        ( B ) STRAIN: Balb/c
        ( D ) DEVELOPMENTAL STAGE: adult
        ( F ) TISSUE TYPE: Lymph node ( v i i ) IMMEDIATE SOURCE:
        ( B ) CLONE: L2 12B (heavy chain)

( i x ) FEATURE:
        ( A ) NAME/KEY: CDS
        ( B ) LOCATION:1..357

( x i ) SEQUENCE DESCRIPTION: SEQ ID NO: 7:

```
CAG   GTG   CAG   CTG   CAG   GAG   TCT   GGA   CCT   GAG   CTG   GTG   AAG   CCT   GGG   GCT        48
Gln   Val   Gln   Leu   Gln   Glu   Ser   Gly   Pro   Glu   Leu   Val   Lys   Pro   Gly   Ala
115                     120                         125

TTA   GTG   AAG   ATA   TCC   TGC   AAG   GCT   TCT   GGT   TAC   ACC   TTC   ACC   AGC   TAC        96
Leu   Val   Lys   Ile   Ser   Cys   Lys   Ala   Ser   Gly   Tyr   Thr   Phe   Thr   Ser   Tyr
130                     135                         140                         145

TGG   ATG   CAC   TGG   GTG   AAG   CAG   AGG   CCT   GGA   CAA   GGC   CTT   GAG   TGG   ATC       144
Trp   Met   His   Trp   Val   Lys   Gln   Arg   Pro   Gly   Gln   Gly   Leu   Glu   Trp   Ile
                        150                         155                         160

GGA   GAG   ATT   GAT   CCT   TCT   GAT   AGT   TAT   ACT   AAC   TAC   AAT   CAA   AAG   TTC       192
Gly   Glu   Ile   Asp   Pro   Ser   Asp   Ser   Tyr   Thr   Asn   Tyr   Asn   Gln   Lys   Phe
            165                         170                         175

AAG   GGC   AAG   GCC   ACA   TTG   ACT   GTA   GAC   AAA   TCC   TCC   AAC   ACA   GCC   TAC       240
Lys   Gly   Lys   Ala   Thr   Leu   Thr   Val   Asp   Lys   Ser   Ser   Asn   Thr   Ala   Tyr
            180                         185                         190

ATG   CAG   CTC   AGC   AGC   CTG   ACA   TCT   GAG   GAC   TCT   GCG   GTC   TAT   TAC   TGT       288
Met   Gln   Leu   Ser   Ser   Leu   Thr   Ser   Glu   Asp   Ser   Ala   Val   Tyr   Tyr   Cys
195                         200                         205

GCA   AGA   TCG   GAC   TAC   GGT   AGT   AGC   CAC   TTT   GAC   TAC   TGG   GGC   CAA   GGG       336
Ala   Arg   Ser   Asp   Tyr   Gly   Ser   Ser   His   Phe   Asp   Tyr   Trp   Gly   Gln   Gly
```

```
                                     210                     215                     220                     225
ACC  ACG  GTC  ACC  GTC  TCC  TCA                                                                                            357
Thr  Thr  Val  Thr  Val  Ser  Ser
                    230
```

( 2 ) INFORMATION FOR SEQ ID NO: 8:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

```
Gln  Val  Gln  Leu  Gln  Glu  Ser  Gly  Pro  Glu  Leu  Val  Lys  Pro  Gly  Ala
 1                  5                        10                       15
Leu  Val  Lys  Ile  Ser  Cys  Lys  Ala  Ser  Gly  Tyr  Thr  Phe  Thr  Ser  Tyr
               20                       25                       30
Trp  Met  His  Trp  Val  Lys  Gln  Arg  Pro  Gly  Gln  Gly  Leu  Glu  Trp  Ile
          35                       40                       45
Gly  Glu  Ile  Asp  Pro  Ser  Asp  Ser  Tyr  Thr  Asn  Tyr  Asn  Gln  Lys  Phe
     50                       55                       60
Lys  Gly  Lys  Ala  Thr  Leu  Thr  Val  Asp  Lys  Ser  Ser  Asn  Thr  Ala  Tyr
 65                      70                       75                       80
Met  Gln  Leu  Ser  Ser  Leu  Thr  Ser  Glu  Asp  Ser  Ala  Val  Tyr  Tyr  Cys
                    85                       90                       95
Ala  Arg  Ser  Asp  Tyr  Gly  Ser  Ser  His  Phe  Asp  Tyr  Trp  Gly  Gln  Gly
               100                      105                      110
Thr  Thr  Val  Thr  Val  Ser  Ser
               115
```

( 2 ) INFORMATION FOR SEQ ID NO: 9:

( i ) SEQUENCE CHARACTERISTICS:
        ( A ) LENGTH: 339 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: mouse
        ( B ) STRAIN: Balb/c
        ( D ) DEVELOPMENTAL STAGE: adult
        ( F ) TISSUE TYPE: Lymph node ( v i i ) IMMEDIATE SOURCE:
        ( B ) CLONE: L3 11D (light chain)

( i x ) FEATURE:
        ( A ) NAME/KEY: CDS
        ( B ) LOCATION:1..339

( x i ) SEQUENCE DESCRIPTION: SEQ ID NO: 9:

```
GAC  ATT  GAG  CTC  ACC  CAG  TCT  CCA  GCT  TCT  TTG  GCT  GTG  TCT  CTA  GGG     48
Asp  Ile  Glu  Leu  Thr  Gln  Ser  Pro  Ala  Ser  Leu  Ala  Val  Ser  Leu  Gly
120                      125                      130                      135

CAG  AGG  GCC  ACC  ATC  TCC  TGC  CGA  GCC  AGC  GAA  AGT  GTT  GAT  AAT  TTT     96
Gln  Arg  Ala  Thr  Ile  Ser  Cys  Arg  Ala  Ser  Glu  Ser  Val  Asp  Asn  Phe
```

|     |     |     |     | 140 |     |     |     |     | 145 |     |     |     |     | 150 |     |     |     |
|-----|-----|-----|-----|-----|-----|-----|-----|-----|-----|-----|-----|-----|-----|-----|-----|-----|-----|
| GGC | ATT | AGT | TTT | ATG | AAC | TGG | TTC | CAA | CAG | AAA | CCA | GGA | CAG | CCA | CCC |     | 144 |
| Gly | Ile | Ser | Phe | Met | Asn | Trp | Phe | Gln | Gln | Lys | Pro | Gly | Gln | Pro | Pro |     |     |
|     |     |     | 155 |     |     |     |     | 160 |     |     |     |     | 165 |     |     |     |     |
| AAA | CTC | CTC | ATC | TAT | GGT | GCA | TCC | AAC | CAA | GGA | TCC | GGG | GTC | CCT | GCC |     | 192 |
| Lys | Leu | Leu | Ile | Tyr | Gly | Ala | Ser | Asn | Gln | Gly | Ser | Gly | Val | Pro | Ala |     |     |
|     |     | 170 |     |     |     |     | 175 |     |     |     |     | 180 |     |     |     |     |     |
| AGG | TTT | AGT | GGC | AGT | GGG | TCT | GGG | ACA | GAC | TTC | AGC | CTC | AAC | ATC | CAT |     | 240 |
| Arg | Phe | Ser | Gly | Ser | Gly | Ser | Gly | Thr | Asp | Phe | Ser | Leu | Asn | Ile | His |     |     |
|     | 185 |     |     |     |     | 190 |     |     |     |     | 195 |     |     |     |     |     |     |
| CCT | TTG | GAG | GAG | GAT | GAT | ACT | GCA | ATG | TAT | TTC | TGT | CAG | CAA | AGT | AAG |     | 288 |
| Pro | Leu | Glu | Glu | Asp | Asp | Thr | Ala | Met | Tyr | Phe | Cys | Gln | Gln | Ser | Lys |     |     |
| 200 |     |     |     |     | 205 |     |     |     |     | 210 |     |     |     |     | 215 |     |     |
| GAG | GTT | CCG | CTC | ACG | TTC | GGT | GCT | GGG | ACC | AAG | CTG | GAG | CTG | AAA | CGG |     | 336 |
| Glu | Val | Pro | Leu | Thr | Phe | Gly | Ala | Gly | Thr | Lys | Leu | Glu | Leu | Lys | Arg |     |     |
|     |     |     |     | 220 |     |     |     |     | 225 |     |     |     |     | 230 |     |     |     |
| GCG |     |     |     |     |     |     |     |     |     |     |     |     |     |     |     |     | 339 |
| Ala |     |     |     |     |     |     |     |     |     |     |     |     |     |     |     |     |     |

( 2 ) INFORMATION FOR SEQ ID NO: 10:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 10:

| Asp | Ile | Glu | Leu | Thr | Gln | Ser | Pro | Ala | Ser | Leu | Ala | Val | Ser | Leu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gln | Arg | Ala | Thr | Ile | Ser | Cys | Arg | Ala | Ser | Glu | Ser | Val | Asp | Asn | Phe |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Ile | Ser | Phe | Met | Asn | Trp | Phe | Gln | Gln | Lys | Pro | Gly | Gln | Pro | Pro |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Lys | Leu | Leu | Ile | Tyr | Gly | Ala | Ser | Asn | Gln | Gly | Ser | Gly | Val | Pro | Ala |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Arg | Phe | Ser | Gly | Ser | Gly | Ser | Gly | Thr | Asp | Phe | Ser | Leu | Asn | Ile | His |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Pro | Leu | Glu | Glu | Asp | Asp | Thr | Ala | Met | Tyr | Phe | Cys | Gln | Gln | Ser | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Glu | Val | Pro | Leu | Thr | Phe | Gly | Ala | Gly | Thr | Lys | Leu | Glu | Leu | Lys | Arg |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

Ala ( 2 ) INFORMATION FOR SEQ ID NO: 11:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: mouse
        ( B ) STRAIN: Balb/c ( D ) DEVELOPMENTAL STAGE: adult
( F ) TISSUE TYPE: Lymph node ( v i i ) IMMEDIATE SOURCE:
( B ) CLONE: L3 11D (heavy chain)

( i x ) FEATURE:
( A ) NAME/KEY: CDS
( B ) LOCATION:1..357

( x i ) SEQUENCE DESCRIPTION: SEQ ID NO: 11:

| GAG | GTG | CAG | CTG | CAG | CAG | TCA | GGG | GCT | GAG | CTT | GTG | AAG | CCT | GGG | GCT | 48 |
| Glu | Val | Gln | Leu | Gln | Gln | Ser | Gly | Ala | Glu | Leu | Val | Lys | Pro | Gly | Ala | |
| 115 | | | | | 120 | | | | | 125 | | | | | | |

| TCA | GTG | AAG | CTG | TCC | TGC | AAG | GCT | TCT | GGC | TAC | ACC | TTC | ACC | AGC | TAC | 96 |
| Ser | Val | Lys | Leu | Ser | Cys | Lys | Ala | Ser | Gly | Tyr | Thr | Phe | Thr | Ser | Tyr | |
| 130 | | | | | 135 | | | | | 140 | | | | | 145 | |

| TGG | ATG | CAC | TGG | GTG | AAG | CAG | AGG | CCT | GGA | CAA | GGC | CTT | GAG | TGG | ATC | 144 |
| Trp | Met | His | Trp | Val | Lys | Gln | Arg | Pro | Gly | Gln | Gly | Leu | Glu | Trp | Ile | |
| | | | | 150 | | | | | 155 | | | | | 160 | | |

| GGA | GAG | ATT | GAT | CCT | TCT | GAT | AGT | TAT | ACT | AAC | TAC | AAT | CAA | AAG | TTC | 192 |
| Gly | Glu | Ile | Asp | Pro | Ser | Asp | Ser | Tyr | Thr | Asn | Tyr | Asn | Gln | Lys | Phe | |
| | | | 165 | | | | 170 | | | | | 175 | | | | |

| AAG | GGC | AAG | GCC | ACA | TTG | ACT | GTA | GAC | AAA | TCC | TCC | AGC | ACA | GCC | TAC | 240 |
| Lys | Gly | Lys | Ala | Thr | Leu | Thr | Val | Asp | Lys | Ser | Ser | Ser | Thr | Ala | Tyr | |
| | | 180 | | | | | 185 | | | | | 190 | | | | |

| ATG | CAG | CTC | AGC | AGC | CTG | ACA | TCT | GAG | GAC | TCT | GCG | GTC | TAT | TAC | TGT | 288 |
| Met | Gln | Leu | Ser | Ser | Leu | Thr | Ser | Glu | Asp | Ser | Ala | Val | Tyr | Tyr | Cys | |
| | 195 | | | | | 200 | | | | | 205 | | | | | |

| GCA | AGA | TCG | GAC | TAC | GGT | AGT | AGC | CAC | TTT | GAC | TAC | TGG | GGC | CAA | GGG | 336 |
| Ala | Arg | Ser | Asp | Tyr | Gly | Ser | Ser | His | Phe | Asp | Tyr | Trp | Gly | Gln | Gly | |
| 210 | | | | | 215 | | | | | 220 | | | | | 225 | |

| ACC | ACG | GTC | ACC | GTC | TCC | TCA | | | | | | | | | | 357 |
| Thr | Thr | Val | Thr | Val | Ser | Ser | | | | | | | | | | |
| | | | | 230 | | | | | | | | | | | | |

( 2 ) INFORMATION FOR SEQ ID NO: 12:

( i ) SEQUENCE CHARACTERISTICS:
( A ) LENGTH: 119 amino acids
( B ) TYPE: amino acid
( D ) TOPOLOGY: linear ( i i ) MOLECULE TYPE: protein ( x i ) SEQUENCE DESCRIPTION: SEQ ID NO: 12:

| Glu | Val | Gln | Leu | Gln | Gln | Ser | Gly | Ala | Glu | Leu | Val | Lys | Pro | Gly | Ala |
| 1 | | | | 5 | | | | | 10 | | | | | 15 | |

| Ser | Val | Lys | Leu | Ser | Cys | Lys | Ala | Ser | Gly | Tyr | Thr | Phe | Thr | Ser | Tyr |
| | | | 20 | | | | | 25 | | | | | 30 | | |

| Trp | Met | His | Trp | Val | Lys | Gln | Arg | Pro | Gly | Gln | Gly | Leu | Glu | Trp | Ile |
| | | 35 | | | | | 40 | | | | | 45 | | | |

| Gly | Glu | Ile | Asp | Pro | Ser | Asp | Ser | Tyr | Thr | Asn | Tyr | Asn | Gln | Lys | Phe |
| | 50 | | | | 55 | | | | | 60 | | | | | |

| Lys | Gly | Lys | Ala | Thr | Leu | Thr | Val | Asp | Lys | Ser | Ser | Ser | Thr | Ala | Tyr |
| 65 | | | | | 70 | | | | | 75 | | | | | 80 |

| Met | Gln | Leu | Ser | Ser | Leu | Thr | Ser | Glu | Asp | Ser | Ala | Val | Tyr | Tyr | Cys |
| | | | | 85 | | | | | 90 | | | | | 95 | |

| Ala | Arg | Ser | Asp | Tyr | Gly | Ser | Ser | His | Phe | Asp | Tyr | Trp | Gly | Gln | Gly |
| | | | 100 | | | | | 105 | | | | | 110 | | |

| Thr | Thr | Val | Thr | Val | Ser | Ser |
| | | | 115 | | | |

( 2 ) INFORMATION FOR SEQ ID NO: 13:

( i ) SEQUENCE CHARACTERISTICS:
        ( A ) LENGTH: 327 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: mouse
        ( B ) STRAIN: Balb/c
        ( D ) DEVELOPMENTAL STAGE: adult
        ( F ) TISSUE TYPE: Lymph node ( v i i ) IMMEDIATE SOURCE:
        ( B ) CLONE: S4 2D (light chain)

( i x ) FEATURE:
        ( A ) NAME/KEY: CDS
        ( B ) LOCATION:1..327

( x i ) SEQUENCE DESCRIPTION: SEQ ID NO: 13:

```
GAC  ATT  GAG  CTC  ACC  CAG  TCT  CCA  ACC  ACC  ATG  GCT  GCA  TCT  CCC  GGG       48
Asp  Ile  Glu  Leu  Thr  Gln  Ser  Pro  Thr  Thr  Met  Ala  Ala  Ser  Pro  Gly
120                      125                      130                      135

GAG  AAG  ATC  ACT  ATC  ACC  TGC  AGT  GCC  AGC  TCA  AGT  ATA  AGT  TCC  AAT       96
Glu  Lys  Ile  Thr  Ile  Thr  Cys  Ser  Ala  Ser  Ser  Ser  Ile  Ser  Ser  Asn
                    140                      145                      150

TAC  TTG  CAT  TGG  TAT  CAG  CAG  AAG  CCA  GGA  TTC  TCC  CCT  AAA  CTC  TTG      144
Tyr  Leu  His  Trp  Tyr  Gln  Gln  Lys  Pro  Gly  Phe  Ser  Pro  Lys  Leu  Leu
               155                      160                      165

ATT  TAT  AGG  ACA  TCC  AAT  CTG  GCT  TCT  GGA  GTC  CCA  GCT  CGC  TTC  AGT      192
Ile  Tyr  Arg  Thr  Ser  Asn  Leu  Ala  Ser  Gly  Val  Pro  Ala  Arg  Phe  Ser
          170                      175                      180

GGC  AGT  GGG  TCT  GGG  ACC  TCT  TAC  TCT  CTC  ACA  ATT  GGC  ACC  ATG  GAG      240
Gly  Ser  Gly  Ser  Gly  Thr  Ser  Tyr  Ser  Leu  Thr  Ile  Gly  Thr  Met  Glu
185                      190                      195

GCT  GAA  GAT  GTT  GCC  ACT  TAC  TAC  TGC  CAG  CAG  GGT  AGT  AGT  ATA  CCA      288
Ala  Glu  Asp  Val  Ala  Thr  Tyr  Tyr  Cys  Gln  Gln  Gly  Ser  Ser  Ile  Pro
200                      205                      210                      215

CGC  ACG  TTC  GGA  GGG  GGC  ACC  AAG  CTG  GAA  ATC  AAA  CGG                     327
Arg  Thr  Phe  Gly  Gly  Gly  Thr  Lys  Leu  Glu  Ile  Lys  Arg
               220                      225
```

( 2 ) INFORMATION FOR SEQ ID NO: 14:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 14:

```
Asp  Ile  Glu  Leu  Thr  Gln  Ser  Pro  Thr  Thr  Met  Ala  Ala  Ser  Pro  Gly
1                        5                        10                       15

Glu  Lys  Ile  Thr  Ile  Thr  Cys  Ser  Ala  Ser  Ser  Ser  Ile  Ser  Ser  Asn
                    20                       25                       30

Tyr  Leu  His  Trp  Tyr  Gln  Gln  Lys  Pro  Gly  Phe  Ser  Pro  Lys  Leu  Leu
               35                       40                       45
```

| Ile | Tyr | Arg | Thr | Ser | Asn | Leu | Ala | Ser | Gly | Val | Pro | Ala | Arg | Phe | Ser |
|     | 50  |     |     |     |     | 55  |     |     |     |     | 60  |     |     |     |     |

| Gly | Ser | Gly | Ser | Gly | Thr | Ser | Tyr | Ser | Leu | Thr | Ile | Gly | Thr | Met | Glu |
| 65  |     |     |     |     | 70  |     |     |     |     | 75  |     |     |     |     | 80  |

| Ala | Glu | Asp | Val | Ala | Thr | Tyr | Tyr | Cys | Gln | Gln | Gly | Ser | Ser | Ile | Pro |
|     |     |     |     | 85  |     |     |     |     | 90  |     |     |     |     | 95  |     |

| Arg | Thr | Phe | Gly | Gly | Gly | Thr | Lys | Leu | Glu | Ile | Lys | Arg |
|     |     |     | 100 |     |     |     |     | 105 |     |     |     |     |

(2) INFORMATION FOR SEQ ID NO: 15:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: mouse
        (B) STRAIN: Balb/c
        (D) DEVELOPMENTAL STAGE: adult
        (F) TISSUE TYPE: Lymph node (vii) IMMEDIATE SOURCE:
        (B) CLONE: S4 2D (heavy chain)

(ix) FEATURE:
        (A) NAME/KEY: CDS
        (B) LOCATION:1..354

(xi) SEQUENCE DESCRIPTION: SEQ ID NO: 15:

| GAG | GTC | AAG | CTG | CAG | CAG | TCA | GGA | CCT | GAG | CTG | GTA | AAG | CCT | GGG | GCT | 48 |
| Glu | Val | Lys | Leu | Gln | Gln | Ser | Gly | Pro | Glu | Leu | Val | Lys | Pro | Gly | Ala |    |
| 110 |     |     |     |     | 115 |     |     |     |     | 120 |     |     |     |     | 125 |    |

| TCA | GTG | AAG | ATG | TCC | TGC | AAG | GCT | TCT | GGA | TAC | GCA | TTC | ATA | AGT | TTT | 96 |
| Ser | Val | Lys | Met | Ser | Cys | Lys | Ala | Ser | Gly | Tyr | Ala | Phe | Ile | Ser | Phe |    |
|     |     |     |     | 130 |     |     |     |     | 135 |     |     |     |     | 140 |     |    |

| GTT | ATG | CAC | TGG | GTG | AAG | CAG | AAG | CCT | GGG | CAG | GGC | CTT | GAG | TGG | ATT | 144 |
| Val | Met | His | Trp | Val | Lys | Gln | Lys | Pro | Gly | Gln | Gly | Leu | Glu | Trp | Ile |     |
|     |     |     |     | 145 |     |     |     |     | 150 |     |     |     |     | 155 |     |     |

| GGA | TTT | ATT | AAT | CCT | TAC | AAT | GAT | GGT | ACT | AAG | TAC | AAT | GAG | AAG | TTC | 192 |
| Gly | Phe | Ile | Asn | Pro | Tyr | Asn | Asp | Gly | Thr | Lys | Tyr | Asn | Glu | Lys | Phe |     |
|     |     |     | 160 |     |     |     |     | 165 |     |     |     |     | 170 |     |     |     |

| AAA | GAC | AAG | GCC | ACA | CTG | ACT | TCA | GAC | AAA | TCC | TCC | AGC | ACA | GCC | TAC | 240 |
| Lys | Asp | Lys | Ala | Thr | Leu | Thr | Ser | Asp | Lys | Ser | Ser | Ser | Thr | Ala | Tyr |     |
|     | 175 |     |     |     |     | 180 |     |     |     |     | 185 |     |     |     |     |     |

| ATG | GAG | CTC | AGC | AGC | CTG | ACC | TCT | GAG | GAC | TCT | GCG | GTC | TAT | TAC | TGT | 288 |
| Met | Glu | Leu | Ser | Ser | Leu | Thr | Ser | Glu | Asp | Ser | Ala | Val | Tyr | Tyr | Cys |     |
| 190 |     |     |     |     | 195 |     |     |     |     | 200 |     |     |     |     | 205 |     |

| GCA | AGT | GGG | GAT | TAC | GAC | AGG | GCT | ATG | GAC | TAC | TGG | GGC | CAA | GGG | ACC | 336 |
| Ala | Ser | Gly | Asp | Tyr | Asp | Arg | Ala | Met | Asp | Tyr | Trp | Gly | Gln | Gly | Thr |     |
|     |     |     |     | 210 |     |     |     |     | 215 |     |     |     |     | 220 |     |     |

| ACG | GTC | ACC | GTC | TCC | TCA | 354 |
| Thr | Val | Thr | Val | Ser | Ser |     |
|     |     |     | 225 |     |     |     |

(2) INFORMATION FOR SEQ ID NO: 16:

(i) SEQUENCE CHARACTERISTICS:
  (A) LENGTH: 118 amino acids
  (B) TYPE: amino acid
  (D) TOPOLOGY: linear (ii) MOLECULE TYPE: protein (xi) SEQUENCE DESCRIPTION: SEQ ID NO: 16:

| Glu | Val | Lys | Leu | Gln | Gln | Ser | Gly | Pro | Glu | Leu | Val | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Met | Ser | Cys | Lys | Ala | Ser | Gly | Tyr | Ala | Phe | Ile | Ser | Phe |
|---|---|---|---|---|---|---|---|---|---|---|---|---|---|---|---|
| | | | 20 | | | | | 25 | | | | | 30 | | |

| Val | Met | His | Trp | Val | Lys | Gln | Lys | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Phe | Ile | Asn | Pro | Tyr | Asn | Asp | Gly | Thr | Lys | Tyr | Asn | Glu | Lys | Phe |
|---|---|---|---|---|---|---|---|---|---|---|---|---|---|---|---|
| | 50 | | | | | 55 | | | | | | 60 | | | |

| Lys | Asp | Lys | Ala | Thr | Leu | Thr | Ser | Asp | Lys | Ser | Ser | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Thr | Ser | Glu | Asp | Ser | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ser | Gly | Asp | Tyr | Asp | Arg | Ala | Met | Asp | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Thr | Val | Thr | Val | Ser | Ser |
|---|---|---|---|---|---|
| | 115 | | | | |

(2) INFORMATION FOR SEQ ID NO: 17:

(i) SEQUENCE CHARACTERISTICS:
    (A) LENGTH: 717 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
    (A) ORGANISM: mouse
    (B) STRAIN: Balb/c
    (D) DEVELOPMENTAL STAGE: adult
    (F) TISSUE TYPE: splenocytes (vii) IMMEDIATE SOURCE:
    (B) CLONE: 4B2

(ix) FEATURE:
    (A) NAME/KEY: CDS
    (B) LOCATION: 1..717

(xi) SEQUENCE DESCRIPTION: SEQ ID NO: 17:

| GAG | GTG | AAG | CTG | CAG | GAG | TCT | GGG | GGA | GAC | TTA | GTG | AAG | CCT | GGA | GGG | 48 |
|---|---|---|---|---|---|---|---|---|---|---|---|---|---|---|---|---|
| Glu | Val | Lys | Leu | Gln | Glu | Ser | Gly | Gly | Asp | Leu | Val | Lys | Pro | Gly | Gly | |
| 120 | | | | | 125 | | | | | 130 | | | | | | |

| TCC | CTG | AAA | CTC | TCC | TGT | GCA | GCC | TCT | GGA | TTC | ACT | TTC | AGT | AGC | TAT | 96 |
|---|---|---|---|---|---|---|---|---|---|---|---|---|---|---|---|---|
| Ser | Leu | Lys | Leu | Ser | Cys | Ala | Ala | Ser | Gly | Phe | Thr | Phe | Ser | Ser | Tyr | |
| 135 | | | | | 140 | | | | | 145 | | | | | 150 | |

| GGC | ATG | TCT | TGG | GTT | CGG | CAG | ACT | CCA | GAC | AAG | AGG | CTG | GAG | TCT | GTC | 144 |
|---|---|---|---|---|---|---|---|---|---|---|---|---|---|---|---|---|
| Gly | Met | Ser | Trp | Val | Arg | Gln | Thr | Pro | Asp | Lys | Arg | Leu | Glu | Ser | Val | |
| | | | | 155 | | | | | 160 | | | | | 165 | | |

| GCA | ACC | ATT | AGT | AGT | GGT | GGT | GCT | TAC | ATC | TAC | TAT | CCA | GAC | AGT | GTG | 192 |
|---|---|---|---|---|---|---|---|---|---|---|---|---|---|---|---|---|
| Ala | Thr | Ile | Ser | Ser | Gly | Gly | Ala | Tyr | Ile | Tyr | Tyr | Pro | Asp | Ser | Val | |
| | | 170 | | | | | 175 | | | | | 180 | | | | |

```
AAG  GGG  CGA  TTC  ACC  ATC  TCC  AGA  GAC  AAT  GCC  AAG  AAC  ACC  CTG  TAC    240
Lys  Gly  Arg  Phe  Thr  Ile  Ser  Arg  Asp  Asn  Ala  Lys  Asn  Thr  Leu  Tyr
          185                      190                     195

CTG  CAA  ATG  AGC  AGT  CTG  AAG  TCT  GAG  GAC  ACA  GCC  ATG  TAT  TAC  TGT    288
Leu  Gln  Met  Ser  Ser  Leu  Lys  Ser  Glu  Asp  Thr  Ala  Met  Tyr  Tyr  Cys
     200                      205                     210

GCA  AGA  CTT  GAA  ACC  GGG  GAC  TAT  GCT  TTG  GAC  TAC  TGG  GGC  CAA  GGG    336
Ala  Arg  Leu  Glu  Thr  Gly  Asp  Tyr  Ala  Leu  Asp  Tyr  Trp  Gly  Gln  Gly
215                      220                     225                     230

ACC  ACG  GTC  ACC  GTC  TCC  TCA  GGT  GGC  GGT  GGC  TCG  GGC  GGT  GGT  GGG    384
Thr  Thr  Val  Thr  Val  Ser  Ser  Gly  Gly  Gly  Gly  Ser  Gly  Gly  Gly  Gly
               235                      240                     245

TCG  GGT  GGC  GGC  GGA  TCT  GAC  ATT  GAG  CTC  ACC  CAG  TCT  CCA  GCT  TCT    432
Ser  Gly  Gly  Gly  Gly  Ser  Asp  Ile  Glu  Leu  Thr  Gln  Ser  Pro  Ala  Ser
          250                      255                     260

TTG  GCT  GTC  TCT  CTA  GGG  CAG  AGG  GCC  ACC  ATA  TTC  TGC  AAG  GAC  AGC    480
Leu  Ala  Val  Ser  Leu  Gly  Gln  Arg  Ala  Thr  Ile  Phe  Cys  Lys  Asp  Ser
          265                      270                     275

CAA  AGT  GTT  GAT  TAT  GAT  GGT  GAT  AGT  TAT  ATG  AAC  TGG  TAC  CAA  CAG    528
Gln  Ser  Val  Asp  Tyr  Asp  Gly  Asp  Ser  Tyr  Met  Asn  Trp  Tyr  Gln  Gln
     280                      285                     290

AAA  CCA  GGA  CAG  CCA  CCC  AAA  CTC  CTC  ATC  TAT  GCT  CGA  TCC  AAT  CTA    576
Lys  Pro  Gly  Gln  Pro  Pro  Lys  Leu  Leu  Ile  Tyr  Ala  Arg  Ser  Asn  Leu
295                      300                     305                     310

GAA  TCT  GGG  GTC  CCT  GCC  AGG  TTT  AGT  GGC  AGT  GGG  TCT  GGG  ACA  GAC    624
Glu  Ser  Gly  Val  Pro  Ala  Arg  Phe  Ser  Gly  Ser  Gly  Ser  Gly  Thr  Asp
               315                      320                     325

TTC  AGC  CTC  AAC  ATC  CAT  CCT  GTG  GAG  GAG  GAT  GAT  ATT  GCA  ATG  TAT    672
Phe  Ser  Leu  Asn  Ile  His  Pro  Val  Glu  Glu  Asp  Asp  Ile  Ala  Met  Tyr
          330                      335                     340

TTC  TGT  CAG  CAA  AGT  AGG  AAG  GTT  CCG  TGG  TCG  TTC  GGT  GGA  GGG           717
Phe  Cys  Gln  Gln  Ser  Arg  Lys  Val  Pro  Trp  Ser  Phe  Gly  Gly  Gly
               345                      350                     355
```

(2) INFORMATION FOR SEQ ID NO: 18:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO: 18:

```
Glu  Val  Lys  Leu  Gln  Glu  Ser  Gly  Gly  Asp  Leu  Val  Lys  Pro  Gly  Gly
 1                    5                     10                     15

Ser  Leu  Lys  Leu  Ser  Cys  Ala  Ala  Ser  Gly  Phe  Thr  Phe  Ser  Ser  Tyr
          20                      25                     30

Gly  Met  Ser  Trp  Val  Arg  Gln  Thr  Pro  Asp  Lys  Arg  Leu  Glu  Ser  Val
          35                      40                     45

Ala  Thr  Ile  Ser  Ser  Gly  Gly  Ala  Tyr  Ile  Tyr  Tyr  Pro  Asp  Ser  Val
     50                      55                     60

Lys  Gly  Arg  Phe  Thr  Ile  Ser  Arg  Asp  Asn  Ala  Lys  Asn  Thr  Leu  Tyr
65                       70                     75                     80

Leu  Gln  Met  Ser  Ser  Leu  Lys  Ser  Glu  Asp  Thr  Ala  Met  Tyr  Tyr  Cys
                85                      90                     95

Ala  Arg  Leu  Glu  Thr  Gly  Asp  Tyr  Ala  Leu  Asp  Tyr  Trp  Gly  Gln  Gly
               100                     105                    110

Thr  Thr  Val  Thr  Val  Ser  Ser  Gly  Gly  Gly  Ser  Gly  Gly  Gly  Gly
               115                     120                    125
```

```
Ser  Gly  Gly  Gly  Gly  Ser  Asp  Ile  Glu  Leu  Thr  Gln  Ser  Pro  Ala  Ser
     130                      135                 140

Leu  Ala  Val  Ser  Leu  Gly  Gln  Arg  Ala  Thr  Ile  Phe  Cys  Lys  Asp  Ser
145                      150                 155                      160

Gln  Ser  Val  Asp  Tyr  Asp  Gly  Asp  Ser  Tyr  Met  Asn  Trp  Tyr  Gln  Gln
                    165                 170                      175

Lys  Pro  Gly  Gln  Pro  Pro  Lys  Leu  Leu  Ile  Tyr  Ala  Arg  Ser  Asn  Leu
               180                 185                           190

Glu  Ser  Gly  Val  Pro  Ala  Arg  Phe  Ser  Gly  Ser  Gly  Ser  Gly  Thr  Asp
          195                      200                 205

Phe  Ser  Leu  Asn  Ile  His  Pro  Val  Glu  Glu  Asp  Asp  Ile  Ala  Met  Tyr
     210                 215                      220

Phe  Cys  Gln  Gln  Ser  Arg  Lys  Val  Pro  Trp  Ser  Phe  Gly  Gly  Gly
225                      230                      235
```

( 2 ) INFORMATION FOR SEQ ID NO: 19:

( i ) SEQUENCE CHARACTERISTICS:
            ( A ) LENGTH: 732 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
            ( A ) ORGANISM: mouse
            ( B ) STRAIN: Balb/c
            ( F ) TISSUE TYPE: splenocytes ( v i i ) IMMEDIATE SOURCE:
            ( B ) CLONE: 10 D 2 (single-chain Fv, heavy and light
                  chain plus linker)

( i x ) FEATURE:
            ( A ) NAME/KEY: CDS
            ( B ) LOCATION:1..732

( x i ) SEQUENCE DESCRIPTION: SEQ ID NO: 19:

```
GAG  GTG  CAG  CTG  CAG  CAG  TCT  GGG  GCT  GAA  CTG  GTG  AAG  CCT  GGG  GCT      48
Glu  Val  Gln  Leu  Gln  Gln  Ser  Gly  Ala  Glu  Leu  Val  Lys  Pro  Gly  Ala
240                      245                 250                      255

TCA  GTG  AAG  TTG  TCC  TGC  AAG  GCT  TCC  GGC  TAC  ACC  TTC  ACC  AGC  CAC      96
Ser  Val  Lys  Leu  Ser  Cys  Lys  Ala  Ser  Gly  Tyr  Thr  Phe  Thr  Ser  His
                    260                 265                      270

TGG  ATG  CAC  TGG  GTG  AAG  CAG  AGG  GCT  GGA  CAA  GGC  CTT  GAG  TGG  ATC     144
Trp  Met  His  Trp  Val  Lys  Gln  Arg  Ala  Gly  Gln  Gly  Leu  Glu  Trp  Ile
               275                 280                      285

GGA  GAG  TTT  AAT  CCC  AGC  AAC  GGC  CGT  ACT  AAC  TAC  AAT  GAG  AAA  TTC     192
Gly  Glu  Phe  Asn  Pro  Ser  Asn  Gly  Arg  Thr  Asn  Tyr  Asn  Glu  Lys  Phe
          290                      295                 300

AAG  AGC  AAG  GCC  ACA  CTG  ACT  GTA  GAC  AAA  TCC  TCC  AGC  ACA  GCC  TAC     240
Lys  Ser  Lys  Ala  Thr  Leu  Thr  Val  Asp  Lys  Ser  Ser  Ser  Thr  Ala  Tyr
     305                      310                 315

ATG  CAA  CTC  AGC  AGC  CTG  ACA  TCT  GAG  GAC  TCT  GCG  GTC  TAT  TAC  TGT     288
Met  Gln  Leu  Ser  Ser  Leu  Thr  Ser  Glu  Asp  Ser  Ala  Val  Tyr  Tyr  Cys
320                      325                 330                      335

GCC  AGT  CGG  GAC  TAT  GAT  TAC  GAC  GGA  CGG  TAC  TTT  GAC  TAC  TGG  GGC     336
Ala  Ser  Arg  Asp  Tyr  Asp  Tyr  Asp  Gly  Arg  Tyr  Phe  Asp  Tyr  Trp  Gly
                    340                 345                      350
```

| | | | | | | | | | | | | | | | | |
|---|---|---|---|---|---|---|---|---|---|---|---|---|---|---|---|---|
| CAA | GGG | ACC | ACG | GTC | ACC | GTC | TCC | TCA | GGT | GGC | GGT | GGC | TCG | GGC | GGT | 384 |
| Gln | Gly | Thr | Thr | Val | Thr | Val | Ser | Ser | Gly | Gly | Gly | Gly | Ser | Gly | Gly | |
| | | 355 | | | | | | 360 | | | | | 365 | | | |
| GGT | GGG | TCG | GGT | GGC | GGC | GGA | TCT | GAC | ATT | GAG | CTC | ACC | CAG | TCT | CCA | 432 |
| Gly | Gly | Ser | Gly | Gly | Gly | Gly | Ser | Asp | Ile | Glu | Leu | Thr | Gln | Ser | Pro | |
| | | 370 | | | | | 375 | | | | | 380 | | | | |
| GCA | ATC | ATG | TCT | GCA | TCT | CCA | GGG | GAG | AAG | GTC | ACC | ATG | ACC | TGC | AGT | 480 |
| Ala | Ile | Met | Ser | Ala | Ser | Pro | Gly | Glu | Lys | Val | Thr | Met | Thr | Cys | Ser | |
| 385 | | | | | 390 | | | | | 395 | | | | | | |
| GCC | AGC | TCA | AGT | GTA | AGT | TAC | ATG | TAC | TGG | TAC | CAG | CAG | AAA | CCA | GGA | 528 |
| Ala | Ser | Ser | Ser | Val | Ser | Tyr | Met | Tyr | Trp | Tyr | Gln | Gln | Lys | Pro | Gly | |
| 400 | | | | | 405 | | | | | 410 | | | | | 415 | |
| TCC | TCC | CCC | AGA | CTC | CTG | ATT | TAT | GAC | ACA | TCC | AAC | CTG | GCT | TCT | GGA | 576 |
| Ser | Ser | Pro | Arg | Leu | Leu | Ile | Tyr | Asp | Thr | Ser | Asn | Leu | Ala | Ser | Gly | |
| | | | | 420 | | | | | 425 | | | | | 430 | | |
| GTC | CCT | GTT | CGC | TTC | AGT | GGC | AGT | GGG | TCT | GGG | ACC | TCT | TAC | TCT | CTC | 624 |
| Val | Pro | Val | Arg | Phe | Ser | Gly | Ser | Gly | Ser | Gly | Thr | Ser | Tyr | Ser | Leu | |
| | | | 435 | | | | | 440 | | | | | 445 | | | |
| ACA | ATC | AGC | CGA | ATG | GAG | GCT | GAA | GAT | GCT | GCC | ACT | TAT | TAC | TGC | CAG | 672 |
| Thr | Ile | Ser | Arg | Met | Glu | Ala | Glu | Asp | Ala | Ala | Thr | Tyr | Tyr | Cys | Gln | |
| | | 450 | | | | | 455 | | | | | 460 | | | | |
| CAG | TGG | AGT | AGT | TAC | CCA | CCC | ATG | TAC | ACG | TTC | GGA | GGG | GGG | ACC | AAG | 720 |
| Gln | Trp | Ser | Ser | Tyr | Pro | Pro | Met | Tyr | Thr | Phe | Gly | Gly | Gly | Thr | Lys | |
| | 465 | | | | | 470 | | | | | 475 | | | | | |
| CTG | GAA | ATA | AAA | | | | | | | | | | | | | 732 |
| Leu | Glu | Ile | Lys | | | | | | | | | | | | | |
| 480 | | | | | | | | | | | | | | | | |

(2) INFORMATION FOR SEQ ID NO: 20:

(i) SEQUENCE CHARACTERISTICS:
        (A) LENGTH: 244 amino acids
        (B) TYPE: amino acid
        (D) TOPOLOGY: linear (ii) MOLECULE TYPE: protein (xi) SEQUENCE DESCRIPTION: SEQ ID NO: 20:

| | | | | | | | | | | | | | | |
|---|---|---|---|---|---|---|---|---|---|---|---|---|---|---|
| Glu | Val | Gln | Leu | Gln | Gln | Ser | Gly | Ala | Glu | Leu | Val | Lys | Pro | Gly | Ala |
| 1 | | | | 5 | | | | | 10 | | | | | 15 | |
| Ser | Val | Lys | Leu | Ser | Cys | Lys | Ala | Ser | Gly | Tyr | Thr | Phe | Thr | Ser | His |
| | | | 20 | | | | | 25 | | | | | 30 | | |
| Trp | Met | His | Trp | Val | Lys | Gln | Arg | Ala | Gly | Gln | Gly | Leu | Glu | Trp | Ile |
| | | 35 | | | | | 40 | | | | | 45 | | | |
| Gly | Glu | Phe | Asn | Pro | Ser | Asn | Gly | Arg | Thr | Asn | Tyr | Asn | Glu | Lys | Phe |
| | 50 | | | | | 55 | | | | | 60 | | | | |
| Lys | Ser | Lys | Ala | Thr | Leu | Thr | Val | Asp | Lys | Ser | Ser | Thr | Ala | Tyr | |
| 65 | | | | | 70 | | | | | 75 | | | | | 80 |
| Met | Gln | Leu | Ser | Ser | Leu | Thr | Ser | Glu | Asp | Ser | Ala | Val | Tyr | Tyr | Cys |
| | | | | 85 | | | | | 90 | | | | | 95 | |
| Ala | Ser | Arg | Asp | Tyr | Asp | Tyr | Asp | Gly | Arg | Tyr | Phe | Asp | Tyr | Trp | Gly |
| | | | 100 | | | | | 105 | | | | | 110 | | |
| Gln | Gly | Thr | Thr | Val | Thr | Val | Ser | Ser | Gly | Gly | Gly | Gly | Ser | Gly | Gly |
| | | 115 | | | | | 120 | | | | | 125 | | | |
| Gly | Gly | Ser | Gly | Gly | Gly | Gly | Ser | Asp | Ile | Glu | Leu | Thr | Gln | Ser | Pro |
| | 130 | | | | | 135 | | | | | 140 | | | | |
| Ala | Ile | Met | Ser | Ala | Ser | Pro | Gly | Glu | Lys | Val | Thr | Met | Thr | Cys | Ser |
| 145 | | | | | 150 | | | | | 155 | | | | | 160 |
| Ala | Ser | Ser | Ser | Val | Ser | Tyr | Met | Tyr | Trp | Tyr | Gln | Gln | Lys | Pro | Gly |
| | | | | 165 | | | | | 170 | | | | | 175 | |

```
Ser  Ser  Pro  Arg  Leu  Leu  Ile  Tyr  Asp  Thr  Ser  Asn  Leu  Ala  Ser  Gly
               180                      185                      190

Val  Pro  Val  Arg  Phe  Ser  Gly  Ser  Gly  Ser  Gly  Thr  Ser  Tyr  Ser  Leu
          195                 200                      205

Thr  Ile  Ser  Arg  Met  Glu  Ala  Glu  Asp  Ala  Ala  Thr  Tyr  Tyr  Cys  Gln
     210                      215                      220

Gln  Trp  Ser  Ser  Tyr  Pro  Pro  Met  Tyr  Thr  Phe  Gly  Gly  Gly  Thr  Lys
225                      230                      235                      240

Leu  Glu  Ile  Lys
```

(2) INFORMATION FOR SEQ ID NO: 21:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: N-terminal (vi) ORIGINAL SOURCE:
        (A) ORGANISM: mouse
        (B) STRAIN: Balb/c
        (F) TISSUE TYPE: splenocytes (vii) IMMEDIATE SOURCE:
        (B) CLONE: 3 D 3 (single-chain Fv, heavy and light chain
            plus linker)

(ix) FEATURE:
        (A) NAME/KEY: CDS
        (B) LOCATION:1..732

(xi) SEQUENCE DESCRIPTION: SEQ ID NO: 21:

```
GAG  GTC  CAA  CTG  CAG  CAG  TCA  GGG  GCT  GAA  CTG  GTG  AAG  CCT  GGG  GCT        48
Glu  Val  Gln  Leu  Gln  Gln  Ser  Gly  Ala  Glu  Leu  Val  Lys  Pro  Gly  Ala
245                      250                      255                      260

TCA  GTG  AAG  TTG  TCC  TGC  AAG  GCT  TCC  GGC  TAC  ACC  TTC  ACC  AGC  CAC        96
Ser  Val  Lys  Leu  Ser  Cys  Lys  Ala  Ser  Gly  Tyr  Thr  Phe  Thr  Ser  His
                    265                      270                      275

TGG  ATG  CAC  TGG  GTG  AAG  CAG  AGG  GCT  GGA  CAA  GGC  CTT  GAG  TGG  ATC       144
Trp  Met  His  Trp  Val  Lys  Gln  Arg  Ala  Gly  Gln  Gly  Leu  Glu  Trp  Ile
               280                      285                      290

GGA  GAG  TTT  AAT  CCC  AGC  AAC  GGC  CGT  ACT  AAC  TAC  AAT  GAG  AAA  ATC       192
Gly  Glu  Phe  Asn  Pro  Ser  Asn  Gly  Arg  Thr  Asn  Tyr  Asn  Glu  Lys  Ile
          295                      300                      305

AAG  AGC  AAG  GCC  ACA  CTG  ACT  GTA  GAC  AAA  TCC  TCC  AGC  ACA  GCC  TAC       240
Lys  Ser  Lys  Ala  Thr  Leu  Thr  Val  Asp  Lys  Ser  Ser  Ser  Thr  Ala  Tyr
     310                      315                      320

ATG  CAA  CTC  AGC  AGC  CTG  ACA  TCT  GAG  GAC  TCT  GCG  GTC  TAT  TAC  TGT       288
Met  Gln  Leu  Ser  Ser  Leu  Thr  Ser  Glu  Asp  Ser  Ala  Val  Tyr  Tyr  Cys
325                      330                      335                      340

GCC  AGT  CGG  GAC  TAT  GAT  TAC  GAC  GGA  CGG  TAC  TTT  GAC  TAC  TGG  GGC       336
Ala  Ser  Arg  Asp  Tyr  Asp  Tyr  Asp  Gly  Arg  Tyr  Phe  Asp  Tyr  Trp  Gly
                    345                      350                      355

CAA  GGG  ACC  ACG  GTC  ACC  GTC  TCC  TCA  GGT  GGC  GGT  GGC  TCG  GGC  GGT       384
Gln  Gly  Thr  Thr  Val  Thr  Val  Ser  Ser  Gly  Gly  Gly  Gly  Ser  Gly  Gly
               360                      365                      370

GGT  GGG  TCG  GGT  GGC  GGC  GGA  TCT  GAC  ATT  GAG  CTC  ACC  CAG  TCT  CCA       432
```

```
Gly Gly Ser Gly Gly Gly Gly Ser Asp Ile Glu Leu Thr Gln Ser Pro
        375                 380                     385

ACA ATC ATG TCT GCA TCT CCA GGG GAG AAG GTC ACC ATG ACC TGC AGT         480
Thr Ile Met Ser Ala Ser Pro Gly Glu Lys Val Thr Met Thr Cys Ser
    390                 395                 400

GAC AGC TCA AGT GTA AGT TAC ATG TAC TGG TAC CAG CAG AAG ACA GGA         528
Asp Ser Ser Ser Val Ser Tyr Met Tyr Trp Tyr Gln Gln Lys Thr Gly
405             410                 415                     420

TCC TCC CCC AGA CTC CTG ATT TAT GAC ACA TCC AAC CTG GCT TCT GGA         576
Ser Ser Pro Arg Leu Leu Ile Tyr Asp Thr Ser Asn Leu Ala Ser Gly
                425                 430                     435

GTC CCT GTT CGC TTC AGT GGC AGT GGG TCT GGG ACC TCT TAC TCT CTC         624
Val Pro Val Arg Phe Ser Gly Ser Gly Ser Gly Thr Ser Tyr Ser Leu
                440                 445                 450

ACA ATC AGC CGA ATG GAG GCT GAA GAT GCT GCC ACT TAT TAC TGC CAG         672
Thr Ile Ser Arg Met Glu Ala Glu Asp Ala Ala Thr Tyr Tyr Cys Gln
            455                 460                 465

CAG TGG AGT AGT TAC CCA CCC ATG TAC ACG TTC GGA GGG GGG ACC AAG         720
Gln Trp Ser Ser Tyr Pro Pro Met Tyr Thr Phe Gly Gly Gly Thr Lys
    470                 475                 480

CTG GAA ATA AAA                                                         732
Leu Glu Ile Lys
485
```

( 2 ) INFORMATION FOR SEQ ID NO: 22:

( i ) SEQUENCE CHARACTERISTICS:
        ( A ) LENGTH: 244 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 22:

```
Glu Val Gln Leu Gln Gln Ser Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Arg Ala Gly Gln Gly Leu Glu Trp Ile
        35                  40                  45

Gly Glu Phe Asn Pro Ser Asn Gly Arg Thr Asn Tyr Asn Glu Lys Ile
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Gly Ser Asp Ile Glu Leu Thr Gln Ser Pro
    130                 135                 140

Thr Ile Met Ser Ala Ser Pro Gly Glu Lys Val Thr Met Thr Cys Ser
145                 150                 155                 160

Asp Ser Ser Ser Val Ser Tyr Met Tyr Trp Tyr Gln Gln Lys Thr Gly
                165                 170                 175

Ser Ser Pro Arg Leu Leu Ile Tyr Asp Thr Ser Asn Leu Ala Ser Gly
            180                 185                 190

Val Pro Val Arg Phe Ser Gly Ser Gly Ser Gly Thr Ser Tyr Ser Leu
```

|  |  |  |  | 195 |  |  |  | 200 |  |  |  | 205 |  |  |  |
|---|---|---|---|---|---|---|---|---|---|---|---|---|---|---|---|
| Thr | Ile | Ser | Arg | Met | Glu | Ala | Glu | Asp | Ala | Ala | Thr | Tyr | Tyr | Cys | Gln |
|  |  |  |  |  |  | 215 |  |  |  |  | 220 |  |  |  |  |
| 210 |  |  |  |  |  |  |  |  |  |  |  |  |  |  |  |
| Gln | Trp | Ser | Ser | Tyr | Pro | Pro | Met | Tyr | Thr | Phe | Gly | Gly | Gly | Thr | Lys |
| 225 |  |  |  |  | 230 |  |  |  |  | 235 |  |  |  |  | 240 |
| Leu | Glu | Ile | Lys |  |  |  |  |  |  |  |  |  |  |  |  |

( 2 ) INFORMATION FOR SEQ ID NO: 23:

( i ) SEQUENCE CHARACTERISTICS:
        ( A ) LENGTH: 738 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: mouse
        ( B ) STRAIN: Balb/c
        ( F ) TISSUE TYPE: splenocytes ( v i i ) IMMEDIATE SOURCE:
        ( B ) CLONE: 1 E 3 (single-chain Fv, heavy and light chain
            plus linker)

( i x ) FEATURE:
        ( A ) NAME/KEY: CDS
        ( B ) LOCATION:1..738

( x i ) SEQUENCE DESCRIPTION: SEQ ID NO: 23:

| GAG | GTG | CAG | CTG | CAG | CAG | TCT | GGG | GCT | GAA | CTG | GTG | AAG | CCT | GGG | GCT | 48 |
|---|---|---|---|---|---|---|---|---|---|---|---|---|---|---|---|---|
| Glu | Val | Gln | Leu | Gln | Gln | Ser | Gly | Ala | Glu | Leu | Val | Lys | Pro | Gly | Ala |  |
| 245 |  |  |  |  | 250 |  |  |  |  | 255 |  |  |  |  | 260 |  |
| TCA | GTG | AAG | TTG | TCC | TGC | AAG | GCT | TCC | GGC | TAC | ACC | TTC | ACC | AGC | CAC | 96 |
| Ser | Val | Lys | Leu | Ser | Cys | Lys | Ala | Ser | Gly | Tyr | Thr | Phe | Thr | Ser | His |  |
|  |  |  |  | 265 |  |  |  |  | 270 |  |  |  |  | 275 |  |  |
| TGG | ATG | CAC | TGG | GTG | AAG | CAG | AGG | GCT | GGA | CAA | GGC | CTT | GAG | TGG | ATC | 144 |
| Trp | Met | His | Trp | Val | Lys | Gln | Arg | Ala | Gly | Gln | Gly | Leu | Glu | Trp | Ile |  |
|  |  |  | 280 |  |  |  |  | 285 |  |  |  |  | 290 |  |  |  |
| GGA | GAG | TTT | AAT | CCC | AGC | AAC | GGC | CGT | ACT | AAC | TAC | AAT | GAG | AAA | TTC | 192 |
| Gly | Glu | Phe | Asn | Pro | Ser | Asn | Gly | Arg | Thr | Asn | Tyr | Asn | Glu | Lys | Phe |  |
|  |  | 295 |  |  |  |  | 300 |  |  |  |  | 305 |  |  |  |  |
| AAG | AGC | AAG | GCC | ACA | CTG | ACT | GTA | GAC | AAA | TCC | TCC | AGC | ACA | GCT | TAC | 240 |
| Lys | Ser | Lys | Ala | Thr | Leu | Thr | Val | Asp | Lys | Ser | Ser | Ser | Thr | Ala | Tyr |  |
| 310 |  |  |  |  | 315 |  |  |  |  | 320 |  |  |  |  |  |  |
| ATG | CAA | CTC | AGC | AGC | CTG | ACA | TCT | GAG | GAC | TCT | GCG | GTC | TAT | TAC | TGT | 288 |
| Met | Gln | Leu | Ser | Ser | Leu | Thr | Ser | Glu | Asp | Ser | Ala | Val | Tyr | Tyr | Cys |  |
| 325 |  |  |  |  | 330 |  |  |  |  | 335 |  |  |  |  | 340 |  |
| GCC | AGT | CGG | GAC | TAT | GAT | TAC | GAC | GGA | CGG | TAC | TTT | GAC | TAC | TGG | GGC | 336 |
| Ala | Ser | Arg | Asp | Tyr | Asp | Tyr | Asp | Gly | Arg | Tyr | Phe | Asp | Tyr | Trp | Gly |  |
|  |  |  |  | 345 |  |  |  |  | 350 |  |  |  |  | 355 |  |  |
| CAA | GGG | ACC | ACG | GTC | ACC | GTC | TCC | TCA | GGT | GGC | GGT | GGC | TCG | GGC | GGT | 384 |
| Gln | Gly | Thr | Thr | Val | Thr | Val | Ser | Ser | Gly | Gly | Gly | Gly | Ser | Gly | Gly |  |
|  |  |  | 360 |  |  |  |  | 365 |  |  |  |  | 370 |  |  |  |
| GGT | GGG | TCG | GGT | GGC | GGC | GGA | TCT | GGA | TCT | GAC | ATT | GAG | CTC | ACC | CAG | 432 |
| Gly | Gly | Ser | Gly | Gly | Gly | Gly | Ser | Gly | Ser | Asp | Ile | Glu | Leu | Thr | Gln |  |
|  |  | 375 |  |  |  |  | 380 |  |  |  |  | 385 |  |  |  |  |
| TCT | CCA | ACA | ATC | ATG | TCT | GCA | TCT | CCA | GGG | GAG | AAG | GTC | ACC | ATG | ACC | 480 |
| Ser | Pro | Thr | Ile | Met | Ser | Ala | Ser | Pro | Gly | Glu | Lys | Val | Thr | Met | Thr |  |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 390 |     |     |     |     | 395 |     |     |     |     | 400 |     |     |     |     |
| TGC | AGT | GAC | AGC | TCA | AGT | GTA | AGT | TAC | ATG | TAC | TGG | TAC | CAG | CAG | AAG | 528 |
| Cys | Ser | Asp | Ser | Ser | Ser | Val | Ser | Tyr | Met | Tyr | Trp | Tyr | Gln | Gln | Lys |     |
| 405 |     |     |     |     | 410 |     |     |     |     | 415 |     |     |     |     | 420 |     |
| CCA | GGA | TCC | TCC | CCC | AGA | CTC | CTG | ATT | TAT | GAC | ACA | TCC | AAC | CTG | GCT | 576 |
| Pro | Gly | Ser | Ser | Pro | Arg | Leu | Leu | Ile | Tyr | Asp | Thr | Ser | Asn | Leu | Ala |     |
|     |     |     |     | 425 |     |     |     |     | 430 |     |     |     |     | 435 |     |     |
| TCT | GGA | GTC | CCT | GTT | CGC | TTC | AGT | GGC | AGT | GGG | TCT | GGG | ACC | TCT | TAC | 624 |
| Ser | Gly | Val | Pro | Val | Arg | Phe | Ser | Gly | Ser | Gly | Ser | Gly | Thr | Ser | Tyr |     |
|     |     |     | 440 |     |     |     |     | 445 |     |     |     |     | 450 |     |     |     |
| TCT | CTC | ACA | ATC | AGC | CGA | ATG | GAG | GCT | GAA | GAT | GCT | GCC | ACT | TAT | TAC | 672 |
| Ser | Leu | Thr | Ile | Ser | Arg | Met | Glu | Ala | Glu | Asp | Ala | Ala | Thr | Tyr | Tyr |     |
|     |     | 455 |     |     |     |     | 460 |     |     |     |     | 465 |     |     |     |     |
| TGC | CAG | CAG | TGG | AGT | AGT | TAC | CCA | CCC | ATG | TAC | ACG | TTC | GGA | GGG | GGG | 720 |
| Cys | Gln | Gln | Trp | Ser | Ser | Tyr | Pro | Pro | Met | Tyr | Thr | Phe | Gly | Gly | Gly |     |
|     | 470 |     |     |     |     | 475 |     |     |     |     | 480 |     |     |     |     |     |
| ACC | AAG | CTG | GAA | ATA | AAA |     |     |     |     |     |     |     |     |     |     | 738 |
| Thr | Lys | Leu | Glu | Ile | Lys |     |     |     |     |     |     |     |     |     |     |     |
| 485 |     |     |     |     | 490 |     |     |     |     |     |     |     |     |     |     |     |

( 2 ) INFORMATION FOR SEQ ID NO: 24:

( i ) SEQUENCE CHARACTERISTICS:
        ( A ) LENGTH: 246 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 24:

| Glu | Val | Gln | Leu | Gln | Gln | Ser | Gly | Ala | Glu | Leu | Val | Lys | Pro | Gly | Ala |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Ser | Val | Lys | Leu | Ser | Cys | Lys | Ala | Ser | Gly | Tyr | Thr | Phe | Thr | Ser | His |
|     |     |     | 20 |     |     |     |     | 25 |     |     |     |     | 30 |     |     |
| Trp | Met | His | Trp | Val | Lys | Gln | Arg | Ala | Gly | Gln | Gly | Leu | Glu | Trp | Ile |
|     |     | 35 |     |     |     |     | 40 |     |     |     |     | 45 |     |     |     |
| Gly | Glu | Phe | Asn | Pro | Ser | Asn | Gly | Arg | Thr | Asn | Tyr | Asn | Glu | Lys | Phe |
|     | 50 |     |     |     |     | 55 |     |     |     |     | 60 |     |     |     |     |
| Lys | Ser | Lys | Ala | Thr | Leu | Thr | Val | Asp | Lys | Ser | Ser | Ser | Thr | Ala | Tyr |
| 65 |     |     |     |     | 70 |     |     |     |     | 75 |     |     |     |     | 80 |
| Met | Gln | Leu | Ser | Ser | Leu | Thr | Ser | Glu | Asp | Ser | Ala | Val | Tyr | Tyr | Cys |
|     |     |     |     | 85 |     |     |     |     | 90 |     |     |     |     | 95 |     |
| Ala | Ser | Arg | Asp | Tyr | Asp | Tyr | Asp | Gly | Arg | Tyr | Phe | Asp | Tyr | Trp | Gly |
|     |     |     | 100 |     |     |     |     | 105 |     |     |     |     | 110 |     |     |
| Gln | Gly | Thr | Thr | Val | Thr | Val | Ser | Ser | Gly | Gly | Gly | Gly | Ser | Gly | Gly |
|     |     | 115 |     |     |     |     | 120 |     |     |     |     | 125 |     |     |     |
| Gly | Gly | Ser | Gly | Gly | Gly | Gly | Ser | Gly | Ser | Asp | Ile | Glu | Leu | Thr | Gln |
|     | 130 |     |     |     |     | 135 |     |     |     |     | 140 |     |     |     |     |
| Ser | Pro | Thr | Ile | Met | Ser | Ala | Ser | Pro | Gly | Glu | Lys | Val | Thr | Met | Thr |
| 145 |     |     |     |     | 150 |     |     |     |     | 155 |     |     |     |     | 160 |
| Cys | Ser | Asp | Ser | Ser | Ser | Val | Ser | Tyr | Met | Tyr | Trp | Tyr | Gln | Gln | Lys |
|     |     |     |     | 165 |     |     |     |     | 170 |     |     |     |     | 175 |     |
| Pro | Gly | Ser | Ser | Pro | Arg | Leu | Leu | Ile | Tyr | Asp | Thr | Ser | Asn | Leu | Ala |
|     |     |     | 180 |     |     |     |     | 185 |     |     |     |     | 190 |     |     |
| Ser | Gly | Val | Pro | Val | Arg | Phe | Ser | Gly | Ser | Gly | Ser | Gly | Thr | Ser | Tyr |
|     |     | 195 |     |     |     |     | 200 |     |     |     |     | 205 |     |     |     |
| Ser | Leu | Thr | Ile | Ser | Arg | Met | Glu | Ala | Glu | Asp | Ala | Ala | Thr | Tyr | Tyr |
|     | 210 |     |     |     |     | 215 |     |     |     |     | 220 |     |     |     |     |

| | | | | | | | | | | | | | | |
|---|---|---|---|---|---|---|---|---|---|---|---|---|---|---|
| Cys | Gln | Gln | Trp | Ser | Ser | Tyr | Pro | Pro | Met | Tyr | Thr | Phe | Gly | Gly | Gly |
| 225 | | | | | 230 | | | | | 235 | | | | | 240 |

Thr Lys Leu Glu Ile Lys
                 245

( 2 ) INFORMATION FOR SEQ ID NO: 25:

( i ) SEQUENCE CHARACTERISTICS:
        ( A ) LENGTH: 726 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: mouse
        ( B ) STRAIN: Balb/c
        ( F ) TISSUE TYPE: splenocytes ( v i i ) IMMEDIATE SOURCE:
        ( B ) CLONE: 5 F 1 (single-chain Fv, heavy, light chain,
            linker)

( i x ) FEATURE:
        ( A ) NAME/KEY: CDS
        ( B ) LOCATION:1..726

( x i ) SEQUENCE DESCRIPTION: SEQ ID NO: 25:

| | | | | | | | | | | | | | | | |
|---|---|---|---|---|---|---|---|---|---|---|---|---|---|---|---|
| CAG | GTG | AAA | CTG | CAG | GAG | TCT | GGG | GCT | GAA | CTG | GTG | AAG | CCT | GGG | GCT | 48 |
| Gln | Val | Lys | Leu | Gln | Glu | Ser | Gly | Ala | Glu | Leu | Val | Lys | Pro | Gly | Ala | |
| | | 250 | | | | 255 | | | | 260 | | | | | | |
| TCA | GTG | AAG | TTG | TCC | TGC | AAG | GCT | TCC | GGC | TAC | ACC | TTC | ACC | AGC | CAC | 96 |
| Ser | Val | Lys | Leu | Ser | Cys | Lys | Ala | Ser | Gly | Tyr | Thr | Phe | Thr | Ser | His | |
| | | 265 | | | | 270 | | | | 275 | | | | | | |
| TGG | ATG | CAC | TGG | GTG | AAG | CAG | AGG | GCT | GGA | CAA | GGC | CTT | GAG | TGG | ATC | 144 |
| Trp | Met | His | Trp | Val | Lys | Gln | Arg | Ala | Gly | Gln | Gly | Leu | Glu | Trp | Ile | |
| | 280 | | | | 285 | | | | | 290 | | | | | | |
| GGA | GAG | ATT | AAT | CCC | AGA | ACG | GCG | CCT | ACT | AAC | TAC | AAT | GAG | AAA | TTC | 192 |
| Gly | Glu | Ile | Asn | Pro | Arg | Thr | Ala | Pro | Thr | Asn | Tyr | Asn | Glu | Lys | Phe | |
| 295 | | | | 300 | | | | 305 | | | | | | | 310 | |
| AAG | AGC | AAG | GCC | ACA | CTG | ACT | GTA | GAC | AAA | TCC | TCC | AGC | ACA | GCC | TAC | 240 |
| Lys | Ser | Lys | Ala | Thr | Leu | Thr | Val | Asp | Lys | Ser | Ser | Ser | Thr | Ala | Tyr | |
| | | | | 315 | | | | 320 | | | | | 325 | | | |
| ATG | CAA | CTC | AGC | AGC | CTG | ACA | TCT | GAG | GAC | TCT | GCG | GTC | TAT | TAC | TGT | 288 |
| Met | Gln | Leu | Ser | Ser | Leu | Thr | Ser | Glu | Asp | Ser | Ala | Val | Tyr | Tyr | Cys | |
| | | | 330 | | | | 335 | | | | | | 340 | | | |
| GCC | AGT | CGG | GAC | TAT | GAT | TAC | GAC | GGA | CGG | TAC | TTT | GAC | TAC | TGG | GGC | 336 |
| Ala | Ser | Arg | Asp | Tyr | Asp | Tyr | Asp | Gly | Arg | Tyr | Phe | Asp | Tyr | Trp | Gly | |
| | | 345 | | | | 350 | | | | | 355 | | | | | |
| CAA | GGG | ACA | ACG | GTC | ACC | GTC | TCC | TCA | GGT | GGC | GGT | GGC | TCG | GGC | GGT | 384 |
| Gln | Gly | Thr | Thr | Val | Thr | Val | Ser | Ser | Gly | Gly | Gly | Gly | Ser | Gly | Gly | |
| | | 360 | | | | 365 | | | | | 370 | | | | | |
| GGT | GGG | TCG | GGT | GGC | GGC | GGA | TCT | GAC | ATT | GAG | CTC | ACC | CAG | TCT | CCA | 432 |
| Gly | Gly | Ser | Gly | Gly | Gly | Gly | Ser | Asp | Ile | Glu | Leu | Thr | Gln | Ser | Pro | |
| 375 | | | | | 380 | | | | 385 | | | | | | 390 | |
| ACA | ATC | ATG | TCT | GCA | TCT | CCA | GGG | GAG | AAG | GTC | ACC | ATG | ACC | TGC | AGT | 480 |
| Thr | Ile | Met | Ser | Ala | Ser | Pro | Gly | Glu | Lys | Val | Thr | Met | Thr | Cys | Ser | |
| | | | | 395 | | | | 400 | | | | | 405 | | | |
| GAC | AGC | TCA | AGT | GTA | AGT | TAC | ACG | TAC | TGG | TAC | CAG | CAG | AAG | ACA | GGA | 528 |
| Asp | Ser | Ser | Ser | Val | Ser | Tyr | Thr | Tyr | Trp | Tyr | Gln | Gln | Lys | Thr | Gly | |

|       |       |       |       |       | 410   |       |       |       |       | 415   |       |       |       |       | 420   |       |     |
|-------|-------|-------|-------|-------|-------|-------|-------|-------|-------|-------|-------|-------|-------|-------|-------|-------|-----|
| TCC   | TCC   | CCC   | AGA   | CTC   | CTG   | ATT   | TAT   | GAC   | ACA   | TCC   | AAC   | CTG   | GCT   | TCT   | GGA   |       | 576 |
| Ser   | Ser   | Pro   | Arg   | Leu   | Leu   | Ile   | Tyr   | Asp   | Thr   | Ser   | Asn   | Leu   | Ala   | Ser   | Gly   |       |     |
|       |       | 425   |       |       |       | 430   |       |       |       | 435   |       |       |       |       |       |       |     |
| GTC   | CCT   | GTT   | CGC   | TTC   | AGT   | GGC   | AGT   | GGG   | TCT   | GGG   | ACC   | TCT   | TAC   | TCT   | CTC   |       | 624 |
| Val   | Pro   | Val   | Arg   | Phe   | Ser   | Gly   | Ser   | Gly   | Ser   | Gly   | Thr   | Ser   | Tyr   | Ser   | Leu   |       |     |
|       | 440   |       |       |       |       | 445   |       |       |       | 450   |       |       |       |       |       |       |     |
| ACA   | ATC   | AGC   | CGA   | ATG   | GAG   | GCT   | GAA   | GAT   | GCT   | GCC   | ACT   | TAT   | TAC   | TGC   | CAG   |       | 672 |
| Thr   | Ile   | Ser   | Arg   | Met   | Glu   | Ala   | Glu   | Asp   | Ala   | Ala   | Thr   | Tyr   | Tyr   | Cys   | Gln   |       |     |
| 455   |       |       |       |       | 460   |       |       |       |       | 465   |       |       |       |       | 470   |       |     |
| CAG   | TGG   | AGT   | AGT   | TAC   | CCG   | CTC   | ACG   | TTC   | GGT   | GCT   | GGG   | ACC   | AAG   | CTG   | GAA   |       | 720 |
| Gln   | Trp   | Ser   | Ser   | Tyr   | Pro   | Leu   | Thr   | Phe   | Gly   | Ala   | Gly   | Thr   | Lys   | Leu   | Glu   |       |     |
|       |       |       |       | 475   |       |       |       | 480   |       |       |       |       | 485   |       |       |       |     |
| ATA   | AAA   |       |       |       |       |       |       |       |       |       |       |       |       |       |       |       | 726 |
| Ile   | Lys   |       |       |       |       |       |       |       |       |       |       |       |       |       |       |       |     |

( 2 ) INFORMATION FOR SEQ ID NO: 26:

( i ) SEQUENCE CHARACTERISTICS:
        ( A ) LENGTH: 242 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 26:

| Gln | Val | Lys | Leu | Gln | Ser | Gly | Ala | Glu | Leu | Val | Lys | Pro | Gly | Ala |
|-----|-----|-----|-----|-----|-----|-----|-----|-----|-----|-----|-----|-----|-----|-----|
| 1   |     |     |     | 5   |     |     |     | 10  |     |     |     |     | 15  |     |
| Ser | Val | Lys | Leu | Ser | Cys | Lys | Ala | Ser | Gly | Tyr | Thr | Phe | Thr | Ser | His |
|     |     |     | 20  |     |     |     |     | 25  |     |     |     | 30  |     |     |     |
| Trp | Met | His | Trp | Val | Lys | Gln | Arg | Ala | Gly | Gln | Gly | Leu | Glu | Trp | Ile |
|     |     | 35  |     |     |     |     | 40  |     |     |     |     | 45  |     |     |     |
| Gly | Glu | Ile | Asn | Pro | Arg | Thr | Ala | Pro | Thr | Asn | Tyr | Asn | Glu | Lys | Phe |
|     | 50  |     |     |     |     | 55  |     |     |     |     | 60  |     |     |     |     |
| Lys | Ser | Lys | Ala | Thr | Leu | Thr | Val | Asp | Lys | Ser | Ser | Ser | Thr | Ala | Tyr |
| 65  |     |     |     |     | 70  |     |     |     |     | 75  |     |     |     |     | 80  |
| Met | Gln | Leu | Ser | Ser | Leu | Thr | Ser | Glu | Asp | Ser | Ala | Val | Tyr | Tyr | Cys |
|     |     |     |     | 85  |     |     |     |     | 90  |     |     |     |     | 95  |     |
| Ala | Ser | Arg | Asp | Tyr | Asp | Tyr | Asp | Gly | Arg | Tyr | Phe | Asp | Tyr | Trp | Gly |
|     |     |     | 100 |     |     |     |     | 105 |     |     |     |     | 110 |     |     |
| Gln | Gly | Thr | Thr | Val | Thr | Val | Ser | Ser | Gly | Gly | Gly | Gly | Ser | Gly | Gly |
|     |     |     | 115 |     |     |     |     | 120 |     |     |     |     | 125 |     |     |
| Gly | Gly | Ser | Gly | Gly | Gly | Gly | Ser | Asp | Ile | Glu | Leu | Thr | Gln | Ser | Pro |
|     | 130 |     |     |     |     | 135 |     |     |     |     | 140 |     |     |     |     |
| Thr | Ile | Met | Ser | Ala | Ser | Pro | Gly | Glu | Lys | Val | Thr | Met | Thr | Cys | Ser |
| 145 |     |     |     |     | 150 |     |     |     |     | 155 |     |     |     |     | 160 |
| Asp | Ser | Ser | Ser | Val | Ser | Tyr | Thr | Tyr | Trp | Tyr | Gln | Gln | Lys | Thr | Gly |
|     |     |     |     | 165 |     |     |     |     | 170 |     |     |     |     | 175 |     |
| Ser | Ser | Pro | Arg | Leu | Leu | Ile | Tyr | Asp | Thr | Ser | Asn | Leu | Ala | Ser | Gly |
|     |     |     | 180 |     |     |     |     | 185 |     |     |     |     | 190 |     |     |
| Val | Pro | Val | Arg | Phe | Ser | Gly | Ser | Gly | Ser | Gly | Thr | Ser | Tyr | Ser | Leu |
|     |     | 195 |     |     |     |     | 200 |     |     |     |     | 205 |     |     |     |
| Thr | Ile | Ser | Arg | Met | Glu | Ala | Glu | Asp | Ala | Ala | Thr | Tyr | Tyr | Cys | Gln |
|     | 210 |     |     |     |     | 215 |     |     |     |     | 220 |     |     |     |     |
| Gln | Trp | Ser | Ser | Tyr | Pro | Leu | Thr | Phe | Gly | Ala | Gly | Thr | Lys | Leu | Glu |
| 225 |     |     |     |     | 230 |     |     |     |     | 235 |     |     |     |     | 240 |
| Ile | Lys |     |     |     |     |     |     |     |     |     |     |     |     |     |     |

( 2 ) INFORMATION FOR SEQ ID NO: 27:

( i ) SEQUENCE CHARACTERISTICS:
        ( A ) LENGTH: 726 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: mouse
        ( B ) STRAIN: Balb/c
        ( F ) TISSUE TYPE: splenocytes ( v i i ) IMMEDIATE SOURCE:
        ( A ) LIBRARY: 7 G 1 (single-chain Fv, heavy, light chain, linker)

( i x ) FEATURE:
        ( A ) NAME/KEY: CDS
        ( B ) LOCATION:1..726

( x i ) SEQUENCE DESCRIPTION: SEQ ID NO: 27:

```
GAG  GTC  AAG  CTG  CAG  CAG  TCA  GGG  GCT  GAA  CTG  GTG  AAG  CCT  GGG  GCT        48
Glu  Val  Lys  Leu  Gln  Gln  Ser  Gly  Ala  Glu  Leu  Val  Lys  Pro  Gly  Ala
     245                           250                           255

TCA  GTG  AAG  TTG  TCC  TGC  AAG  GCT  TCC  GGC  TAC  ACC  TTC  ACC  AGC  CAC        96
Ser  Val  Lys  Leu  Ser  Cys  Lys  Ala  Ser  Gly  Tyr  Thr  Phe  Thr  Ser  His
     260                           265                           270

TTG  GAT  CAC  TGG  GTG  AAG  CAG  AGG  GGC  TGG  CAA  GGC  CTT  GAG  TGG  ATC       144
Leu  Asp  His  Trp  Val  Lys  Gln  Arg  Gly  Trp  Gln  Gly  Leu  Glu  Trp  Ile
275            280                           285                           290

GGA  CAG  TTT  AAT  CCC  AGC  AAC  GGC  CGT  ACT  AAC  TAC  AAT  GAG  AAA  TTC       192
Gly  Gln  Phe  Asn  Pro  Ser  Asn  Gly  Arg  Thr  Asn  Tyr  Asn  Glu  Lys  Phe
               295                           300                           305

AAG  AGC  AAG  GCC  ACA  CTG  ACT  GTA  GAC  AAA  TCC  TCC  AGC  ACA  GCC  TAC       240
Lys  Ser  Lys  Ala  Thr  Leu  Thr  Val  Asp  Lys  Ser  Ser  Ser  Thr  Ala  Tyr
               310                           315                           320

ATC  GAA  CTC  AGC  AGC  CTG  ACA  TCT  GAG  GAC  TGC  TCG  GTC  TAT  TAC  TGT       288
Ile  Glu  Leu  Ser  Ser  Leu  Thr  Ser  Glu  Asp  Cys  Ser  Val  Tyr  Tyr  Cys
               325                           330                           335

GCC  AGT  CGG  GAC  TAT  GAT  TAC  GAC  GGA  CGG  TAC  TTT  GAC  TAC  TGG  GGC       336
Ala  Ser  Arg  Asp  Tyr  Asp  Tyr  Asp  Gly  Arg  Tyr  Phe  Asp  Tyr  Trp  Gly
     340                           345                           350

CAA  GGG  ACC  ACG  GTC  ACC  GTC  TCC  TCA  GGT  GGC  GGT  GGC  TCG  GGC  GGT       384
Gln  Gly  Thr  Thr  Val  Thr  Val  Ser  Ser  Gly  Gly  Gly  Gly  Ser  Gly  Gly
355            360                           365                           370

GGT  GGG  TCG  GGT  GGC  GGC  GGA  TCT  GAC  ATT  GAG  CTC  ACC  CAG  TCT  CCA       432
Gly  Gly  Ser  Gly  Gly  Gly  Ser  Asp  Ile  Glu  Leu  Thr  Gln  Ser  Pro
               375                           380                           385

ACA  ATC  ATG  TCT  GCA  TCT  CCA  GGG  GAG  AAG  GTC  ACC  ATG  ACC  TGC  AGT       480
Thr  Ile  Met  Ser  Ala  Ser  Pro  Gly  Glu  Lys  Val  Thr  Met  Thr  Cys  Ser
               390                           395                           400

GAC  AGC  TCA  AGT  GTA  AGT  TAC  ATG  TAC  TGG  TAC  CAG  CAG  AAG  ACA  GGA       528
Asp  Ser  Ser  Ser  Val  Ser  Tyr  Met  Tyr  Trp  Tyr  Gln  Gln  Lys  Thr  Gly
          405                           410                           415

TCC  TCC  CCC  AGA  CTT  CTG  ATT  TAT  GAC  ACA  TCC  AAC  CTG  GCT  TCT  GGA       576
Ser  Ser  Pro  Arg  Leu  Leu  Ile  Tyr  Asp  Thr  Ser  Asn  Leu  Ala  Ser  Gly
          420                           425                           430
```

| | | | | | | | | | | | | | | | | |
|---|---|---|---|---|---|---|---|---|---|---|---|---|---|---|---|---|
| GTC | CCT | GTT | CGC | TTC | AGT | GGC | AGT | GGG | TCT | GGG | ACC | TCT | TAC | TCT | CTC | 624 |
| Val | Pro | Val | Arg | Phe | Ser | Gly | Ser | Gly | Ser | Gly | Thr | Ser | Tyr | Ser | Leu | |
| 435 | | | | 440 | | | | | 445 | | | | | | 450 | |
| ACA | ATC | AGC | CGA | ATG | GAG | GCT | GAA | GAT | GCT | GCC | ACT | TAT | TAC | TGC | CAG | 672 |
| Thr | Ile | Ser | Arg | Met | Glu | Ala | Glu | Asp | Ala | Ala | Thr | Tyr | Tyr | Cys | Gln | |
| | | | | 455 | | | | | 460 | | | | | 465 | | |
| CAG | TGG | AGT | AGT | TAC | CCG | CTC | ACG | TTC | GGT | GCT | GGG | ACC | AAG | CTG | GAA | 720 |
| Gln | Trp | Ser | Ser | Tyr | Pro | Leu | Thr | Phe | Gly | Ala | Gly | Thr | Lys | Leu | Glu | |
| | | | 470 | | | | | 475 | | | | | 480 | | | |
| ATA | AAA | | | | | | | | | | | | | | | 726 |
| Ile | Lys | | | | | | | | | | | | | | | |

( 2 ) INFORMATION FOR SEQ ID NO: 28:

( i ) SEQUENCE CHARACTERISTICS:
        ( A ) LENGTH: 242 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 28:

| | | | | | | | | | | | | | | |
|---|---|---|---|---|---|---|---|---|---|---|---|---|---|---|
| Glu | Val | Lys | Leu | Gln | Gln | Ser | Gly | Ala | Glu | Leu | Val | Lys | Pro | Gly | Ala |
| 1 | | | | 5 | | | | | 10 | | | | | 15 | |
| Ser | Val | Lys | Leu | Ser | Cys | Lys | Ala | Ser | Gly | Tyr | Thr | Phe | Thr | Ser | His |
| | | | 20 | | | | | 25 | | | | | 30 | | |
| Leu | Asp | His | Trp | Val | Lys | Gln | Arg | Gly | Trp | Gln | Gly | Leu | Glu | Trp | Ile |
| | | | 35 | | | | | 40 | | | | | 45 | | |
| Gly | Gln | Phe | Asn | Pro | Ser | Asn | Gly | Arg | Thr | Asn | Tyr | Asn | Glu | Lys | Phe |
| | | 50 | | | | | 55 | | | | | 60 | | | |
| Lys | Ser | Lys | Ala | Thr | Leu | Thr | Val | Asp | Lys | Ser | Ser | Thr | Ala | Tyr | |
| 65 | | | | | 70 | | | | | 75 | | | | | 80 |
| Ile | Glu | Leu | Ser | Ser | Leu | Thr | Ser | Glu | Asp | Cys | Ser | Val | Tyr | Tyr | Cys |
| | | | | 85 | | | | | 90 | | | | | 95 | |
| Ala | Ser | Arg | Asp | Tyr | Asp | Tyr | Asp | Gly | Arg | Tyr | Phe | Asp | Tyr | Trp | Gly |
| | | | 100 | | | | | 105 | | | | | 110 | | |
| Gln | Gly | Thr | Thr | Val | Thr | Val | Ser | Ser | Gly | Gly | Gly | Gly | Ser | Gly | Gly |
| | | 115 | | | | | 120 | | | | | 125 | | | |
| Gly | Gly | Ser | Gly | Gly | Gly | Gly | Ser | Asp | Ile | Glu | Leu | Thr | Gln | Ser | Pro |
| 130 | | | | | 135 | | | | | 140 | | | | | |
| Thr | Ile | Met | Ser | Ala | Ser | Pro | Gly | Glu | Lys | Val | Thr | Met | Thr | Cys | Ser |
| 145 | | | | | 150 | | | | | 155 | | | | | 160 |
| Asp | Ser | Ser | Ser | Val | Ser | Tyr | Met | Tyr | Trp | Tyr | Gln | Gln | Lys | Thr | Gly |
| | | | | 165 | | | | | 170 | | | | | 175 | |
| Ser | Ser | Pro | Arg | Leu | Leu | Ile | Tyr | Asp | Thr | Ser | Asn | Leu | Ala | Ser | Gly |
| | | | 180 | | | | | 185 | | | | | 190 | | |
| Val | Pro | Val | Arg | Phe | Ser | Gly | Ser | Gly | Ser | Gly | Thr | Ser | Tyr | Ser | Leu |
| | | | 195 | | | | | 200 | | | | | 205 | | |
| Thr | Ile | Ser | Arg | Met | Glu | Ala | Glu | Asp | Ala | Ala | Thr | Tyr | Tyr | Cys | Gln |
| | | 210 | | | | | 215 | | | | | 220 | | | |
| Gln | Trp | Ser | Ser | Tyr | Pro | Leu | Thr | Phe | Gly | Ala | Gly | Thr | Lys | Leu | Glu |
| 225 | | | | | 230 | | | | | 235 | | | | | 240 |
| Ile | Lys | | | | | | | | | | | | | | |

( 2 ) INFORMATION FOR SEQ ID NO: 29:

( i ) SEQUENCE CHARACTERISTICS:
        ( A ) LENGTH: 24 base pairs
        ( B ) TYPE: nucleic acid (C) STRANDEDNESS: single
        (D) TOPOLOGY: linear (ii) MOLECULE TYPE: other nucleic acid
        (A) DESCRIPTION: /desc = "FORWARD PRIMER"

(iii) HYPOTHETICAL: NO (iv) ANTI-SENSE: NO (xi) SEQUENCE DESCRIPTION: SEQ ID NO:29:

CCGTTTCAGC TCGAGCTTGG TCCC                                                                          24

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "BACK PRIMER"

(iii) HYPOTHETICAL: NO (xi) SEQUENCE DESCRIPTION: SEQ ID NO:30:

GACATTGAGC TCACCCAGTC TCCA                                                                          24